(12) United States Patent
Facchiano et al.

(10) Patent No.: US 7,009,036 B2
(45) Date of Patent: Mar. 7, 2006

(54) PEPTIDE INHIBITING PLATELET DERIVED GROWTH FACTOR (PDGF-BB) AND FIBROBLAST GROWTH FACTOR (BFGF) ACTIVITY

(75) Inventors: Antonio Facchiano, Rome (IT); Francesco Facchiano, Rome (IT); Angelo Facchiano, Naples (IT)

(73) Assignee: Provincia Italiana Della Congregazione Dei Figli Dell'Immacolata Concezione—Instituto Dermopatico Dell'Immacolata, Rome (IT)

( * ) Notice: Subject to any disclaimer, the term of this patent is extended or adjusted under 35 U.S.C. 154(b) by 318 days.

(21) Appl. No.: 10/077,746

(22) Filed: Feb. 20, 2002

(65) Prior Publication Data

US 2002/0119931 A1   Aug. 29, 2002

(30) Foreign Application Priority Data

Feb. 21, 2001  (IT) .......................... RM2001A0088

(51) Int. Cl.
C07K 17/00 (2006.01)
A61K 38/00 (2006.01)

(52) U.S. Cl. ...................................... 530/350

(58) Field of Classification Search .................... 514/2, 514/12; 530/300, 350
See application file for complete search history.

(56) References Cited

U.S. PATENT DOCUMENTS 5,252,718 A   10/1993   Baird et al.

FOREIGN PATENT DOCUMENTS

WO   00/53219         9/2000
WO   00/72004 A2   11/2000

OTHER PUBLICATIONS

Antonio Facchiano et al., "Identification of a Novel Domain of Fibroblast Growth Factor 2 Controlling Its Angiogenic Properties," The Journal of Biological Chemistry, V. 278, 2003, pp. 8751-8760.

Primary Examiner—Jon Weber
Assistant Examiner—Agnes Rooke
(74) Attorney, Agent, or Firm—Young & Thompson

(57) ABSTRACT

A novel peptide, derived from the human fibroblast growth factor (bFGF), is identified. The molecule is able to inhibit in vitro the effects of Platelet Derived Growth Factor (PDGF-BB) and basic Fibroblast Growth Factor (bFGF) on primary rat smooth muscle cells (RASMC) and primary bovine endothelial cells (BAEC) The molecule is also able to inhibit in vivo angiogenesis CD1 mice.

1 Claim, 7 Drawing Sheets

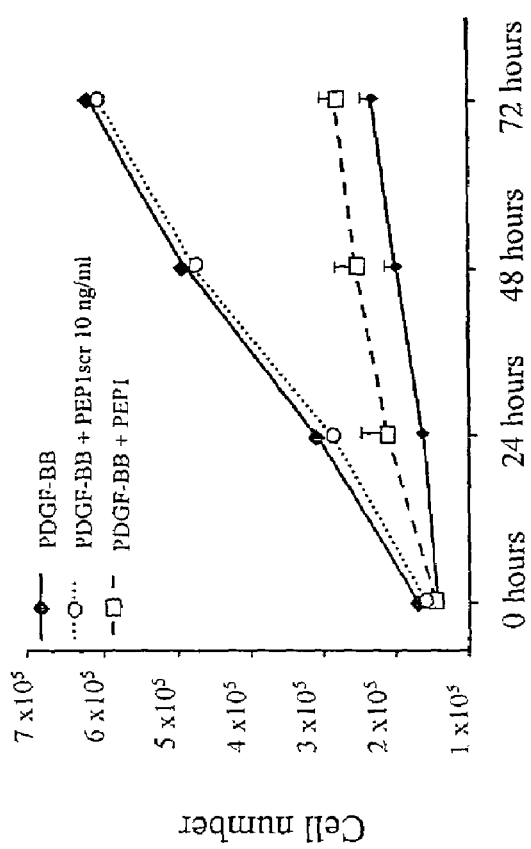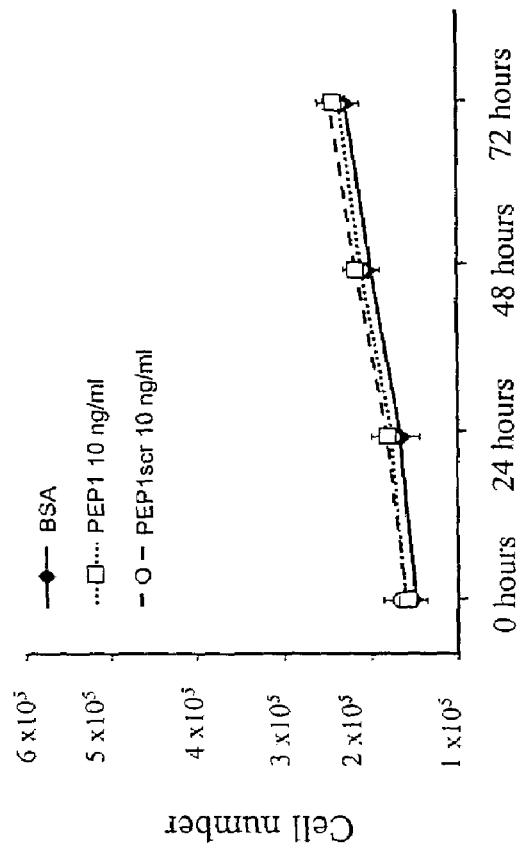

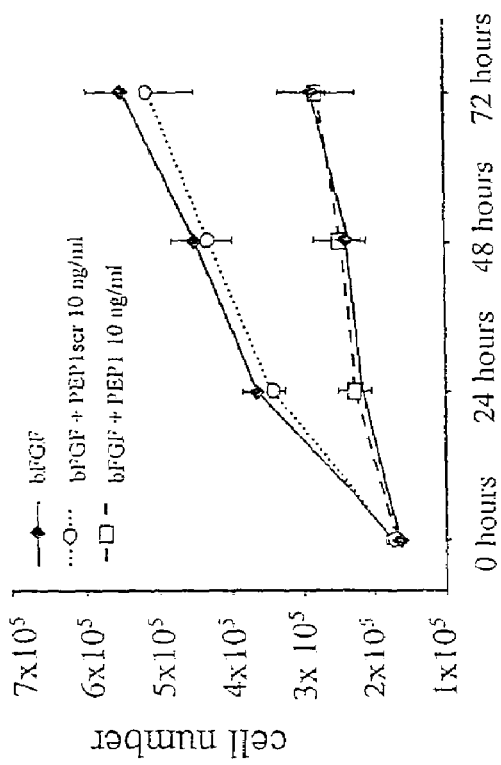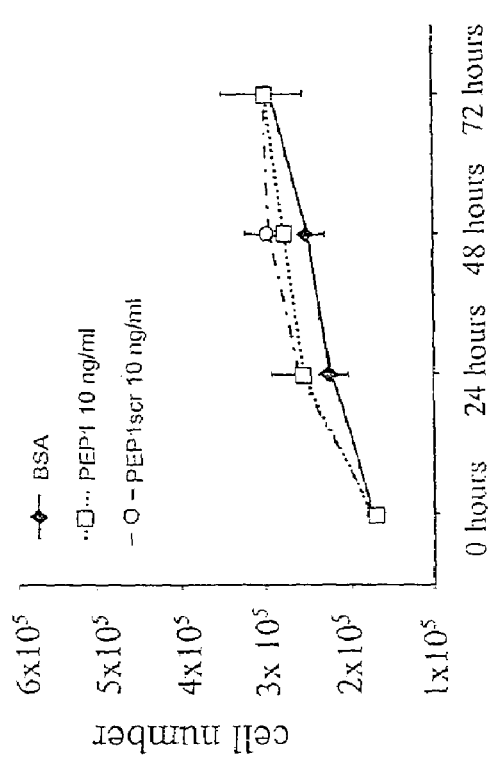

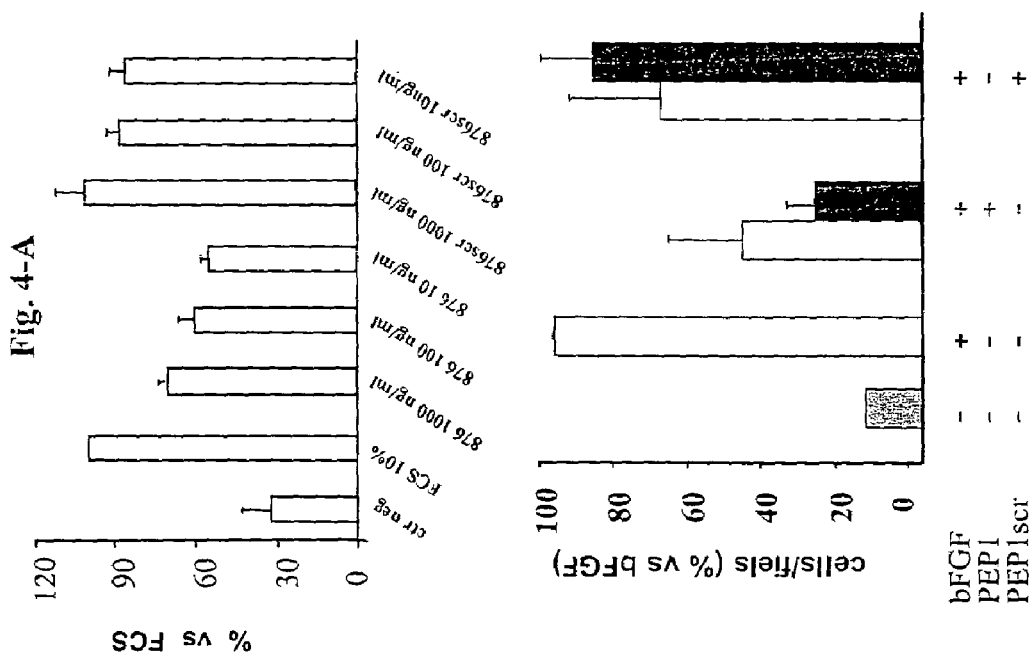

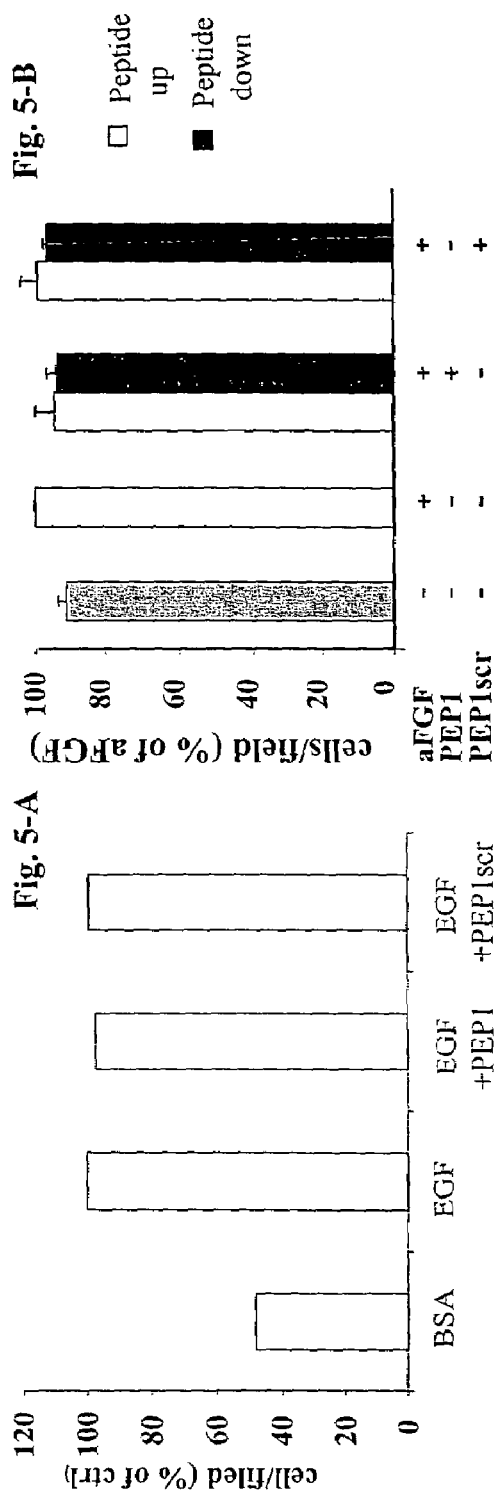
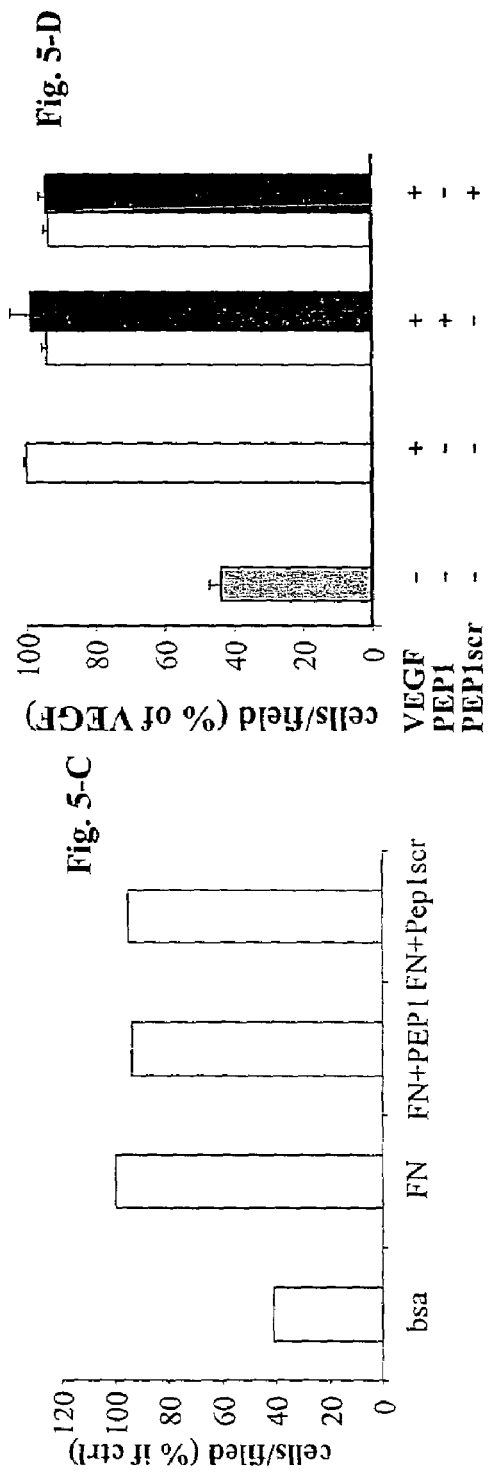

PEPTIDE INHIBITING PLATELET DERIVED GROWTH FACTOR (PDGF-BB) AND FIBROBLAST GROWTH FACTOR (BFGF) ACTIVITY

The present invention concerns the identification and the synthesis of a peptide, derived from the basic human fibroblast growth factor (bFGF), having the following primary structure:

Asp-Pro-His-Ile-Lys-Leu-Gln-Leu-Gln-Ala-Glu hereafter referred to as PEP1 (SEQ ID NO: 1).

Said molecule, showing analogy with a sequence of bFGF, namely inhibits in vitro as well as in vivo PDGF-BB and bFGF effects.

More particularly, in vitro experimentation on primary rat smooth muscle cells (RASMC) and primary bovine endothelial cells (BAEC) indicated that said molecule is an efficient inhibitor of cell proliferation and migration at a dose that is not toxic for cells.

Moreover, in vivo experimentation carried out on reconstituted basement membrane plugs, subcutaneously injected in CD1 mice demonstrated that said molecule strongly inhibits bFGF-induced angiogenesis.

Reported results suggest that PEP1 might be used for the treatment of diseases with abnormal proliferation and migration of vascular cells such as restenosis after angioplasty, atherosclerosis, tumor growth and metastasis dissemination.

Growth factors, such as Platelet Derived Growth Factor (PDGF-BB) and basic Fibroblast Growth Factor (bFGF) play a crucial role in the proliferation and differentiation of many cell types. In fact, increased levels and/or activity of these factors occur in several pathologies, including tumor growth and blood-vessel diseases like atherosclerosis.

Platelet Derived Growth Factor (PDGF-BB) and basic Fibroblast Growth Factor (bFGF) are both essential for the phatogenesis of angiogenesis-related diseases since they directly modulate cell proliferation and migration within vascular wall (Ross, R., et al. 1990, Science, 248, 1009–1012; Ross, R. 1993, Nature, 362, 801–809).

Angiogenesis is a key process for tissue development, as well as tumor growth and dissemination. It is controlled by several factors modulating cell differentiation, proliferation and migration (Holash, J., 1999, Oncogene, 18, 5356–5362; Zetter, B. R. et al., 1998, Annu. Rev. Med., 49, 407–424).

Several different molecules, such as antibodies neutralising PDGF and bFGF (Rutherford et al., Atherosclerosis, 1997, 45–51) and oligonucleotides inhibiting PDGF receptor expression (Sirois, M. G. et al., 1997, Circulation, 95, 669–676), were successfully used in vivo to inhibit diseases with abnormal proliferation and migration of vascular cells such as restenosis. Furthermore, specific inhibitors currently available are able to interfere with the receptorbinding or receptor dimerization or signaling (Heldin, C. H. et al., 1998, BBA, F79–F113).

PDGF and bFGF are required for tumor cells growth in vitro, growth of solid tumors in vivo, as well as metastases dissemination (Shawver, L. K. et al., 1997, Clin. Cancer Res., 3, 1167–1177; Vignaud, J. M. et al., 1994, Cancer Res., 54, 5455–5463; Chandler, L. A. et al., 1999, Int. J. Cancer, 81, 451–458; Westphal, J. R. et al., 2000, Int. J. Cancer, 15,86 (6), 768–776).

Inhibiting the activity and/or the signaling of PDGF and bFGF led to effective reduction of tumor growth and metastasis dissemination (Abramovich, R. et al., 1999, Br. J. Cancer, 79 (9–10), 1392-8; Bagheri-Yarmand, R. et al., 1998, Br. J. Cancer, 78 (1), 1118; Sola, F. et al, 1995, Invasion Metastasis, 15 (5–6), 222–231; Wang, Y. et al., 1997, Nature Med., 3, 887–893).

Therefore, specific antagonists of PDGF and bFGF are potential candidates for the treatment of proliferative diseases and angiogenesis-related disorders.

According to recent data collected by the same inventors, PDGF-BB and bFGF play an unsuspected role in the modulation of their pro-angiogenic functions. In particular, the inhibitory role of bFGF on cell proliferation and migration in addition to its pro-angiogenic effect, has been demonstrated (Facchiano, A. et al., 2000, J. Cell. Sci., 113, 2855–2863).

Moreover, the factors regulating the protein-folding and the structure-biological function relationship has been investigated (Ragone, R. et al., 1987, Italian J. of Biochem., 36, 306–309; Facchiano, F. et al., 1988, CABIOS, 4, 2, 303–305; Ragone, R. et al., 1989, Protein Engineering, 2, 7, 497–504; Facchiano, A. M. et al., 1989, CABIOS, 5, 4, 299–303; Facchiano, A. M. et al., 1991, CABIOS, 7, 3, 395–396; Facchiano, A. et al., 1993, J. Mol. Evol., 36 (5), 448–457; Benvenga, S. et al., 1993, EOS-J. of Immunol. and Immunopharm., 13 (1), 18–19; Facchiano, A., 1995, J. Mol. Evol., 40, 570–577; Facchiano, A., 1996, Trends in Genetics, 12(5), 168–169; Scarselli, M. et al., 1997, J. Peptide Sci., 3, 1–9; Benvenga, S. et al., 1999, Amyloid, 6 (4), 250–255; Facchiano, A. M., 1999, Protein Eng., 12 (10),893; Pozzetto, U. et al., 2000, Transplant Int., Suppl. n. 1, 13, S306–S310; Facchiano, A. M., 2000, Bioinformatics, 16 (3), 292–293).

In the present invention, by investigating protein structure, regions of bFGF sequence potentially responsible of its biological activity have been identified. Among these regions, a peptide having the following primary structure:

In the present invention, by investigating protein structure, regions of bFGF sequence potentially responsible of its biological activity have been identified. Among these regions, a peptide having the following primary structure:

Asp-Pro-His-Ile-Lys-Leu-Gln-Leu-Gln-Ala-Glu (SEQ ID NO:1; here referred to as PEP1), derived from human bFGF turned out to be a strong inhibitor in vitro of bFGF, PDGF-BB and fetal calf serum (FCS) effects, such as cell proliferation and migration observed in primary rat smooth muscle cells (RASMC) and primary bovine endothelial cells (BAEC). Said activity has been observed at a dose as low as 10 nanograms/milliliter and PEP1 is not toxic at this dose in vitro. The heat-denatured and the scrambled version (with random aminoacid sequence) of PEP1 were used as control: both do not show any activity.

Moreover, PEP1 even show inhibitory activity in vivo; it is, indeed, able to inhibit angiogenesis in reconstituted basement membrane plugs, subcutaneously injected in CD1 mice.

Accordingly with what previously detected, PEP1 synthesis was achieved by automatic synthetizer, using the standard technique named f-moc.

After that, three different batches of PEP1 were tested and they gave similar results in the biological assays. Moreover, a scrambled version of the peptide (PEP1scr) was prepared and after used as negative control in all the experiments.

Several in vitro and in vivo test were carried out on said molecule and they revealed the functional characteristics of said peptide.

The results obtained are reported in the accompanying drawings:

FIG. 2A shows PEP1 and PEPscr effect on RASMC proliferation induced by PDGF-BB (10 ng/ml);

FIG. 2B shows PEP1 and PEP1scr effect on RASMC spontaneous proliferation in the presence of BSA;

FIG. 3A shows PEP1 and PEPscr effect on BAEC proliferation induced by PDGF-BB (10 ng/ml);

FIG. 3B shows PEP1 and PEP1scr effect on BAEC spontaneous proliferation in the presence of BSA;

FIG. 4A shows the effect in the presence or in the absence of PEP1 and PEPscr (10 ng/ml) on BAEC migration induced by FCS (1%);

FIG. 4B shows the effect in the presence or in the absence of PEP1 and PEPscr (10 ng/ml) on BAEC migration induced by PDGFD-BB (10 ng/ml);

FIG. 4C shows the effect in the presence or in the absence of PEP1 and PEPscr (10 ng/ml) on BAEC migration induced by bFGF (10 ng/ml);

FIG. 5A shows the effect in the presence or in the absence of PEP1 and PEPscr (10 ng/ml) on BAEC migration induced by EGF (10 ng/ml);

FIG. 5B shows the effect in the presence or in the absence of PEP1 and PEPscr (10 ng/ml) on BAEC migration induced by aFGF (10 ng/ml);

FIG. 5C shows the effect in the presence or in the absence of PEP1 and PEPscr (10 ng/ml) on BAEC migration induced by Fibronectin (10 ng/ml);

FIG. 5D shows the effect in the presence or in the absence of PEP1 and PEPscr (10 ng/ml) on BAEC migration induced by VEGF (10 ng/ml);

In Vitro Pep1 Activity Assay

This test was carried out on Primary rat aorta smooth muscle cells (RASMC) obtained from six-month old male Wistar rats following a well known technique (Sterpetti, A. V. et al., 1992, J. Vasc. Surg., 6, 16–20); primary bovine aortic endothelial cells (BAEC) were obtained according to previously described protocols (D'Arcangelo, D. et al., 2000, Circ.Res., 86, 312–318).

Migration Assay

Cell migration is a key process for the development of new blood-vessels. Consequently, PEP1 effect on cell migration induced by several different chemoattractant factors has been evaluated mainly on endothelial cells (BAEC). Migration assays were carried out in modified Boyden chambers (Neuroprobe Inc.), following known standard techniques (Albini, A. et al., 1995, Int. J. Cancer, 61, 121–129; Facchiano, A. et al., 2000, J. Cell. Sci., 113, 2855–2863). Cells were dispensed in the upper portion of the Boyden chamber. Chemoattractant factor were calf fetal serum (FCS) 10% or the following human recombinant factors: PDGF-BB, bFGF and vascular endothelial growth factor (VEGF). PEP1 PEPscr (scrambled control) diluted in water, were added to the growth factor solution at the reported final concentration. Thus chemotaxis induced by bFGF (10 ng/ml), or PDGF-BB (10 ng/ml), or FCS (2%), in the absence or in the presence of long/ml PEP1 and PEP1scr, was evaluated.

All the migration assays were carried out at 37° C. in 5% $CO_2$, for a total time of 5 hours; then filters were removed, fixed with absolute ethanol and stained with toluidine blue. Cells migrated were counted at 400× magnification in 15 fields for each filter and the average number of cell/field was reported. All the experiments were performed at least 3 times in duplicate.

The experiments show that, in every condition, PEP1 markedly inhibit, and in a rate more than 50%, BAEC migration, but PEP1scr do not have any effect (FIGS. 4A, 4B e 4C). When bFGF or PDGF-BB were tested, PEP1 was either dispensed in the lower and in the upper portion of the Boyden chamber; a slightly better inhibitory activity was observed when it was dispensed in the lower portion of the Boyden chamber.

In contrast, PEP1scr control does not show any activity when dispensed in both portion of the Boyden chamber. To evaluate the specificity of said inhibitory effect, PEP1 effect on other chemoattractans was tested. PEP1 and PEP1scr do not affect Endothelial cell migration induced by aFGF or VEGF or EGF or Fibronectin (FIGS. 5A, 5B, 5C and 5D), indicating that said molecule specifically affect bFGF and PDGF-BB.

Figure 6:
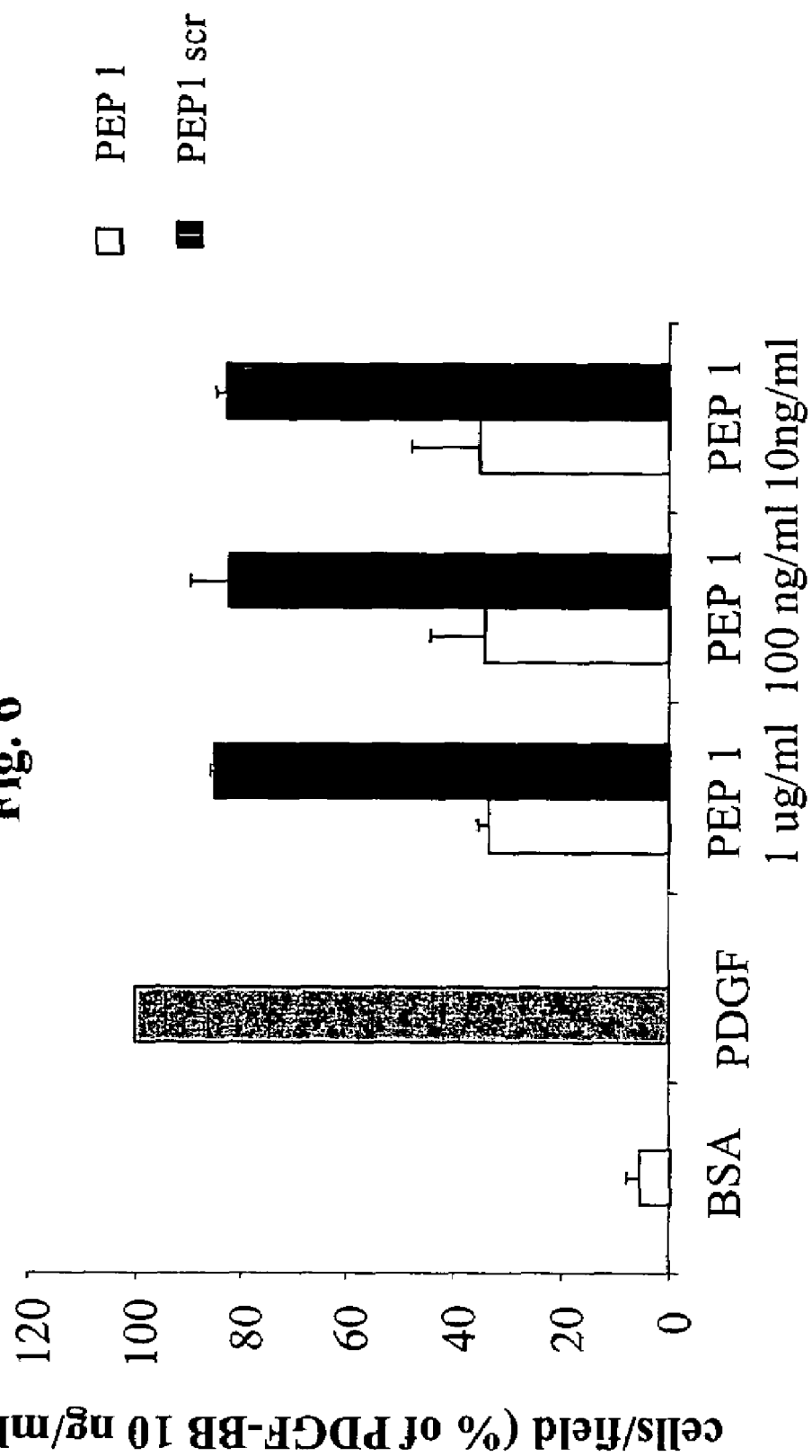
FIG. 6 shows PEP1 and PEP1scr effect on RASMC migration induced by PDGF-BB (10 ng/ml)

Similar results were obtained in chemotaxis assays carried on RASMC induced by PDGF-BB and FCS. PEP1 inhibits RASMC migration (i.e. about 60%), while PEP1scr is inactive (FIG. 6).

Proliferation Assay

Proliferation assay was carried out on primary rat aorta SMC and on primary bovine aortic endothelial cells (BAEC). Cells were plated in six-well plates ($1 \times 10^5$ cells/plate) and grown for 24 hours in Dulbecco Modified eagle's medium (DMEM) supplemented with 10% FBS, at 37° C. in 5% $CO_2$. Then, the medium was replaced with DMEM medium containing 0.1% BSA for 24 hours. Subsequently, the medium was replaced with fresh medium containing either 0.1% BSA alone or 0.1% BSA with growth factors at 10 ng/ml final concentration or fetal calf serum (FCS) al 10%, in the absence or in the presence of PEP1 or control peptide. Each assay was carried out for mounting period of time up to a maximum time of three days and the cell were harvested and counted with hemacytometer.

Figure 1:
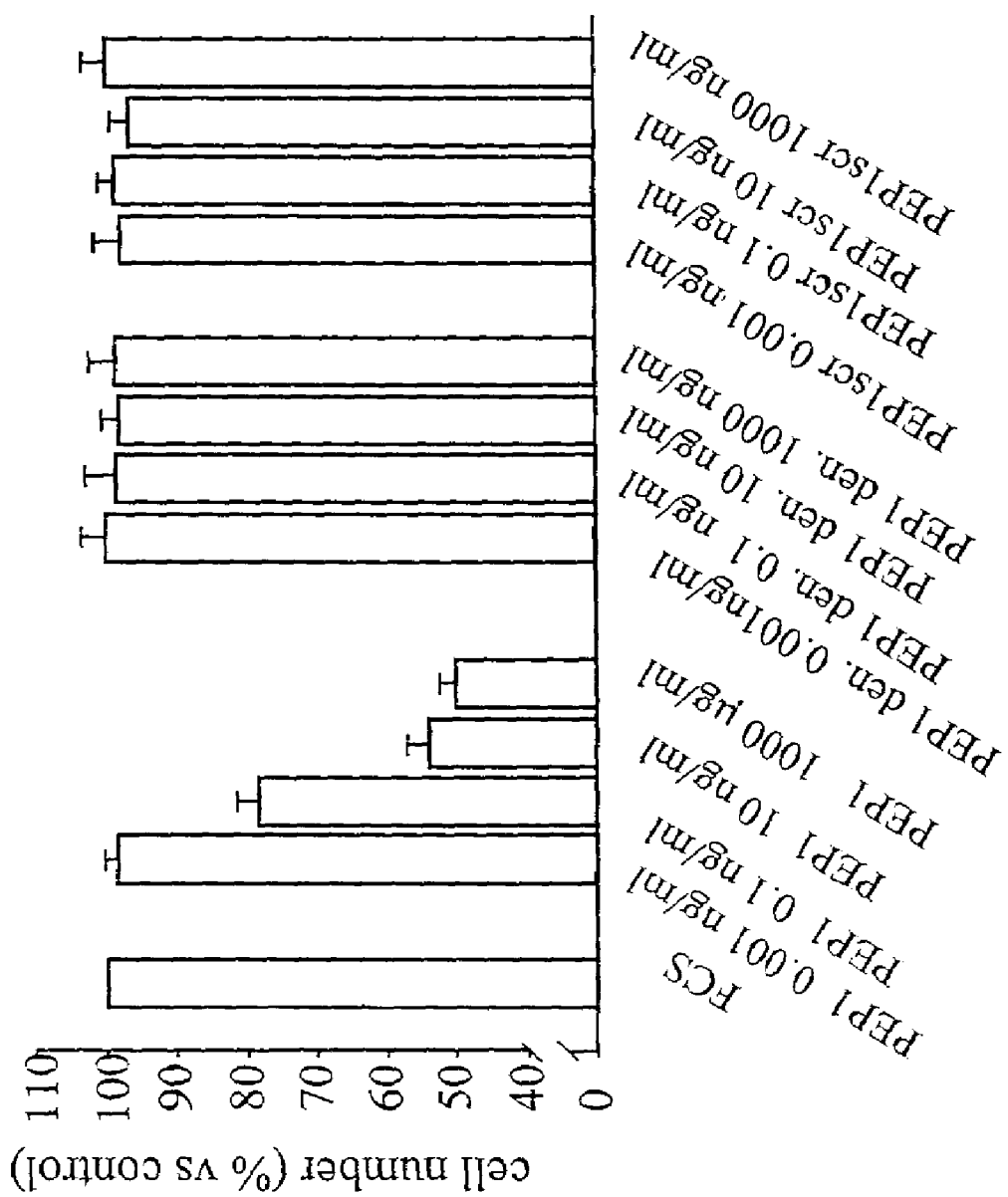
FIG. 1 shows the results of dose-dependent experiments carried out on RASMC. RASMC proliferation induced by 10% FCS was evaluated after 48 hours, in the absence and in the presence of different PEP1 doses, ranging from 1 g/ml to 1 pg/ml.

First of all, PEP1 was tested in dose-dependence experiments: RASMC proliferation induced by FCS 10%, was evaluated at 48 hours, in the presence and in the absence of different PEP1 doses, ranging from 1 µg/ml to 1 µg/ml (FIG. 1). The heat-denatured PEP1 and the scrambled version of PEP1 were used as control. PEP1 showed a dose-dependent inhibitory activity, which reached 60% inhibitory effect at 10 ng/ml, while the control peptides did not show any activity. Consequently, the dose of long/ml was chosen for the following in vitro experiments.

The effect of PEP1 was tested on proliferation induced by PDGF-BB and bFGF (10 ng/ml each), in RASMC and BAEC. FIG. 2A shows the marked inhibition of proliferation induced by PDGF-BB. In time course experiments, proliferation induced by PDGF-BB (10 ng/ml) was significantly inhibited in the presence of PEP1 at all time points. PEP1 block almost completely cell proliferation, while the control scrambled peptide (PEP1scr) is not effective at any time (FIG. 2A).

Spontaneous proliferation (in the presence of bovine serum albumin, BSA) is not significantly affected by PEP1 nor by PEP1scr at any time, indicating that both molecules are not toxic per se at the tested doses on RASMC (FIG. 2B), nor on BAEC (FIG. 3B). Moreover, PEP1 shows similar inhibitory effect on BAEC stimulated by bFGF (10 ng/ml) (FIG. 3A).

Then the following in vivo experiment was carried out:

Angiogenesis on Reconstituted Basement Membrane Plugs

Angiogenesis on reconstituted basement membrane plugs (named "Matrigel", produced by Collaborative Biomedical Products, Beckton-Dickinson) was carried out as previously reported (Muhlhauser, J., 1995,J. Circ. Res., 77, 1077–1086). Briefly, reconstituted basement membrane plugs added with bFGF (150 ng/ml) alone or in the presence of PEP1 (10 micrograms/ml) were subcutaneusly injected in CD1 mice (female, 19 weeks age). bFGF induces the formation of capillary network within 7 days, therefore plugs were excised 7 days after injection and included in paraffin. Obtained slides were stained with trichrome-Masson staining procedure and analysed with an optical image analizer and the number of vessels per mm$^2$ within plugs was quantified.

Figure 7:
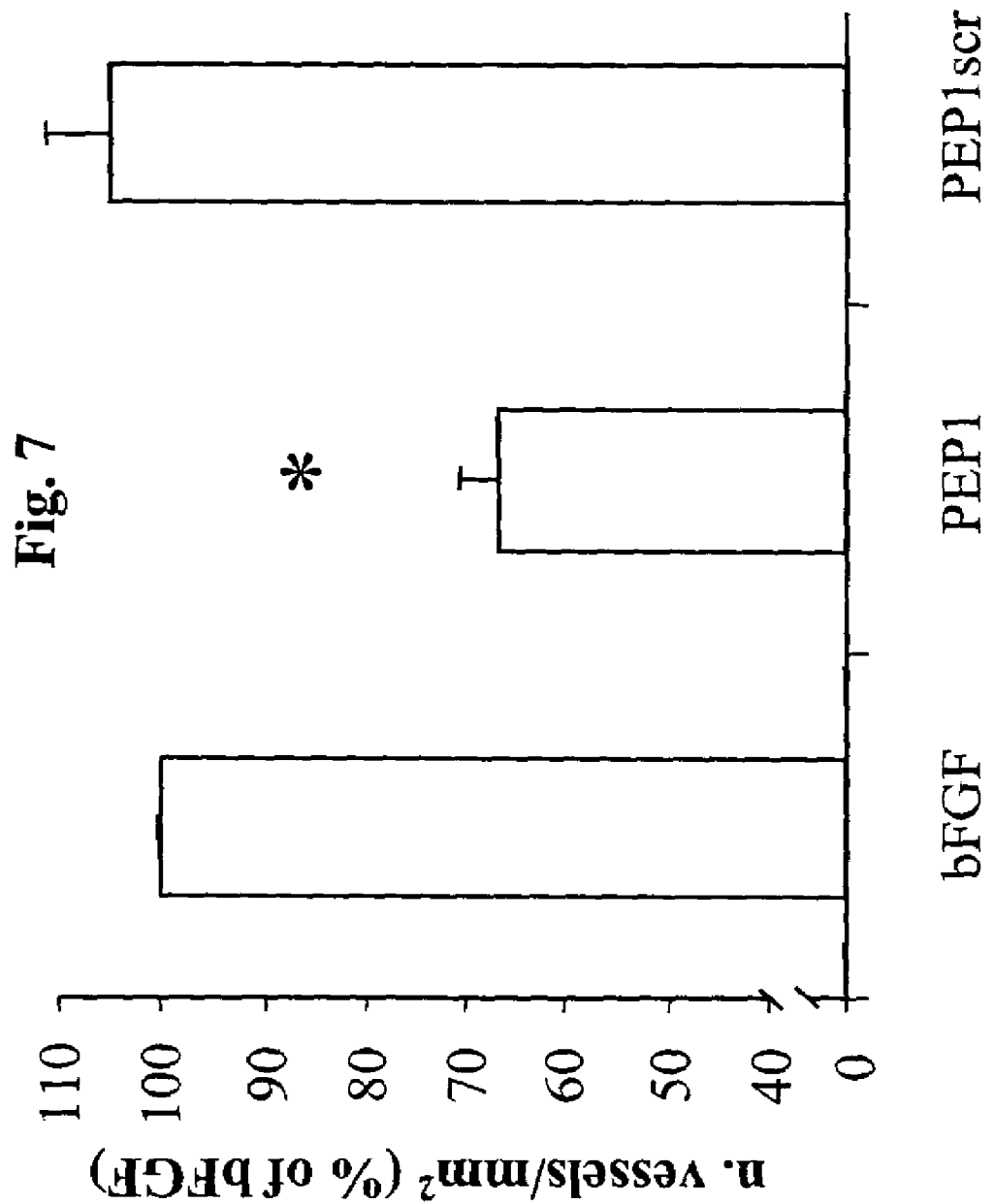
FIG. 7 shows PEP1 and PEP1scr effect on angiogenesis induced by bFGF in reconstituted basement membrane plugs, subcutaneusly injected in CD1 mice.

FIG. 7 shows that PEP1 acts as strong inhibitor of blood vessel formation induced by bFGF (i.e. 46% inhibition vs bFGF alone). 10 animals were used as control (treated with bFGF alone) and 14 animals were treated with bFGF in the presence of PEP1. This experiment shows that PEP1 is able to markedly inhibit new-blood vessel formation induced by bFGF and indicates PEP1 as a good candidate for further in vivo studies.

In conclusion:

1) PEP1 showed a strong and specific inhibitory activity on mitogenic and chemoattractive properties of platelet derived growth factor (PDGF-BB) and fibroblast growth factor (bFGF) in vitro.

2) Anti-angiogenic activity in vivo was demonstrated in assays carried out on reconstituted basement membrane plugs.

These results indicate PEP1 as a good candidate for further investigation on animal models of tumor growth and metastasis as well as other vascular-based diseases.

The invention claimed is:

1. An isolated peptide consisting of Asp-Pro-His-Ile-Lys-Leu-Gln-Leu-Gln-Ala-Glu (SEQ ID NO: 1).

\* \* \* \* \*

SEQUENCE LISTING

<160> NUMBER OF SEQ ID NOS: 86

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
aaagaataca ttaagtgcga tatt                                    24

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
caatccactt aatttttgtg ttattag                                 27

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
ttgttagcag gagcttatgc aatatc                                  26

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
gggcttgtaa gctctttaac tg                                      22

<210> SEQ ID NO 5
<211> LENGTH: 573
<212> TYPE: DNA
<213> ORGANISM: borrelia burgdorferi
<220> FEATURE:
<221> NAME/KEY: CDS
<222> LOCATION: (1)...(573)

<400> SEQUENCE: 5

| | | | | | | | | | | | | | | | | |
|---|---|---|---|---|---|---|---|---|---|---|---|---|---|---|---|---|
| atg | gct | tgt | aat | aat | tca | ggg | aaa | gat | ggg | aat | aca | tct | gca | aat | tct | 48 |
| Met | Ala | Cys | Asn | Asn | Ser | Gly | Lys | Asp | Gly | Asn | Thr | Ser | Ala | Asn | Ser | |
| 1 | | | | 5 | | | | | 10 | | | | | 15 | | |
| gct | gat | gag | tct | gtt | aaa | ggg | cct | aat | ctt | aca | gaa | ata | agt | aaa | aaa | 96 |
| Ala | Asp | Glu | Ser | Val | Lys | Gly | Pro | Asn | Leu | Thr | Glu | Ile | Ser | Lys | Lys | |
| | | | 20 | | | | | 25 | | | | | 30 | | | |
| att | acg | gat | tct | aat | gcg | gtt | tta | ctt | gct | gtg | aaa | gag | gtt | gaa | gcg | 144 |
| Ile | Thr | Asp | Ser | Asn | Ala | Val | Leu | Leu | Ala | Val | Lys | Glu | Val | Glu | Ala | |
| | | 35 | | | | | 40 | | | | | 45 | | | | |
| ttg | ctg | tca | tct | ata | gat | gag | ctt | gct | aaa | gct | att | ggt | aaa | aaa | ata | 192 |
| Leu | Leu | Ser | Ser | Ile | Asp | Glu | Leu | Ala | Lys | Ala | Ile | Gly | Lys | Lys | Ile | |
| | 50 | | | | | 55 | | | | | 60 | | | | | |
| aaa | aac | gat | ggt | agt | tta | gat | aat | gaa | gca | aat | cgc | aac | gag | tca | ttg | 240 |
| Lys | Asn | Asp | Gly | Ser | Leu | Asp | Asn | Glu | Ala | Asn | Arg | Asn | Glu | Ser | Leu | |
| 65 | | | | | 70 | | | | | 75 | | | | | 80 | |
| tta | gca | gga | gct | tat | aca | ata | tca | acc | tta | ata | aca | caa | aaa | tta | agt | 288 |
| Leu | Ala | Gly | Ala | Tyr | Thr | Ile | Ser | Thr | Leu | Ile | Thr | Gln | Lys | Leu | Ser | |
| | | | | 85 | | | | | 90 | | | | | 95 | | |
| aaa | tta | aac | gga | tca | gaa | ggt | tta | aag | gaa | aag | att | gcc | gca | gct | aag | 336 |
| Lys | Leu | Asn | Gly | Ser | Glu | Gly | Leu | Lys | Glu | Lys | Ile | Ala | Ala | Ala | Lys | |
| | | | 100 | | | | | 105 | | | | | 110 | | | |
| aaa | tgc | tct | gaa | gag | ttt | agt | act | aaa | cta | aaa | gat | aat | cat | gca | cag | 384 |
| Lys | Cys | Ser | Glu | Glu | Phe | Ser | Thr | Lys | Leu | Lys | Asp | Asn | His | Ala | Gln | |
| | | 115 | | | | | 120 | | | | | 125 | | | | |
| ctt | ggt | ata | cag | ggc | gtt | act | gat | gaa | aat | gca | aaa | aaa | gct | att | tta | 432 |
| Leu | Gly | Ile | Gln | Gly | Val | Thr | Asp | Glu | Asn | Ala | Lys | Lys | Ala | Ile | Leu | |
| | 130 | | | | | 135 | | | | | 140 | | | | | |
| aaa | gca | aat | gca | gcg | ggt | aaa | gat | aag | ggc | gtt | gaa | gaa | ctt | gaa | aag | 480 |
| Lys | Ala | Asn | Ala | Ala | Gly | Lys | Asp | Lys | Gly | Val | Glu | Glu | Leu | Glu | Lys | |
| 145 | | | | | 150 | | | | | 155 | | | | | 160 | |
| ttg | tcc | gga | tca | tta | gaa | agc | tta | tca | aaa | gca | gct | aaa | gag | atg | ctt | 528 |
| Leu | Ser | Gly | Ser | Leu | Glu | Ser | Leu | Ser | Lys | Ala | Ala | Lys | Glu | Met | Leu | |
| | | | | 165 | | | | | 170 | | | | | 175 | | |
| gct | aat | tca | gtt | aaa | gag | ctt | aca | agc | cct | gtt | gtc | cat | gga | tcc | | 573 |
| Ala | Asn | Ser | Val | Lys | Glu | Leu | Thr | Ser | Pro | Val | Val | His | Gly | Ser | | |
| | | | 180 | | | | | 185 | | | | | 190 | | | |

<210> SEQ ID NO 6
<211> LENGTH: 191
<212> TYPE: PRT
<213> ORGANISM: borrelia burgdorferi

<400> SEQUENCE: 6

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

```
Lys Asn Asp Gly Ser Leu Asp Asn Glu Ala Asn Arg Asn Glu Ser Leu
 65                  70                  75                  80

Leu Ala Gly Ala Tyr Thr Ile Ser Thr Leu Ile Thr Gln Lys Leu Ser
                 85                  90                  95

Lys Leu Asn Gly Ser Glu Gly Leu Lys Glu Lys Ile Ala Ala Ala Lys
            100                 105                 110

Lys Cys Ser Glu Glu Phe Ser Thr Lys Leu Lys Asp Asn His Ala Gln
        115                 120                 125

Leu Gly Ile Gln Gly Val Thr Asp Glu Asn Ala Lys Lys Ala Ile Leu
    130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Ser
            180                 185                 190
```

<210> SEQ ID NO 7
<211> LENGTH: 557
<212> TYPE: DNA
<213> ORGANISM: Borrelia burgdorferi
<220> FEATURE:
<221> NAME/KEY: CDS
<222> LOCATION: (3)...(557)

<400> SEQUENCE: 7

```
atg gct tgt aat aat tca gga aaa gat ggg aat gca tct gca aat tct      48
Met Ala Cys Asn Asn Ser Gly Lys Asp Gly Asn Ala Ser Ala Asn Ser
 1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
             20                  25                  30 att aca gaa tct aac gca gtt gtt ctg gcc gtg aaa gaa gtt gag acc     144
Ile Thr Glu Ser Asn Ala Val Val Leu Ala Val Lys Glu Val Glu Thr
         35                  40                  45 tta ctt gca tct ata gat gaa ctt gct acc aaa gct att ggt aaa aaa     192
Leu Leu Ala Ser Ile Asp Glu Leu Ala Thr Lys Ala Ile Gly Lys Lys
     50                  55                  60 ata ggc aat aat ggt tta gag gcc aat cag agt aaa aac aca tca ttg     240
Ile Gly Asn Asn Gly Leu Glu Ala Asn Gln Ser Lys Asn Thr Ser Leu
 65                  70                  75                  80 tta tca gga gct tat gca ata tct gac cta ata gca gaa aaa tta aat     288
Leu Ser Gly Ala Tyr Ala Ile Ser Asp Leu Ile Ala Glu Lys Leu Asn
                 85                  90                  95 gta ttg aaa aat gaa gaa tta aag gaa aag att gat aca gct aag caa     336
Val Leu Lys Asn Glu Glu Leu Lys Glu Lys Ile Asp Thr Ala Lys Gln
            100                 105                 110 tgt tct aca gaa ttt act aat aaa cta aaa agt gaa cat gca gtg ctt     384
Cys Ser Thr Glu Phe Thr Asn Lys Leu Lys Ser Glu His Ala Val Leu
        115                 120                 125 ggt ctg gac aat ctt act gat gat aat gca caa aga gct att tta aaa     432
Gly Leu Asp Asn Leu Thr Asp Asp Asn Ala Gln Arg Ala Ile Leu Lys
    130                 135                 140 aaa cat gca aat aaa gat aag ggt gct gca gaa ctt gaa aag tta ttt     480
Lys His Ala Asn Lys Asp Lys Gly Ala Ala Glu Leu Glu Lys Leu Phe
145                 150                 155                 160 aaa gcg gta gaa aac tta tca aaa gca gct caa gac aca tta aaa aat     528
Lys Ala Val Glu Asn Leu Ser Lys Ala Ala Gln Asp Thr Leu Lys Asn
                165                 170                 175
```

```
gct gtt aaa gag ctt aca agt cct att gt                                    557
Ala Val Lys Glu Leu Thr Ser Pro Ile
        180                 185

<210> SEQ ID NO 8
<211> LENGTH: 185
<212> TYPE: PRT
<213> ORGANISM: Borrelia burgdorferi

<400> SEQUENCE: 8

Met Ala Cys Asn Asn Ser Gly Lys Asp Gly Asn Ala Ser Ala Asn Ser
 1               5                  10                  15

Ala Asp Glu Ser Val Lys Gly Pro Asn Leu Thr Glu Ile Ser Lys Lys
            20                  25                  30

Ile Thr Glu Ser Asn Ala Val Leu Ala Val Lys Glu Val Glu Thr
        35                  40                  45

Leu Leu Ala Ser Ile Asp Glu Leu Ala Thr Lys Ala Ile Gly Lys Lys
    50                  55                  60

Ile Gly Asn Asn Gly Leu Glu Ala Asn Gln Ser Lys Asn Thr Ser Leu
65                  70                  75                  80

Leu Ser Gly Ala Tyr Ala Ile Ser Asp Leu Ile Ala Glu Lys Leu Asn
                85                  90                  95

Val Leu Lys Asn Glu Glu Leu Lys Glu Lys Ile Asp Thr Ala Lys Gln
            100                 105                 110

Cys Ser Thr Glu Phe Thr Asn Lys Leu Lys Ser Glu His Ala Val Leu
        115                 120                 125

Gly Leu Asp Asn Leu Thr Asp Asp Asn Ala Gln Arg Ala Ile Leu Lys
    130                 135                 140

Lys His Ala Asn Lys Asp Lys Gly Ala Ala Glu Leu Glu Lys Leu Phe
145                 150                 155                 160

Lys Ala Val Glu Asn Leu Ser Lys Ala Ala Gln Asp Thr Leu Lys Asn
                165                 170                 175

Ala Val Lys Glu Leu Thr Ser Pro Ile
        180                 185

<210> SEQ ID NO 9
<211> LENGTH: 579
<212> TYPE: DNA
<213> ORGANISM: Borrelia burgdorferi
<220> FEATURE:
<221> NAME/KEY: CDS
<222> LOCATION: (1)...(579)

<400> SEQUENCE: 9 atg act tta ttt tta ttt ata tct tgt aat aat tca ggg aaa gat ggg        48
Met Thr Leu Phe Leu Phe Ile Ser Cys Asn Asn Ser Gly Lys Asp Gly
 1               5                  10                  15 aat aca tct gca aat tct gct gat gag tct gtt aaa ggg cct aat ctt        96
Asn Thr Ser Ala Asn Ser Ala Asp Glu Ser Val Lys Gly Pro Asn Leu
            20                  25                  30 aca gaa ata agt aaa aaa att acg gat tct aat gcg gtt tta ctt gct       144
Thr Glu Ile Ser Lys Lys Ile Thr Asp Ser Asn Ala Val Leu Leu Ala
        35                  40                  45 gtg aaa gag gtt gaa gcg ttg ctg tca tct ata gat gaa att gct gct       192
Val Lys Glu Val Glu Ala Leu Leu Ser Ser Ile Asp Glu Ile Ala Ala
    50                  55                  60 aaa gct att ggt aaa aaa ata cac caa aat aat ggt ttg gat acc gaa       240
Lys Ala Ile Gly Lys Lys Ile His Gln Asn Asn Gly Leu Asp Thr Glu
65                  70                  75                  80
```

```
aat aat cac aat gga tca ttg tta gcg gga gct tat gca ata tca acc      288
Asn Asn His Asn Gly Ser Leu Leu Ala Gly Ala Tyr Ala Ile Ser Thr
                 85                  90                  95 cta ata aaa caa aaa tta gat gga ttg aaa aat gaa gga tta aag gaa      336
Leu Ile Lys Gln Lys Leu Asp Gly Leu Lys Asn Glu Gly Leu Lys Glu
            100                 105                 110 aaa att gat gcg gct aag aaa tgt tct gaa aca ttt act aat aaa tta      384
Lys Ile Asp Ala Ala Lys Lys Cys Ser Glu Thr Phe Thr Asn Lys Leu
                115                 120                 125 aaa gaa aaa cac aca gat ctt ggt aaa gaa ggt gtt act gat gct gat      432
Lys Glu Lys His Thr Asp Leu Gly Lys Glu Gly Val Thr Asp Ala Asp
    130                 135                 140 gca aaa gaa gcc att tta aaa aca aat ggt act aaa act aaa ggt gct      480
Ala Lys Glu Ala Ile Leu Lys Thr Asn Gly Thr Lys Thr Lys Gly Ala
145                 150                 155                 160 gaa gaa ctt gga aaa tta ttt gaa tca gta gag gtc ttg tca aaa gca      528
Glu Glu Leu Gly Lys Leu Phe Glu Ser Val Glu Val Leu Ser Lys Ala
                165                 170                 175 gct aaa gag atg ctt gct aat tca gtt aaa gag ctt aca agc cct gtt      576
Ala Lys Glu Met Leu Ala Asn Ser Val Lys Glu Leu Thr Ser Pro Val
            180                 185                 190 gtg                                                                  579
Val

<210> SEQ ID NO 10
<211> LENGTH: 193
<212> TYPE: PRT
<213> ORGANISM: Borrelia burgdorferi

<400> SEQUENCE: 10

Met Thr Leu Phe Leu Phe Ile Ser Cys Asn Asn Ser Gly Lys Asp Gly
 1               5                  10                  15

Asn Thr Ser Ala Asn Ser Ala Asp Glu Ser Val Lys Gly Pro Asn Leu
            20                  25                  30

Thr Glu Ile Ser Lys Lys Ile Thr Asp Ser Asn Ala Val Leu Leu Ala
        35                  40                  45

Val Lys Glu Val Glu Ala Leu Leu Ser Ser Ile Asp Glu Ile Ala Ala
 50                  55                  60

Lys Ala Ile Gly Lys Lys Ile His Gln Asn Asn Gly Leu Asp Thr Glu
 65                  70                  75                  80

Asn Asn His Asn Gly Ser Leu Leu Ala Gly Ala Tyr Ala Ile Ser Thr
                 85                  90                  95

Leu Ile Lys Gln Lys Leu Asp Gly Leu Lys Asn Glu Gly Leu Lys Glu
            100                 105                 110

Lys Ile Asp Ala Ala Lys Lys Cys Ser Glu Thr Phe Thr Asn Lys Leu
        115                 120                 125

Lys Glu Lys His Thr Asp Leu Gly Lys Glu Gly Val Thr Asp Ala Asp
    130                 135                 140

Ala Lys Glu Ala Ile Leu Lys Thr Asn Gly Thr Lys Thr Lys Gly Ala
145                 150                 155                 160

Glu Glu Leu Gly Lys Leu Phe Glu Ser Val Glu Val Leu Ser Lys Ala
                165                 170                 175

Ala Lys Glu Met Leu Ala Asn Ser Val Lys Glu Leu Thr Ser Pro Val
            180                 185                 190

Val
```

-continued

```
<210> SEQ ID NO 11
<211> LENGTH: 582
<212> TYPE: DNA
<213> ORGANISM: Borrelia brgdorferi
<220> FEATURE:
<221> NAME/KEY: CDS
<222> LOCATION: (1)...(582)

<400> SEQUENCE: 11 atg act tta ttt tta ttt ata tct tgt aat aat tca ggg aaa gat ggg      48
Met Thr Leu Phe Leu Phe Ile Ser Cys Asn Asn Ser Gly Lys Asp Gly
 1               5                  10                  15 aat aca tct gca aat tct gct gat gag tct gtt aaa ggg cct aat ctt      96
Asn Thr Ser Ala Asn Ser Ala Asp Glu Ser Val Lys Gly Pro Asn Leu
                20                  25                  30 aca gaa ata agt aaa aaa att acg gat tct aat gcg gtt tta ctt gct     144
Thr Glu Ile Ser Lys Lys Ile Thr Asp Ser Asn Ala Val Leu Leu Ala
            35                  40                  45 gtg aaa gag gtt gaa gcg ttg ctg tca tct ata gat gag ctt gct aaa     192
Val Lys Glu Val Glu Ala Leu Leu Ser Ser Ile Asp Glu Leu Ala Lys
 50                  55                  60 gct att ggt aaa aaa ata aaa aac gat ggt agt tta gat aat gaa gca     240
Ala Ile Gly Lys Lys Ile Lys Asn Asp Gly Ser Leu Asp Asn Glu Ala
 65                  70                  75                  80 aat cgc aac gag tca ttg tta gca gga gct tat aca ata tca acc tta     288
Asn Arg Asn Glu Ser Leu Leu Ala Gly Ala Tyr Thr Ile Ser Thr Leu
                85                  90                  95 ata aca caa aaa tta agt aaa tta aac gga tca gaa ggt tta aag gaa     336
Ile Thr Gln Lys Leu Ser Lys Leu Asn Gly Ser Glu Gly Leu Lys Glu
            100                 105                 110 aag att gcc gca gct aag aaa tgc tct gaa gag ttt agt act aaa cta     384
Lys Ile Ala Ala Ala Lys Lys Cys Ser Glu Glu Phe Ser Thr Lys Leu
        115                 120                 125 aaa gat aat cat gca cag ctt ggt ata cag ggc gtt act gat gaa aat     432
Lys Asp Asn His Ala Gln Leu Gly Ile Gln Gly Val Thr Asp Glu Asn
    130                 135                 140 gca aaa aaa gct att tta aaa gca aat gca gcg ggt aaa gat aag ggc     480
Ala Lys Lys Ala Ile Leu Lys Ala Asn Ala Ala Gly Lys Asp Lys Gly
145                 150                 155                 160 gtt gaa gaa ctt gaa aag ttg tcc gga tca tta gaa agc tta tca aaa     528
Val Glu Glu Leu Glu Lys Leu Ser Gly Ser Leu Glu Ser Leu Ser Lys
                165                 170                 175 gca gct aaa gag atg ctt gct aat tca gtt aaa gag ctt aca agc cct     576
Ala Ala Lys Glu Met Leu Ala Asn Ser Val Lys Glu Leu Thr Ser Pro
            180                 185                 190 gtt gtg                                                             582
Val Val

<210> SEQ ID NO 12
<211> LENGTH: 194
<212> TYPE: PRT
<213> ORGANISM: Borrelia brgdorferi

<400> SEQUENCE: 12

Met Thr Leu Phe Leu Phe Ile Ser Cys Asn Asn Ser Gly Lys Asp Gly
 1               5                  10                  15

Asn Thr Ser Ala Asn Ser Ala Asp Glu Ser Val Lys Gly Pro Asn Leu
                20                  25                  30

Thr Glu Ile Ser Lys Lys Ile Thr Asp Ser Asn Ala Val Leu Leu Ala
            35                  40                  45

Val Lys Glu Val Glu Ala Leu Leu Ser Ser Ile Asp Glu Leu Ala Lys
```

```
                50              55              60
Ala Ile Gly Lys Lys Ile Lys Asn Asp Gly Ser Leu Asp Asn Glu Ala
 65                  70                  75                  80

Asn Arg Asn Glu Ser Leu Leu Ala Gly Ala Tyr Thr Ile Ser Thr Leu
                 85                  90                  95

Ile Thr Gln Lys Leu Ser Lys Leu Asn Gly Ser Glu Gly Leu Lys Glu
            100                 105                 110

Lys Ile Ala Ala Lys Lys Cys Ser Glu Glu Phe Ser Thr Lys Leu
            115                 120                 125

Lys Asp Asn His Ala Gln Leu Gly Ile Gln Gly Val Thr Asp Glu Asn
        130                 135                 140

Ala Lys Lys Ala Ile Leu Lys Ala Asn Ala Gly Lys Asp Lys Gly
145                 150                 155                 160

Val Glu Glu Leu Glu Lys Leu Ser Gly Ser Leu Glu Ser Leu Ser Lys
                165                 170                 175

Ala Ala Lys Glu Met Leu Ala Asn Ser Val Lys Glu Leu Thr Ser Pro
            180                 185                 190

Val Val

<210> SEQ ID NO 13
<211> LENGTH: 576
<212> TYPE: DNA
<213> ORGANISM: Borrelia burgdorferi
<220> FEATURE:
<221> NAME/KEY: CDS
<222> LOCATION: (1)...(576)

<400> SEQUENCE: 13 atg act tta ttt tta ttt ata tct tgt aat aat tca gga aaa gat ggg      48
Met Thr Leu Phe Leu Phe Ile Ser Cys Asn Asn Ser Gly Lys Asp Gly
 1               5                  10                  15 aat gca tct gca aat tct gct gat gag tct gtt aaa ggg cct aat ctt      96
Asn Ala Ser Ala Asn Ser Ala Asp Glu Ser Val Lys Gly Pro Asn Leu
                20                  25                  30 aca gaa ata agt aaa aaa att aca gaa tct aac gca gtt gtt ctg gcc     144
Thr Glu Ile Ser Lys Lys Ile Thr Glu Ser Asn Ala Val Val Leu Ala
            35                  40                  45 gtg aaa gaa gtt gag acc tta ctt gca tct ata gat gaa ctt gct acc     192
Val Lys Glu Val Glu Thr Leu Leu Ala Ser Ile Asp Glu Leu Ala Thr
 50                  55                  60 aaa gct att ggt aaa aaa ata ggc aat aat ggt tta gag gcc aat cag     240
Lys Ala Ile Gly Lys Lys Ile Gly Asn Asn Gly Leu Glu Ala Asn Gln
 65                  70                  75                  80 agt aaa aac aca tca ttg tta tca gga gct tat gca ata tct gac cta     288
Ser Lys Asn Thr Ser Leu Leu Ser Gly Ala Tyr Ala Ile Ser Asp Leu
                85                  90                  95 ata gca gaa aaa tta aat gta ttg aaa aat gaa gaa tta aag gaa aag     336
Ile Ala Glu Lys Leu Asn Val Leu Lys Asn Glu Glu Leu Lys Glu Lys
            100                 105                 110 att gat aca gct aag caa tgt tct aca gaa ttt act aat aaa cta aaa     384
Ile Asp Thr Ala Lys Gln Cys Ser Thr Glu Phe Thr Asn Lys Leu Lys
            115                 120                 125 agt gaa cat gca gtg ctt ggt ctg gac aat ctt act gat gat aat gca     432
Ser Glu His Ala Val Leu Gly Leu Asp Asn Leu Thr Asp Asp Asn Ala
        130                 135                 140 caa aga gct att tta aaa aaa cat gca aat aaa gat aag ggt gct gca     480
Gln Arg Ala Ile Leu Lys Lys His Ala Asn Lys Asp Lys Gly Ala Ala
145                 150                 155                 160
```

```
gaa ctt gaa aag tta ttt aaa gcg gta gaa aac tta tca aaa gca gct    528
Glu Leu Glu Lys Leu Phe Lys Ala Val Glu Asn Leu Ser Lys Ala Ala
            165                 170                 175 caa gac aca tta aaa aat gct gtt aaa gag ctt aca agt cct att gtg    576
Gln Asp Thr Leu Lys Asn Ala Val Lys Glu Leu Thr Ser Pro Ile Val
            180                 185                 190

<210> SEQ ID NO 14
<211> LENGTH: 192
<212> TYPE: PRT
<213> ORGANISM: Borrelia burgdorferi

<400> SEQUENCE: 14

Met Thr Leu Phe Leu Phe Ile Ser Cys Asn Asn Ser Gly Lys Asp Gly
 1               5                  10                  15

Asn Ala Ser Ala Asn Ser Ala Asp Glu Ser Val Lys Gly Pro Asn Leu
            20                  25                  30

Thr Glu Ile Ser Lys Lys Ile Thr Glu Ser Asn Ala Val Val Leu Ala
        35                  40                  45

Val Lys Glu Val Glu Thr Leu Leu Ala Ser Ile Asp Glu Leu Ala Thr
 50                  55                  60

Lys Ala Ile Gly Lys Lys Ile Gly Asn Asn Gly Leu Glu Ala Asn Gln
65                  70                  75                  80

Ser Lys Asn Thr Ser Leu Leu Ser Gly Ala Tyr Ala Ile Ser Asp Leu
                85                  90                  95

Ile Ala Glu Lys Leu Asn Val Leu Lys Asn Glu Glu Leu Lys Glu Lys
            100                 105                 110

Ile Asp Thr Ala Lys Gln Cys Ser Thr Glu Phe Thr Asn Lys Leu Lys
        115                 120                 125

Ser Glu His Ala Val Leu Gly Leu Asp Asn Leu Thr Asp Asp Asn Ala
    130                 135                 140

Gln Arg Ala Ile Leu Lys Lys His Ala Asn Lys Asp Lys Gly Ala Ala
145                 150                 155                 160

Glu Leu Glu Lys Leu Phe Lys Ala Val Glu Asn Leu Ser Lys Ala Ala
                165                 170                 175

Gln Asp Thr Leu Lys Asn Ala Val Lys Glu Leu Thr Ser Pro Ile Val
            180                 185                 190

<210> SEQ ID NO 15
<211> LENGTH: 576
<212> TYPE: DNA
<213> ORGANISM: borrelia burgdorferi
<220> FEATURE:
<221> NAME/KEY: CDS
<222> LOCATION: (1)...(576)

<400> SEQUENCE: 15 atg act tta ttt tta ttt ata tct tgt aat aat tca aga aaa gat ggg     48
Met Thr Leu Phe Leu Phe Ile Ser Cys Asn Asn Ser Arg Lys Asp Gly
 1               5                  10                  15 aat gca tct aca aat tct gcc gat gag tct gtt aaa ggg cct aat ctt     96
Asn Ala Ser Thr Asn Ser Ala Asp Glu Ser Val Lys Gly Pro Asn Leu
            20                  25                  30 aca gaa ata agt aaa aaa att aca gaa tct aac gca gtt gtt ctg gcc    144
Thr Glu Ile Ser Lys Lys Ile Thr Glu Ser Asn Ala Val Val Leu Ala
        35                  40                  45 gtg aaa gaa gtt gag acc tta ctt gca tct ata gat gaa ctt gct acc    192
Val Lys Glu Val Glu Thr Leu Leu Ala Ser Ile Asp Glu Leu Ala Thr
 50                  55                  60
```

-continued

```
aaa gct att ggt aag aaa ata ggc aat aat ggt tta gag gcc aat cag      240
Lys Ala Ile Gly Lys Lys Ile Gly Asn Asn Gly Leu Glu Ala Asn Gln
 65                  70                  75                  80 agt aaa aac aca tca ttg tta tca gga gct tat gca ata tct gac cta      288
Ser Lys Asn Thr Ser Leu Leu Ser Gly Ala Tyr Ala Ile Ser Asp Leu
                 85                  90                  95 ata gca gaa aaa tta aat gta ttg aaa aat gaa gaa tta aag gaa aag      336
Ile Ala Glu Lys Leu Asn Val Leu Lys Asn Glu Glu Leu Lys Glu Lys
            100                 105                 110 att gat aca gct aag caa tgt tct aca gaa ttt act aat aaa cta aaa      384
Ile Asp Thr Ala Lys Gln Cys Ser Thr Glu Phe Thr Asn Lys Leu Lys
        115                 120                 125 agt gaa cat gca gtg ctt ggt ctg gac aat ctt act gat gat aat gca      432
Ser Glu His Ala Val Leu Gly Leu Asp Asn Leu Thr Asp Asp Asn Ala
    130                 135                 140 caa aga gct att tta aaa aaa cat gca aat aaa gat aag ggt gct gca      480
Gln Arg Ala Ile Leu Lys Lys His Ala Asn Lys Asp Lys Gly Ala Ala
145                 150                 155                 160 gaa ctt gaa aag tta ttt aaa gcg gta gaa aac tta tca aaa gca gct      528
Glu Leu Glu Lys Leu Phe Lys Ala Val Glu Asn Leu Ser Lys Ala Ala
                165                 170                 175 caa gac aca tta aaa aat gct gtt aaa gag ctt aca agt cct att gtg      576
Gln Asp Thr Leu Lys Asn Ala Val Lys Glu Leu Thr Ser Pro Ile Val
            180                 185                 190
```

<210> SEQ ID NO 16
<211> LENGTH: 192
<212> TYPE: PRT
<213> ORGANISM: borrelia burgdorferi

<400> SEQUENCE: 16

```
Met Thr Leu Phe Leu Phe Ile Ser Cys Asn Asn Ser Arg Lys Asp Gly
  1               5                  10                  15

Asn Ala Ser Thr Asn Ser Ala Asp Glu Ser Val Lys Gly Pro Asn Leu
             20                  25                  30

Thr Glu Ile Ser Lys Lys Ile Thr Glu Ser Asn Ala Val Val Leu Ala
         35                  40                  45

Val Lys Glu Val Glu Thr Leu Leu Ala Ser Ile Asp Glu Leu Ala Thr
     50                  55                  60

Lys Ala Ile Gly Lys Lys Ile Gly Asn Asn Gly Leu Glu Ala Asn Gln
 65                  70                  75                  80

Ser Lys Asn Thr Ser Leu Leu Ser Gly Ala Tyr Ala Ile Ser Asp Leu
                 85                  90                  95

Ile Ala Glu Lys Leu Asn Val Leu Lys Asn Glu Glu Leu Lys Glu Lys
            100                 105                 110

Ile Asp Thr Ala Lys Gln Cys Ser Thr Glu Phe Thr Asn Lys Leu Lys
        115                 120                 125

Ser Glu His Ala Val Leu Gly Leu Asp Asn Leu Thr Asp Asp Asn Ala
    130                 135                 140

Gln Arg Ala Ile Leu Lys Lys His Ala Asn Lys Asp Lys Gly Ala Ala
145                 150                 155                 160

Glu Leu Glu Lys Leu Phe Lys Ala Val Glu Asn Leu Ser Lys Ala Ala
                165                 170                 175

Gln Asp Thr Leu Lys Asn Ala Val Lys Glu Leu Thr Ser Pro Ile Val
            180                 185                 190
```

<210> SEQ ID NO 17
<211> LENGTH: 573

```
<212> TYPE: DNA
<213> ORGANISM: Borrelia burgdorferi
<220> FEATURE:
<221> NAME/KEY: CDS
<222> LOCATION: (1)...(573)

<400> SEQUENCE: 17 atg act tta ttt tta ttt ata tct tgt aat aat tca ggg aaa gat ggg     48
Met Thr Leu Phe Leu Phe Ile Ser Cys Asn Asn Ser Gly Lys Asp Gly
 1               5                  10                  15 aat aca tct gca aat tct gct gat gag tct gtt aaa ggg cct aat ctt     96
Asn Thr Ser Ala Asn Ser Ala Asp Glu Ser Val Lys Gly Pro Asn Leu
            20                  25                  30 aca gaa ata agt aaa aaa att aca gaa tct aac gca gtt gtt ctc gcc    144
Thr Glu Ile Ser Lys Lys Ile Thr Glu Ser Asn Ala Val Val Leu Ala
        35                  40                  45 gtg aaa gaa gtt gaa act ttg ctt aca tct ata gat gag ctt gct aaa    192
Val Lys Glu Val Glu Thr Leu Leu Thr Ser Ile Asp Glu Leu Ala Lys
 50                  55                  60 gct att ggt aaa aaa ata aaa aac gat gtt agt tta gat aat gag gca    240
Ala Ile Gly Lys Lys Ile Lys Asn Asp Val Ser Leu Asp Asn Glu Ala
 65                  70                  75                  80 gat cac aac gga tca tta ata tca gga gca tat tta att tca aac tta    288
Asp His Asn Gly Ser Leu Ile Ser Gly Ala Tyr Leu Ile Ser Asn Leu
                85                  90                  95 ata aca aaa aaa ata agt gca ata aaa gat tca gga gaa ttg aag gca    336
Ile Thr Lys Lys Ile Ser Ala Ile Lys Asp Ser Gly Glu Leu Lys Ala
            100                 105                 110 gaa att gaa aag gct aag aaa tgt tct gaa gaa ttt act gct aaa tta    384
Glu Ile Glu Lys Ala Lys Lys Cys Ser Glu Glu Phe Thr Ala Lys Leu
        115                 120                 125 aaa ggt gaa cac aca gat ctt ggt aaa gaa ggc gtt act gat gat aat    432
Lys Gly Glu His Thr Asp Leu Gly Lys Glu Gly Val Thr Asp Asp Asn
    130                 135                 140 gca aaa aaa gcc att tta aaa aca aat aat gat aaa act aag ggc gct    480
Ala Lys Lys Ala Ile Leu Lys Thr Asn Asn Asp Lys Thr Lys Gly Ala
145                 150                 155                 160 gat gaa ctt gaa aag tta ttt gaa tca gta aaa aac ttg tca aaa gca    528
Asp Glu Leu Glu Lys Leu Phe Glu Ser Val Lys Asn Leu Ser Lys Ala
                165                 170                 175 gct aaa gag atg ctt act aat tca gtt aaa gag ctt aca agc cct        573
Ala Lys Glu Met Leu Thr Asn Ser Val Lys Glu Leu Thr Ser Pro
            180                 185                 190

<210> SEQ ID NO 18
<211> LENGTH: 191
<212> TYPE: PRT
<213> ORGANISM: Borrelia burgdorferi

<400> SEQUENCE: 18

Met Thr Leu Phe Leu Phe Ile Ser Cys Asn Asn Ser Gly Lys Asp Gly
 1               5                  10                  15

Asn Thr Ser Ala Asn Ser Ala Asp Glu Ser Val Lys Gly Pro Asn Leu
            20                  25                  30

Thr Glu Ile Ser Lys Lys Ile Thr Glu Ser Asn Ala Val Val Leu Ala
        35                  40                  45

Val Lys Glu Val Glu Thr Leu Leu Thr Ser Ile Asp Glu Leu Ala Lys
 50                  55                  60

Ala Ile Gly Lys Lys Ile Lys Asn Asp Val Ser Leu Asp Asn Glu Ala
65                  70                  75                  80
```

-continued

```
Asp His Asn Gly Ser Leu Ile Ser Gly Ala Tyr Leu Ile Ser Asn Leu
            85                  90                  95

Ile Thr Lys Lys Ile Ser Ala Ile Lys Asp Ser Gly Glu Leu Lys Ala
        100                 105                 110

Glu Ile Glu Lys Ala Lys Lys Cys Ser Glu Glu Phe Thr Ala Lys Leu
    115                 120                 125

Lys Gly Glu His Thr Asp Leu Gly Lys Glu Gly Val Thr Asp Asp Asn
130                 135                 140

Ala Lys Lys Ala Ile Leu Lys Thr Asn Asn Asp Lys Thr Lys Gly Ala
145                 150                 155                 160

Asp Glu Leu Glu Lys Leu Phe Glu Ser Val Lys Asn Leu Ser Lys Ala
                165                 170                 175

Ala Lys Glu Met Leu Thr Asn Ser Val Lys Glu Leu Thr Ser Pro
            180                 185                 190

<210> SEQ ID NO 19
<211> LENGTH: 553
<212> TYPE: DNA
<213> ORGANISM: Borrelia burgdorferi
<220> FEATURE:
<221> NAME/KEY: CDS
<222> LOCATION: (1)...(553)

<400> SEQUENCE: 19 atg act tta ttt tta ttt ata tct tgt aat aat tca gga aaa gat ggg      48
Met Thr Leu Phe Leu Phe Ile Ser Cys Asn Asn Ser Gly Lys Asp Gly
 1               5                  10                  15 aat aca tct gca aat tct gct gat gag tct gtt aaa ggg cct aat ctt      96
Asn Thr Ser Ala Asn Ser Ala Asp Glu Ser Val Lys Gly Pro Asn Leu
            20                  25                  30 aca gaa ata agt aaa aaa att aca gaa tct aac gca gtt gtt ctg gct     144
Thr Glu Ile Ser Lys Lys Ile Thr Glu Ser Asn Ala Val Val Leu Ala
        35                  40                  45 gtg aaa gaa att gaa act ttg ctt gca tct ata gat gaa ctt gct act     192
Val Lys Glu Ile Glu Thr Leu Leu Ala Ser Ile Asp Glu Leu Ala Thr
    50                  55                  60 aaa gct att ggt aaa aaa ata gat aac aat gct ggt ttg ggt gct gaa     240
Lys Ala Ile Gly Lys Lys Ile Asp Asn Asn Ala Gly Leu Gly Ala Glu
 65                  70                  75                  80 gtg ggt caa aac gga tca ttg cta gca gga gct tat gca atc tca act     288
Val Gly Gln Asn Gly Ser Leu Leu Ala Gly Ala Tyr Ala Ile Ser Thr
                85                  90                  95 gta ata ata gaa aaa ttg agc aca tta aaa aat gta gaa gaa tta aaa     336
Val Ile Ile Glu Lys Leu Ser Thr Leu Lys Asn Val Glu Glu Leu Lys
            100                 105                 110 gaa aaa att aca aag gct aag gat tgt tct gaa aaa ttc act aaa aaa     384
Glu Lys Ile Thr Lys Ala Lys Asp Cys Ser Glu Lys Phe Thr Lys Lys
        115                 120                 125 tta aaa gat agc cgc gca gag ctt ggt aaa aaa gat gcc agt gat gat     432
Leu Lys Asp Ser Arg Ala Glu Leu Gly Lys Lys Asp Ala Ser Asp Asp
130                 135                 140 gat gca aaa aaa gct att tta aaa aca aat caa gct aac gat aag ggt     480
Asp Ala Lys Lys Ala Ile Leu Lys Thr Asn Gln Ala Asn Asp Lys Gly
145                 150                 155                 160 gct aaa gaa ctt aaa gag tta ttt gaa gca gta gaa agc ttg tca aaa     528
Ala Lys Glu Leu Lys Glu Leu Phe Glu Ala Val Glu Ser Leu Ser Lys
                165                 170                 175 gcg gct aaa gag atg cta aac aag t                                    553
Ala Ala Lys Glu Met Leu Asn Lys
            180
```

<210> SEQ ID NO 20
<211> LENGTH: 184
<212> TYPE: PRT
<213> ORGANISM: Borrelia burgdorferi

<400> SEQUENCE: 20

```
Met Thr Leu Phe Leu Phe Ile Ser Cys Asn Asn Ser Gly Lys Asp Gly
 1               5                  10                  15

Asn Thr Ser Ala Asn Ser Ala Asp Glu Ser Val Lys Gly Pro Asn Leu
            20                  25                  30

Thr Glu Ile Ser Lys Lys Ile Thr Glu Ser Asn Ala Val Val Leu Ala
        35                  40                  45

Val Lys Glu Ile Glu Thr Leu Leu Ala Ser Ile Asp Glu Leu Ala Thr
    50                  55                  60

Lys Ala Ile Gly Lys Lys Ile Asp Asn Asn Ala Gly Leu Gly Ala Glu
65                  70                  75                  80

Val Gly Gln Asn Gly Ser Leu Leu Ala Gly Ala Tyr Ala Ile Ser Thr
                85                  90                  95

Val Ile Ile Glu Lys Leu Ser Thr Leu Lys Asn Val Glu Glu Leu Lys
            100                 105                 110

Glu Lys Ile Thr Lys Ala Lys Asp Cys Ser Glu Lys Phe Thr Lys Lys
        115                 120                 125

Leu Lys Asp Ser Arg Ala Glu Leu Gly Lys Lys Asp Ala Ser Asp Asp
    130                 135                 140

Asp Ala Lys Lys Ala Ile Leu Lys Thr Asn Gln Ala Asn Asp Lys Gly
145                 150                 155                 160

Ala Lys Glu Leu Lys Glu Leu Phe Glu Ala Val Glu Ser Leu Ser Lys
                165                 170                 175

Ala Ala Lys Glu Met Leu Asn Lys
            180
```

<210> SEQ ID NO 21
<211> LENGTH: 582
<212> TYPE: DNA
<213> ORGANISM: Borrelia burgdorferi
<220> FEATURE:
<221> NAME/KEY: CDS
<222> LOCATION: (1)...(582)

<400> SEQUENCE: 21

```
atg act tta ttt tta ttt ata tct tgt aat aat tca gga aaa gat ggg       48
Met Thr Leu Phe Leu Phe Ile Ser Cys Asn Asn Ser Gly Lys Asp Gly
 1               5                  10                  15 aat aca tct gca aat tct gct gat gag tct gtt aaa ggg cct aat ctt       96
Asn Thr Ser Ala Asn Ser Ala Asp Glu Ser Val Lys Gly Pro Asn Leu
            20                  25                  30 aca gaa ata agt aaa aaa att aca gaa tct aac gca gtt gtt ctg gct      144
Thr Glu Ile Ser Lys Lys Ile Thr Glu Ser Asn Ala Val Val Leu Ala
        35                  40                  45 gtg aaa gaa att gaa act ttg ctt gca tct ata gat gaa ctt gct act      192
Val Lys Glu Ile Glu Thr Leu Leu Ala Ser Ile Asp Glu Leu Ala Thr
    50                  55                  60 aaa gct att ggt aaa aaa ata caa caa aat ggt ggt tta gct gtc gaa      240
Lys Ala Ile Gly Lys Lys Ile Gln Gln Asn Gly Gly Leu Ala Val Glu
65                  70                  75                  80 gcg ggg cat aat gga aca ttg tta gca ggt gct tat aca ata tca aaa      288
Ala Gly His Asn Gly Thr Leu Leu Ala Gly Ala Tyr Thr Ile Ser Lys
                85                  90                  95
```

```
cta ata aca caa aaa tta gat gga ttg aaa aat tca gaa aaa tta aag      336
Leu Ile Thr Gln Lys Leu Asp Gly Leu Lys Asn Ser Glu Lys Leu Lys
            100                 105                 110 gaa aaa att gaa aat gct aag aaa tgt tct gaa gat ttt act aaa aaa      384
Glu Lys Ile Glu Asn Ala Lys Lys Cys Ser Glu Asp Phe Thr Lys Lys
        115                 120                 125 cta gaa gga gaa cat gcg caa ctt gga att gaa aat gtt act gat gag      432
Leu Glu Gly Glu His Ala Gln Leu Gly Ile Glu Asn Val Thr Asp Glu
    130                 135                 140 aat gca aaa aaa gct att tta ata aca gat gca gct aaa gat aag ggc      480
Asn Ala Lys Lys Ala Ile Leu Ile Thr Asp Ala Ala Lys Asp Lys Gly
145                 150                 155                 160 gct gca gag ctt gaa aag cta ttt aaa gca gta gaa aac ttg gca aaa      528
Ala Ala Glu Leu Glu Lys Leu Phe Lys Ala Val Glu Asn Leu Ala Lys
                165                 170                 175 gca gct aaa gag atg ctt gct aat tca gtt aaa gag ctt aca agt cct      576
Ala Ala Lys Glu Met Leu Ala Asn Ser Val Lys Glu Leu Thr Ser Pro
            180                 185                 190 att gtg                                                              582
Ile Val
```

<210> SEQ ID NO 22
<211> LENGTH: 194
<212> TYPE: PRT
<213> ORGANISM: Borrelia burgdorferi

<400> SEQUENCE: 22

```
Met Thr Leu Phe Leu Phe Ile Ser Cys Asn Asn Ser Gly Lys Asp Gly
  1               5                  10                  15

Asn Thr Ser Ala Asn Ser Ala Asp Glu Ser Val Lys Gly Pro Asn Leu
             20                  25                  30

Thr Glu Ile Ser Lys Lys Ile Thr Glu Ser Asn Ala Val Val Leu Ala
         35                  40                  45

Val Lys Glu Ile Glu Thr Leu Leu Ala Ser Ile Asp Glu Leu Ala Thr
     50                  55                  60

Lys Ala Ile Gly Lys Lys Ile Gln Gln Asn Gly Gly Leu Ala Val Glu
 65                  70                  75                  80

Ala Gly His Asn Gly Thr Leu Leu Ala Gly Ala Tyr Thr Ile Ser Lys
                 85                  90                  95

Leu Ile Thr Gln Lys Leu Asp Gly Leu Lys Asn Ser Glu Lys Leu Lys
            100                 105                 110

Glu Lys Ile Glu Asn Ala Lys Lys Cys Ser Glu Asp Phe Thr Lys Lys
        115                 120                 125

Leu Glu Gly Glu His Ala Gln Leu Gly Ile Glu Asn Val Thr Asp Glu
    130                 135                 140

Asn Ala Lys Lys Ala Ile Leu Ile Thr Asp Ala Ala Lys Asp Lys Gly
145                 150                 155                 160

Ala Ala Glu Leu Glu Lys Leu Phe Lys Ala Val Glu Asn Leu Ala Lys
                165                 170                 175

Ala Ala Lys Glu Met Leu Ala Asn Ser Val Lys Glu Leu Thr Ser Pro
            180                 185                 190

Ile Val
```

<210> SEQ ID NO 23
<211> LENGTH: 1128
<212> TYPE: DNA
<213> ORGANISM: Artificial Sequence

```
<220> FEATURE:
<223> OTHER INFORMATION: OspC Chimera
<220> FEATURE:
<221> NAME/KEY: CDS
<222> LOCATION: (1)...(1128)

<400> SEQUENCE: 23 atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
             20                  25                  30 att acg gat tct aat gcg gtt tta ctt gct gtg aaa gag gtt gaa gcg      144
Ile Thr Asp Ser Asn Ala Val Leu Leu Ala Val Lys Glu Val Glu Ala
         35                  40                  45 ttg ctg tca tct ata gat gaa att gct gct aaa gct att ggt aaa aaa      192
Leu Leu Ser Ser Ile Asp Glu Ile Ala Ala Lys Ala Ile Gly Lys Lys
     50                  55                  60 ata cac caa aat aat ggt ttg gat acc gaa tat aat cac aat gga tca      240
Ile His Gln Asn Asn Gly Leu Asp Thr Glu Tyr Asn His Asn Gly Ser
 65                  70                  75                  80 ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140 aaa aca aat ggt act aaa act aaa ggt gct gaa gaa ctt gga aaa tta      480
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca gcc      576
Asn Ser Val Lys Glu Leu Thr Ser Pro Val Val Ala Glu Ser Pro Ala
            180                 185                 190 atg gta aat aat tca ggg aaa gat ggg aat aca tct gca aat tct gct      624
Met Val Asn Asn Ser Gly Lys Asp Gly Asn Thr Ser Ala Asn Ser Ala
        195                 200                 205 gat gag tct gtt aaa ggg cct aat ctt aca gaa ata agt aaa aaa att      672
Asp Glu Ser Val Lys Gly Pro Asn Leu Thr Glu Ile Ser Lys Lys Ile
    210                 215                 220 aca gaa tct aac gca gtt gtt ctc gcc gtg aaa gaa gtt gaa act ttg      720
Thr Glu Ser Asn Ala Val Val Leu Ala Val Lys Glu Val Glu Thr Leu
225                 230                 235                 240 ctt aca tct ata gat gag ctt gct aaa gct att ggt aaa aaa ata aaa      768
Leu Thr Ser Ile Asp Glu Leu Ala Lys Ala Ile Gly Lys Lys Ile Lys
                245                 250                 255 aac gat gtt agt tta gat aat gag gca gat cac aac gga tca tta ata      816
Asn Asp Val Ser Leu Asp Asn Glu Ala Asp His Asn Gly Ser Leu Ile
            260                 265                 270 tca gga gca tat tta att tca aac tta ata aca aaa aaa ata agt gca      864
Ser Gly Ala Tyr Leu Ile Ser Asn Leu Ile Thr Lys Lys Ile Ser Ala
        275                 280                 285
```

```
ata aaa gat tca gga gaa ttg aag gca gaa att gaa aag gct aag aaa      912
Ile Lys Asp Ser Gly Glu Leu Lys Ala Glu Ile Glu Lys Ala Lys Lys
    290                 295                 300 tgt tct gaa gaa ttt act gct aaa tta aaa ggt gaa cac aca gat ctt      960
Cys Ser Glu Glu Phe Thr Ala Lys Leu Lys Gly Glu His Thr Asp Leu
305                 310                 315                 320 ggt aaa gaa ggc gtt act gat gat aat gca aaa aaa gcc att tta aaa     1008
Gly Lys Glu Gly Val Thr Asp Asp Asn Ala Lys Lys Ala Ile Leu Lys
                325                 330                 335 aca aat aat gat aaa act aag ggc gct gat gaa ctt gaa aag tta ttt     1056
Thr Asn Asn Asp Lys Thr Lys Gly Ala Asp Glu Leu Glu Lys Leu Phe
            340                 345                 350 gaa tca gta aaa aac ttg tca aaa gca gct aaa gag atg ctt act aat     1104
Glu Ser Val Lys Asn Leu Ser Lys Ala Ala Lys Glu Met Leu Thr Asn
        355                 360                 365 tca gtt aaa gag ctt aca agc taa                                     1128
Ser Val Lys Glu Leu Thr Ser  *
    370                 375
```

<210> SEQ ID NO 24
<211> LENGTH: 375
<212> TYPE: PRT
<213> ORGANISM: Artificial Sequence
<220> FEATURE:
<223> OTHER INFORMATION: OspC Chimera

<400> SEQUENCE: 24

```
Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile

```
Leu Thr Ser Ile Asp Glu Leu Ala Lys Ala Ile Gly Lys Lys Ile Lys
            245                 250                 255

Asn Asp Val Ser Leu Asp Asn Glu Ala Asp His Asn Gly Ser Leu Ile
        260                 265                 270

Ser Gly Ala Tyr Leu Ile Ser Asn Leu Ile Thr Lys Lys Ile Ser Ala
    275                 280                 285

Ile Lys Asp Ser Gly Glu Leu Lys Ala Glu Ile Glu Lys Ala Lys Lys
290                 295                 300

Cys Ser Glu Glu Phe Thr Ala Lys Leu Lys Gly Glu His Thr Asp Leu
305                 310                 315                 320

Gly Lys Glu Gly Val Thr Asp Asn Ala Lys Lys Ala Ile Leu Lys
                325                 330                 335

Thr Asn Asn Asp Lys Thr Lys Gly Ala Asp Glu Leu Glu Lys Leu Phe
            340                 345                 350

Glu Ser Val Lys Asn Leu Ser Lys Ala Ala Lys Glu Met Leu Thr Asn
        355                 360                 365

Ser Val Lys Glu Leu Thr Ser
    370                 375

<210> SEQ ID NO 25
<211> LENGTH: 1124
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1124)

<400> SEQUENCE: 25 atg gct tgt aat aat tca ggg aaa gat ggg aat aca tct gca aat tct      48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg     144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa     192
Leu Leu Ser Ser Ile Asp Glu Ile Ala Ala Lys Ala Ile Gly Lys Lys
    50                  55                  60 ata cac caa aat aat ggt ttg gat acc gaa tat aat cac aat gga tca     240
Ile His Gln Asn Asn Gly Leu Asp Thr Glu Tyr Asn His Asn Gly Ser
65                  70                  75                  80 ttg tta gcg gga gct tat gca ata tca acc cta ata aaa caa aaa tta     288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag     336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat     384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta     432
Leu Gly Lys Glu Gly Val Thr Asp Ala Asp Ala Lys Glu Ala Ile Leu
    130                 135                 140 aaa aca aat ggt act aaa act aaa ggt gct gaa gaa ctt gga aaa tta     480
Lys Thr Asn Gly Thr Lys Thr Lys Gly Ala Glu Glu Leu Gly Lys Leu
```

|  |  |  |  |  |  |  |  |  |  |  |  |  |  |  |  |
|---|---|---|---|---|---|---|---|---|---|---|---|---|---|---|---|

```
                    145                 150                 155                 160
ttt gaa tca gta gag gtc ttg tca aaa gca gct aaa gag atg ctt gct       528
Phe Glu Ser Val Glu Val Leu Ser Lys Ala Ala Lys Glu Met Leu Ala
            165                 170                 175 aat tca gtt aaa gag ctt aca agc cct gtt gtg gca gaa agt cca gcc       576
Asn Ser Val Lys Glu Leu Thr Ser Pro Val Val Ala Glu Ser Pro Ala
        180                 185                 190 atg gta aat aat tca gga aaa gat ggg aat aca tct gca aat tct gct       624
Met Val Asn Asn Ser Gly Lys Asp Gly Asn Thr Ser Ala Asn Ser Ala
    195                 200                 205 gat gag tct gtt aaa ggg cct aat ctt aca gaa ata agt aaa aaa att       672
Asp Glu Ser Val Lys Gly Pro Asn Leu Thr Glu Ile Ser Lys Lys Ile
210                 215                 220 aca gaa tct aac gca gtt gtt ctg gct gtg aaa gaa att gaa act ttg       720
Thr Glu Ser Asn Ala Val Val Leu Ala Val Lys Glu Ile Glu Thr Leu
225                 230                 235                 240 ctt gca tct ata gat gaa ctt gct act aaa gct att ggt aaa aaa ata       768
Leu Ala Ser Ile Asp Glu Leu Ala Thr Lys Ala Ile Gly Lys Lys Ile
            245                 250                 255 caa caa aat ggt ggt tta gct gtc gaa gcg ggg cat aat gga aca ttg       816
Gln Gln Asn Gly Gly Leu Ala Val Glu Ala Gly His Asn Gly Thr Leu
        260                 265                 270 tta gca ggt gct tat aca ata tca aaa cta ata aca caa aaa tta gat       864
Leu Ala Gly Ala Tyr Thr Ile Ser Lys Leu Ile Thr Gln Lys Leu Asp
    275                 280                 285 gga ttg aaa aat tca gaa aaa tta aag gaa aaa att gaa aat gct aag       912
Gly Leu Lys Asn Ser Glu Lys Leu Lys Glu Lys Ile Glu Asn Ala Lys
290                 295                 300 aaa tgt tct gaa gat ttt act aaa aaa cta gaa gga gaa cat gcg caa       960
Lys Cys Ser Glu Asp Phe Thr Lys Lys Leu Glu Gly Glu His Ala Gln
305                 310                 315                 320 ctt gga att gaa aat gtt act gat gag aat gca aaa aaa gct att tta      1008
Leu Gly Ile Glu Asn Val Thr Asp Glu Asn Ala Lys Lys Ala Ile Leu
            325                 330                 335 ata aca gat gca gct aaa gat aag ggc gct gca gag ctt gaa aag cta      1056
Ile Thr Asp Ala Ala Lys Asp Lys Gly Ala Ala Glu Leu Glu Lys Leu
        340                 345                 350 ttt aaa gca gta gaa aac ttg gca aaa gca gct aaa gag atg ctt gct      1104
Phe Lys Ala Val Glu Asn Leu Ala Lys Ala Ala Lys Glu Met Leu Ala
    355                 360                 365 aat tca gtt aaa gag ctt ac                                           1124
Asn Ser Val Lys Glu Leu
        370

<210> SEQ ID NO 26
<211> LENGTH: 374
<212> TYPE: PRT
<213> ORGANISM: Artificial Sequence
<220> FEATURE:
<223> OTHER INFORMATION: OspC Chimera

<400> SEQUENCE: 26

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu

```
Ile His Gln Asn Asn Gly Leu Asp Thr Glu Tyr Asn His Asn Gly Ser
 65                  70                  75                  80

Leu Leu Ala Gly Ala Tyr Ala Ile Ser Thr Leu Ile Lys Gln Lys Leu
                 85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Thr Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Ala
            180                 185                 190

Met Val Asn Asn Ser Gly Lys Asp Gly Asn Thr Ser Ala Asn Ser Ala
        195                 200                 205

Asp Glu Ser Val Lys Gly Pro Asn Leu Thr Glu Ile Ser Lys Lys Ile
    210                 215                 220

Thr Glu Ser Asn Ala Val Val Leu Ala Val Lys Glu Ile Glu Thr Leu
225                 230                 235                 240

Leu Ala Ser Ile Asp Glu Leu Ala Thr Lys Ala Ile Gly Lys Lys Ile
                245                 250                 255

Gln Gln Asn Gly Gly Leu Ala Val Glu Ala Gly His Asn Gly Thr Leu
            260                 265                 270

Leu Ala Gly Ala Tyr Thr Ile Ser Lys Leu Ile Thr Gln Lys Leu Asp
        275                 280                 285

Gly Leu Lys Asn Ser Glu Lys Leu Lys Glu Lys Ile Glu Asn Ala Lys
    290                 295                 300

Lys Cys Ser Glu Asp Phe Thr Lys Lys Leu Glu Gly Glu His Ala Gln
305                 310                 315                 320

Leu Gly Ile Glu Asn Val Thr Asp Glu Asn Ala Lys Lys Ala Ile Leu
                325                 330                 335

Ile Thr Asp Ala Ala Lys Asp Lys Gly Ala Ala Glu Leu Glu Lys Leu
            340                 345                 350

Phe Lys Ala Val Glu Asn Leu Ala Lys Ala Ala Lys Glu Met Leu Ala
        355                 360                 365

Asn Ser Val Lys Glu Leu
    370

<210> SEQ ID NO 27
<211> LENGTH: 1137
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1137)

<400> SEQUENCE: 27 atg gct tgt aat aat tca ggg aaa gat ggg aat aca tct gca aat tct      48
Met Ala Cys Asn Asn Ser Gly Lys Asp Gly Asn Thr Ser Ala Asn Ser
  1               5                  10                  15 gct gat gag tct gtt aaa ggg cct aat ctt aca gaa ata aat aaa aaa      96
```

-continued

```
Ala Asp Glu Ser Val Lys Gly Pro Asn Leu Thr Glu Ile Asn Lys Lys
         20                  25                  30 att acg gat tct aat gcg gtt tta ctt gct gtg aaa gag gtt gaa gcg      144
Ile Thr Asp Ser Asn Ala Val Leu Leu Ala Val Lys Glu Val Glu Ala
             35                  40                  45 ttg ctg tca tct ata gat gaa att gct gct aaa gct att ggt aaa aaa      192
Leu Leu Ser Ser Ile Asp Glu Ile Ala Ala Lys Ala Ile Gly Lys Lys
 50                  55                  60 ata cac caa aat aat ggt ttg gat acc gaa aat aat cac aat gga tca      240
Ile His Gln Asn Asn Gly Leu Asp Thr Glu Asn Asn His Asn Gly Ser
 65                  70                  75                  80 ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
130                 135                 140 aaa gca aat ggt act aaa act aaa ggt gct gaa gaa ctt gga aaa tta      480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175 aat tca gtt aaa gag ctt aca agc cct gtg gtg gca gaa agt cca aaa      576
Asn Ser Val Lys Glu Leu Thr Ser Pro Val Val Ala Glu Ser Pro Lys
            180                 185                 190 aaa cct tcc atg gta aat aat tca ggg aaa gat ggg aat aca tct gca      624
Lys Pro Ser Met Val Asn Asn Ser Gly Lys Asp Gly Asn Thr Ser Ala
        195                 200                 205 aat tct gct gat gag tct gtt aaa ggg cct aat ctt aca gaa ata agt      672
Asn Ser Ala Asp Glu Ser Val Lys Gly Pro Asn Leu Thr Glu Ile Ser
210                 215                 220 aaa aaa att aca gaa tct aac gca gtt gtt ctc gcc gtg aaa gaa gtt      720
Lys Lys Ile Thr Glu Ser Asn Ala Val Val Leu Ala Val Lys Glu Val
225                 230                 235                 240 gaa act ttg ctt aca tct ata gat gag ctt gct aaa gct att ggt aaa      768
Glu Thr Leu Leu Thr Ser Ile Asp Glu Leu Ala Lys Ala Ile Gly Lys
                245                 250                 255 aaa ata aaa aac gat gtt agt tta gat aat gag gca gat cac aac gga      816
Lys Ile Lys Asn Asp Val Ser Leu Asp Asn Glu Ala Asp His Asn Gly
            260                 265                 270 tca tta ata tca gga gca tat tta att tca aac tta ata aca aaa aaa      864
Ser Leu Ile Ser Gly Ala Tyr Leu Ile Ser Asn Leu Ile Thr Lys Lys
        275                 280                 285 ata agt gca ata aaa gat tca gga gaa ttg aag gca gaa att gaa aag      912
Ile Ser Ala Ile Lys Asp Ser Gly Glu Leu Lys Ala Glu Ile Glu Lys
290                 295                 300 gct aag aaa tgt tct gaa gaa ttt act gct aaa tta aaa ggt gaa cac      960
Ala Lys Lys Cys Ser Glu Glu Phe Thr Ala Lys Leu Lys Gly Glu His
305                 310                 315                 320 aca gat ctt ggt aaa gaa ggc gtt act gat gat aat gca aaa aaa gcc     1008
Thr Asp Leu Gly Lys Glu Gly Val Thr Asp Asp Asn Ala Lys Lys Ala
                325                 330                 335
```

-continued

```
att tta aaa aca aat aat gat aaa act aag ggc gct gat gaa ctt gaa    1056
Ile Leu Lys Thr Asn Asn Asp Lys Thr Lys Gly Ala Asp Glu Leu Glu
            340                 345                 350 aag tta ttt gaa tca gta aaa aac ttg tca aaa gca gct aaa gag atg    1104
Lys Leu Phe Glu Ser Val Lys Asn Leu Ser Lys Ala Ala Lys Glu Met
        355                 360                 365 ctt act aat tca gtt aaa gag ctt aca agc taa                        1137
Leu Thr Asn Ser Val Lys Glu Leu Thr Ser *
        370                 375
```

<210> SEQ ID NO 28
<211> LENGTH: 378
<212> TYPE: PRT
<213> ORGANISM: Artificial Sequence
<220> FEATURE:
<223> OTHER INFORMATION: OspC Chimera

<400> SEQUENCE: 28

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
            180                 185                 190

Lys Pro Ser Met Val Asn Asn Ser Gly Lys Asp Gly Asn Thr Ser Ala
        195                 200                 205

Asn Ser Ala Asp Glu Ser Val Lys Gly Pro Asn Leu Thr Glu Ile Ser
    210                 215                 220

Lys Lys Ile Thr Glu Ser Asn Ala Val Val Leu Ala Val Lys Glu Val
225                 230                 235                 240

Glu Thr Leu Leu Thr Ser Ile Asp Glu Leu Ala Lys Ala Ile Gly Lys
                245                 250                 255

Lys Ile Lys Asn Asp Val Ser Leu Asp Asn Glu Ala Asp His Asn Gly
            260                 265                 270

Ser Leu Ile Ser Gly Ala Tyr Leu Ile Ser Asn Leu Ile Thr Lys Lys
        275                 280                 285

Ile Ser Ala Ile Lys Asp Ser Gly Glu Leu Lys Ala Glu Ile Glu Lys
    290                 295                 300
```

```
                    Ala Lys Lys Cys Ser Glu Glu Phe Thr Ala Lys Leu Lys Gly Glu His
                    305                 310                 315                 320

Thr Asp Leu Gly Lys Glu Gly Val Thr Asp Asp Asn Ala Lys Lys Ala
                                        325                 330                 335

Ile Leu Lys Thr Asn Asn Asp Lys Thr Lys Gly Ala Asp Glu Leu Glu
                                    340                 345                 350

Lys Leu Phe Glu Ser Val Lys Asn Leu Ser Lys Ala Ala Lys Glu Met
                                355                 360                 365

Leu Thr Asn Ser Val Lys Glu Leu Thr Ser
                    370                 375

<210> SEQ ID NO 29
<211> LENGTH: 1133
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1133)

<400> SEQUENCE: 29 atg gct tgt aat aat tca ggg aaa gat ggg aat aca tct gca aat tct        48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata aat aaa aaa        96
Ala Asp Glu Ser Val Lys Gly Pro Asn Leu Thr Glu Ile Asn Lys Lys
                20                  25                  30 att acg gat tct aat gcg gtt tta ctt gct gtg aaa gag gtt gaa gcg       144
Ile Thr Asp Ser Asn Ala Val Leu Leu Ala Val Lys Glu Val Glu Ala
            35                  40                  45 ttg ctg tca tct ata gat gaa att gct gct aaa gct att ggt aaa aaa       192
Leu Leu Ser Ser Ile Asp Glu Ile Ala Ala Lys Ala Ile Gly Lys Lys
        50                  55                  60 ata cac caa aat aat ggt ttg gat acc gaa aat aat cac aat gga tca       240
Ile His Gln Asn Asn Gly Leu Asp Thr Glu Asn Asn His Asn Gly Ser
 65                  70                  75                  80 ttg tta gcg gga gct tat gca ata tca acc cta ata aaa caa aaa tta       288
Leu Leu Ala Gly Ala Tyr Ala Ile Ser Thr Leu Ile Lys Gln Lys Leu
                85                  90                  95 gat gga ttg aaa aat gaa gga tta aag gaa aaa att gat gcg gct aag       336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat       384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta       432
Leu Gly Lys Glu Gly Val Thr Asp Ala Asp Ala Lys Glu Ala Ile Leu
    130                 135                 140 aaa gca aat ggt act aaa act aaa ggt gct gaa gaa ctt gga aaa tta       480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct       528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa       576
Asn Ser Val Lys Glu Leu Thr Ser Pro Val Val Ala Glu Ser Pro Lys
            180                 185                 190 aaa cct tcc atg gta aat aat tca gga aaa gat ggg aat aca tct gca       624
Lys Pro Ser Met Val Asn Asn Ser Gly Lys Asp Gly Asn Thr Ser Ala
        195                 200                 205
```

```
aat tct gct gat gag tct gtt aaa ggg cct aat ctt aca gaa ata agt      672
Asn Ser Ala Asp Glu Ser Val Lys Gly Pro Asn Leu Thr Glu Ile Ser
    210                 215                 220 aaa aaa att aca gaa tct aac gca gtt gtt ctg gct gtg aaa gaa att      720
Lys Lys Ile Thr Glu Ser Asn Ala Val Val Leu Ala Val Lys Glu Ile
225                 230                 235                 240 gaa act ttg ctt gca tct ata gat gaa ctt gct act aaa gct att ggt      768
Glu Thr Leu Leu Ala Ser Ile Asp Glu Leu Ala Thr Lys Ala Ile Gly
                245                 250                 255 aaa aaa ata caa caa aat ggt ggt tta gct gtc gaa gcg ggg cat aat      816
Lys Lys Ile Gln Gln Asn Gly Gly Leu Ala Val Glu Ala Gly His Asn
    260                 265                 270 gga aca ttg tta gca ggt gct tat aca ata tca aaa cta ata aca caa      864
Gly Thr Leu Leu Ala Gly Ala Tyr Thr Ile Ser Lys Leu Ile Thr Gln
275                 280                 285 aaa tta gat gga ttg aaa aat tca gaa aaa tta aag gaa aaa att gaa      912
Lys Leu Asp Gly Leu Lys Asn Ser Glu Lys Leu Lys Glu Lys Ile Glu
                290                 295                 300 aat gct aag aaa tgt tct gaa gat ttt act aaa aaa cta gaa gga gaa      960
Asn Ala Lys Lys Cys Ser Glu Asp Phe Thr Lys Lys Leu Glu Gly Glu
305                 310                 315                 320 cat gcg caa ctt gga att gaa aat gtt act gat gag aat gca aaa aaa     1008
His Ala Gln Leu Gly Ile Glu Asn Val Thr Asp Glu Asn Ala Lys Lys
                325                 330                 335 gct att tta ata aca gat gca gct aaa gat aag ggc gct gca gag ctt     1056
Ala Ile Leu Ile Thr Asp Ala Ala Lys Asp Lys Gly Ala Ala Glu Leu
                340                 345                 350 gaa aag cta ttt aaa gca gta gaa aac ttg gca aaa gca gct aaa gag     1104
Glu Lys Leu Phe Lys Ala Val Glu Asn Leu Ala Lys Ala Ala Lys Glu
            355                 360                 365 atg ctt gct aat tca gtt aaa gag ctt ac                              1133
Met Leu Ala Asn Ser Val Lys Glu Leu
    370                 375

<210> SEQ ID NO 30
<211> LENGTH: 377
<212> TYPE: PRT
<213> ORGANISM: Artificial Sequence
<220> FEATURE:
<223> OTHER INFORMATION: OspC Chimera

<400> SEQUENCE: 30

Met Ala Cys Asn Asn Ser Gly Lys Asp Gly Asn Thr Ser Ala Asn Ser
  1               5                  10                  15

Ala Asp Glu Ser Val Lys Gly Pro Asn Leu Thr Glu Ile Asn Lys Lys
                20                  25                  30

Ile Thr Asp Ser Asn Ala Val Leu Leu Ala Val Lys Glu Val Glu Ala
            35                  40                  45

Leu Leu Ser Ser Ile Asp Glu Ile Ala Ala Lys Ala Ile Gly Lys Lys
        50                  55                  60

Ile His Gln Asn Asn Gly Leu Asp Thr Glu Asn Asn His Asn Gly Ser
 65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125
```

```
Leu Gly Lys Glu Gly Val Thr Asp Ala Asp Ala Lys Glu Ala Ile Leu
            130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Lys
                180                 185                 190

Lys Pro Ser Met Val Asn Asn Ser Gly Lys Asp Gly Asn Thr Ser Ala
                195                 200                 205

Asn Ser Ala Asp Glu Ser Val Lys Gly Pro Asn Leu Thr Glu Ile Ser
            210                 215                 220

Lys Lys Ile Thr Glu Ser Asn Ala Val Val Leu Ala Val Lys Glu Ile
225                 230                 235                 240

Glu Thr Leu Leu Ala Ser Ile Asp Glu Leu Ala Thr Lys Ala Ile Gly
                245                 250                 255

Lys Lys Ile Gln Gln Asn Gly Gly Leu Ala Val Glu Ala Gly His Asn
                260                 265                 270

Gly Thr Leu Leu Ala Gly Ala Tyr Thr Ile Ser Lys Leu Ile Thr Gln
            275                 280                 285

Lys Leu Asp Gly Leu Lys Asn Ser Glu Lys Leu Lys Glu Lys Ile Glu
            290                 295                 300

Asn Ala Lys Lys Cys Ser Glu Asp Phe Thr Lys Lys Leu Glu Gly Glu
305                 310                 315                 320

His Ala Gln Leu Gly Ile Glu Asn Val Thr Asp Glu Asn Ala Lys Lys
                325                 330                 335

Ala Ile Leu Ile Thr Asp Ala Ala Lys Asp Lys Gly Ala Ala Glu Leu
                340                 345                 350

Glu Lys Leu Phe Lys Ala Val Glu Asn Leu Ala Lys Ala Ala Lys Glu
            355                 360                 365

Met Leu Ala Asn Ser Val Lys Glu Leu
            370                 375

<210> SEQ ID NO 31
<211> LENGTH: 1112
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1112)

<400> SEQUENCE: 31 atg gct tgt aat aat tca ggg aaa gat ggg aat aca tct gca aat tct    48
Met Ala Cys Asn Asn Ser Gly Lys Asp Gly Asn Thr Ser Ala Asn Ser
1               5                  10                  15 gct gat gag tct gtt aaa ggg cct aat ctt aca gaa ata agt aaa aaa    96
Ala Asp Glu Ser Val Lys Gly Pro Asn Leu Thr Glu Ile Ser Lys Lys
                20                  25                  30 att acg gat tct aat gcg gtt tta ctt gct gtg aaa gag gtt gaa gcg   144
Ile Thr Asp Ser Asn Ala Val Leu Leu Ala Val Lys Glu Val Glu Ala
            35                  40                  45 ttg ctg tca tct ata gat gag ctt gct aaa gct att ggt aaa aaa ata   192
Leu Leu Ser Ser Ile Asp Glu Leu Ala Lys Ala Ile Gly Lys Lys Ile
        50                  55                  60 aaa aac gat ggt agt tta gat aat gaa gca aat cgc aac gag tca ttg   240
Lys Asn Asp Gly Ser Leu Asp Asn Glu Ala Asn Arg Asn Glu Ser Leu
```

```
                65                  70                  75                  80
tta gca gga gct tat aca ata tca acc tta ata aca caa aaa tta agt         288
Leu Ala Gly Ala Tyr Thr Ile Ser Thr Leu Ile Thr Gln Lys Leu Ser
                         85                  90                  95 aaa tta aac gga tca gaa ggt tta aag gaa aag att gcc gca gct aag         336
Lys Leu Asn Gly Ser Glu Gly Leu Lys Glu Lys Ile Ala Ala Ala Lys
                100                 105                 110 aaa tgc tct gaa gag ttt agt act aaa cta aaa gat aat cat gca cag         384
Lys Cys Ser Glu Glu Phe Ser Thr Lys Leu Lys Asp Asn His Ala Gln
            115                 120                 125 ctt ggt ata cag ggc gtt act gat gaa aat gca aaa aaa gct att tta         432
Leu Gly Ile Gln Gly Val Thr Asp Glu Asn Ala Lys Lys Ala Ile Leu
        130                 135                 140 aaa gca aat gca gcg ggt aaa gat aag ggc gtt gaa gaa ctt gaa aag         480
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt         528
Leu Ser Gly Ser Leu Glu Ser Leu Ser Lys Ala Ala Lys Glu Met Leu
                    165                 170                 175 gct aat tca gtt aaa gag ctt aca agc cct gtt gtc cat ggt aat aat         576
Ala Asn Ser Val Lys Glu Leu Thr Ser Pro Val Val His Gly Asn Asn
                180                 185                 190 tca aga aaa gat ggg aat gca tct aca aat tct gcc gat gag tct gtt         624
Ser Arg Lys Asp Gly Asn Ala Ser Thr Asn Ser Ala Asp Glu Ser Val
            195                 200                 205 aaa ggg cct aat ctt aca gaa ata agt aaa aaa att aca gaa tct aac         672
Lys Gly Pro Asn Leu Thr Glu Ile Ser Lys Lys Ile Thr Glu Ser Asn
        210                 215                 220 gca gtt gtt ctg gcc gtg aaa gaa gtt gag acc tta ctt gca tct ata         720
Ala Val Val Leu Ala Val Lys Glu Val Glu Thr Leu Leu Ala Ser Ile
225                 230                 235                 240 gat gaa ctt gct acc aaa gct att ggt aag aaa ata ggc aat aat ggt         768
Asp Glu Leu Ala Thr Lys Ala Ile Gly Lys Lys Ile Gly Asn Asn Gly
                    245                 250                 255 tta gag gcc aat cag agt aaa aac aca tca ttg tta tca gga gct tat         816
Leu Glu Ala Asn Gln Ser Lys Asn Thr Ser Leu Leu Ser Gly Ala Tyr
                260                 265                 270 gca ata tct gac cta ata gca gaa aaa tta aat gta ttg aaa aat gaa         864
Ala Ile Ser Asp Leu Ile Ala Glu Lys Leu Asn Val Leu Lys Asn Glu
            275                 280                 285 gaa tta aag gaa aag att gat aca gct aag caa tgt tct aca gaa ttt         912
Glu Leu Lys Glu Lys Ile Asp Thr Ala Lys Gln Cys Ser Thr Glu Phe
        290                 295                 300 act aat aaa cta aaa agt gaa cat gca gtg ctt ggt ctg gac aat ctt         960
Thr Asn Lys Leu Lys Ser Glu His Ala Val Leu Gly Leu Asp Asn Leu
305                 310                 315                 320 act gat gat aat gca caa aga gct att tta aaa aaa cat gca aat aaa        1008
Thr Asp Asp Asn Ala Gln Arg Ala Ile Leu Lys Lys His Ala Asn Lys
                    325                 330                 335 gat aag ggt gct gca gaa ctt gaa aag tta ttt aaa gcg gta gaa aac        1056
Asp Lys Gly Ala Ala Glu Leu Glu Lys Leu Phe Lys Ala Val Glu Asn
                340                 345                 350 tta tca aaa gca gct caa gac aca tta aaa aat gct gtt aaa gag ctt        1104
Leu Ser Lys Ala Ala Gln Asp Thr Leu Lys Asn Ala Val Lys Glu Leu
            355                 360                 365 aca agt cc                                                             1112
Thr Ser
370
```

<210> SEQ ID NO 32
<211> LENGTH: 370
<212> TYPE: PRT
<213> ORGANISM: Artificial Sequence
<220> FEATURE:
<223> OTHER INFORMATION: OspC Chimera

<400> SEQUENCE: 32

```
Met Ala Cys Asn Asn Ser Gly Lys Asp Gly Asn Thr Ser Ala Asn Ser
 1               5                  10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Leu Ala Lys Ala Ile Gly Lys Lys Ile
    50                  55                  60

Lys Asn Asp Gly Ser Leu Asp Asn Glu Ala Asn Arg Asn Glu Ser Leu
65                  70                  75                  80

Leu Ala Gly Ala Tyr Thr Ile Ser Th

370

<210> SEQ ID NO 33
<211> LENGTH: 1113
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1113)

<400> SEQUENCE: 33

```
atg gct tgt aat aat tca ggg aaa gat ggg aat aca tct gca aat tct        48
Met Ala Cys Asn Asn Ser Gly Lys Asp Gly Asn Thr Ser Ala Asn -continued

```
tta gat aat gag gca gat cac aac gga tca tta ata tca gga gca tat    816
Leu Asp Asn Glu Ala Asp His Asn Gly Ser Leu Ile Ser Gly Ala Tyr
        260                 265                 270 tta att tca aac tta ata aca aaa aaa ata agt gca ata aaa gat tca    864
Leu Ile Ser Asn Leu Ile Thr Lys Lys Ile Ser Ala Ile Lys Asp Ser
275                 280                 285 gga gaa ttg aag gca gaa att gaa aag gct aag aaa tgt tct gaa gaa    912
Gly Glu Leu Lys Ala Glu Ile Glu Lys Ala Lys Lys Cys Ser Glu Glu
        290                 295                 300 ttt act gct aaa tta aaa ggt gaa cac aca gat ctt ggt aaa gaa ggc    960
Phe Thr Ala Lys Leu Lys Gly Glu His Thr Asp Leu Gly Lys Glu Gly
305                 310                 315                 320 gtt act gat gat aat gca aaa aaa gcc att tta aaa aca aat aat gat   1008
Val Thr Asp Asp Asn Ala Lys Lys Ala Ile Leu Lys Thr Asn Asn Asp
                325                 330                 335 aaa act aag ggc gct gat gaa ctt gaa aag tta ttt gaa tca gta aaa   1056
Lys Thr Lys Gly Ala Asp Glu Leu Glu Lys Leu Phe Glu Ser Val Lys
            340                 345                 350 aac ttg tca aaa gca gct aaa gag atg ctt act aat tca gtt aaa gag   1104
Asn Leu Ser Lys Ala Ala Lys Glu Met Leu Thr Asn Ser Val Lys Glu
        355                 360                 365 ctt aca agc                                                       1113
Leu Thr Ser
    370
```

<210> SEQ ID NO 34
<211> LENGTH: 371
<212> TYPE: PRT
<213> ORGANISM: Artificial Sequence
<220> FEATURE:
<223> OTHER INFORMATION: OspC Chimera

<400> SEQUENCE: 34

```
Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile

-continued

```
                    195                 200                 205
Lys Gly Pro Asn Leu Thr Glu Ile Ser Lys Lys Ile Thr Glu Ser Asn
    210                 215                 220

Ala Val Leu Ala Val Lys Glu Val Glu Thr Leu Leu Thr Ser Ile
225                 230                 235                 240

Asp Glu Leu Ala Lys Ala Ile Gly Lys Ile Lys Asn Asp Val Ser
                245                 250                 255

Leu Asp Asn Glu Ala Asp His Asn Gly Ser Leu Ile Ser Gly Ala Tyr
                260                 265                 270

Leu Ile Ser Asn Leu Ile Thr Lys Lys Ile Ser Ala Ile Lys Asp Ser
            275                 280                 285

Gly Glu Leu Lys Ala Glu Ile Glu Lys Ala Lys Lys Cys Ser Glu Glu
    290                 295                 300

Phe Thr Ala Lys Leu Lys Gly Glu His Thr Asp Leu Gly Lys Glu Gly
305                 310                 315                 320

Val Thr Asp Asp Asn Ala Lys Lys Ala Ile Leu Lys Thr Asn Asn Asp
                325                 330                 335

Lys Thr Lys Gly Ala Asp Glu Leu Glu Lys Leu Phe Glu Ser Val Lys
                340                 345                 350

Asn Leu Ser Lys Ala Ala Lys Glu Met Leu Thr Asn Ser Val Lys Glu
            355                 360                 365

Leu Thr Ser
    370
```

<210> SEQ ID NO 35
<211> LENGTH: 1112
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1112)

<400> SEQUENCE: 35

```
atg gct tgt aat aat tca ggg aaa gat ggg aat aca tct gca aat tct       48
Met Ala Cys Asn Asn Ser Gly Lys Asp Gly Asn Thr Ser Ala Asn Ser
1               5                   10                  15 gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45 ttg ctg tca tct ata gat gag ctt gct aaa gct att ggt aaa aaa ata      192
Leu Leu Ser Ser Ile Asp Glu Leu Ala Lys Ala Ile Gly Lys Lys Ile
    50                  55                  60 aaa aac gat ggt agt tta gat aat gaa gca aat cgc aac gag tca ttg      240
Lys Asn Asp Gly Ser Leu Asp Asn Glu Ala Asn Arg Asn Glu Ser Leu
65                  70                  75                  80 tta gca gga gct tat aca ata tca acc tta ata aca caa aaa tta agt      288
Leu Ala Gly Ala Tyr Thr Ile Ser Thr Leu Ile Thr Gln Lys Leu Ser
                85                  90                  95 aaa tta aac gga tca gaa ggt tta aag gaa aag att gcc gca gct aag      336
Lys Leu Asn Gly Ser Glu Gly Leu Lys Glu Lys Ile Ala Ala Ala Lys
            100                 105                 110 aaa tgc tct gaa gag ttt agt act aaa cta aaa gat aat cat gca cag      384
Lys Cys Ser Glu Glu Phe Ser Thr Lys Leu Lys Asp Asn His Ala Gln
        115                 120                 125
```

```
ctt ggt ata cag ggc gtt act gat gaa aat gca aaa aaa gct att tta      432
Leu Gly Ile Gln Gly Val Thr Asp Glu Asn Ala Lys Lys Ala Ile Leu
    130                 135                 140 aaa gca aat gca gcg ggt aaa gat aag ggc gtt gaa gaa ctt gaa aag      480
Lys Ala Asn Ala Ala Gly Lys Asp Lys Gly Val Glu Glu Leu Glu Lys
145                 150                 155                 160 ttg tcc gga tca tta gaa agc tta tca aaa gca gct aaa gag atg ctt      528
Leu Ser Gly Ser Leu Glu Ser Leu Ser Lys Ala Ala Lys Glu Met Leu
                165                 170                 175 gct aat tca gtt aaa gag ctt aca agc cct gtt gtc cat ggt aat aat      576
Ala Asn Ser Val Lys Glu Leu Thr Ser Pro Val Val His Gly Asn Asn
            180                 185                 190 tca gga aaa gat ggg aat aca tct gca aat tct gct gat gag tct gtt      624
Ser Gly Lys Asp Gly Asn Thr Ser Ala Asn Ser Ala Asp Glu Ser Val
        195                 200                 205 aaa ggg cct aat ctt aca gaa ata agt aaa aaa att aca gaa tct aac      672
Lys Gly Pro Asn Leu Thr Glu Ile Ser Lys Lys Ile Thr Glu Ser Asn
    210                 215                 220 gca gtt gtt ctg gct gtg aaa gaa att gaa act ttg ctt gca tct ata      720
Ala Val Val Leu Ala Val Lys Glu Ile Glu Thr Leu Leu Ala Ser Ile
225                 230                 235                 240 gat gaa ctt gct act aaa gct att ggt aaa aaa ata caa caa aat ggt      768
Asp Glu Leu Ala Thr Lys Ala Ile Gly Lys Lys Ile Gln Gln Asn Gly
                245                 250                 255 ggt tta gct gtc gaa gcg ggg cat aat gga aca ttg tta gca ggt gct      816
Gly Leu Ala Val Glu Ala Gly His Asn Gly Thr Leu Leu Ala Gly Ala
            260                 265                 270 tat aca ata tca aaa cta ata aca caa aaa tta gat gga ttg aaa aat      864
Tyr Thr Ile Ser Lys Leu Ile Thr Gln Lys Leu Asp Gly Leu Lys Asn
        275                 280                 285 tca gaa aaa tta aag gaa aaa att gaa aat gct aag aaa tgt tct gaa      912
Ser Glu Lys Leu Lys Glu Lys Ile Glu Asn Ala Lys Lys Cys Ser Glu
    290                 295                 300 gat ttt act aaa aaa cta gaa gga gaa cat gcg caa ctt gga att gaa      960
Asp Phe Thr Lys Lys Leu Glu Gly Glu His Ala Gln Leu Gly Ile Glu
305                 310                 315                 320 aat gtt act gat gag aat gca aaa aaa gct att tta ata aca gat gca     1008
Asn Val Thr Asp Glu Asn Ala Lys Lys Ala Ile Leu Ile Thr Asp Ala
                325                 330                 335 gct aaa gat aag ggc gct gca gag ctt gaa aag cta ttt aaa gca gta     1056
Ala Lys Asp Lys Gly Ala Ala Glu Leu Glu Lys Leu Phe Lys Ala Val
            340                 345                 350 gaa aac ttg gca aaa gca gct aaa gag atg ctt gct aat tca gtt aaa     1104
Glu Asn Leu Ala Lys Ala Ala Lys Glu Met Leu Ala Asn Ser Val Lys
        355                 360                 365 gag ctt ac                                                          1112
Glu Leu
    370

<210> SEQ ID NO 36
<211> LENGTH: 370
<212> TYPE: PRT
<213> ORGANISM: Artificial Sequence
<220> FEATURE:
<223> OTHER INFORMATION: OspC Chimera

<400> SEQUENCE: 36

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
```

```
                20                  25                  30
Ile Thr Asp Ser Asn Ala Val Leu Leu Ala Val Lys Glu Val Glu Ala
         35                  40                  45

Leu Leu Ser Ser Ile Asp Glu Leu Ala Lys Ala Ile Gly Lys Lys Ile
 50                  55                  60

Lys Asn Asp Gly Ser Leu Asp Asn Glu Ala Asn Arg Asn Glu Ser Leu
 65                  70                  75                  80

Leu Ala Gly Ala Tyr Thr Ile Ser Thr Leu Ile Thr Gln Lys Leu Ser
                 85                  90                  95

Lys Leu Asn Gly Ser Glu Gly Leu Lys Glu Lys Ile Ala Ala Ala Lys
                100                 105                 110

Lys Cys Ser Glu Glu Phe Ser Thr Lys Leu Lys Asp Asn His Ala Gln
                115                 120                 125

Leu Gly Ile Gln Gly Val Thr Asp Glu Asn Ala Lys Lys Ala Ile Leu
            130                 135                 140

Lys Ala Asn Ala Ala Gly Lys Asp Lys Gly Val Glu Glu Leu Glu Lys
145                 150                 155                 160

Leu Ser Gly Ser Leu Glu Ser Leu Ser Lys Ala Ala Lys Glu Met Leu
                165                 170                 175

Ala Asn Ser Val Lys Glu Leu Thr Ser Pro Val Val His Gly Asn Asn
                180                 185                 190

Ser Gly Lys Asp Gly Asn Thr Ser Ala Asn Ser Ala Asp Glu Ser Val
                195                 200                 205

Lys Gly Pro Asn Leu Thr Glu Ile Ser Lys Lys Ile Thr Glu Ser Asn
            210                 215                 220

Ala Val Val Leu Ala Val Lys Glu Ile Glu Thr Leu Leu Ala Ser Ile
225                 230                 235                 240

Asp Glu Leu Ala Thr Lys Ala Ile Gly Lys Lys Ile Gln Gln Asn Gly
                245                 250                 255

Gly Leu Ala Val Glu Ala Gly His Asn Gly Thr Leu Leu Ala Gly Ala
                260                 265                 270

Tyr Thr Ile Ser Lys Leu Ile Thr Gln Lys Leu Asp Gly Leu Lys Asn
            275                 280                 285

Ser Glu Lys Leu Lys Glu Lys Ile Glu Asn Ala Lys Lys Cys Ser Glu
        290                 295                 300

Asp Phe Thr Lys Lys Leu Glu Gly Glu His Ala Gln Leu Gly Ile Glu
305                 310                 315                 320

Asn Val Thr Asp Glu Asn Ala Lys Lys Ala Ile Leu Ile Thr Asp Ala
                325                 330                 335

Ala Lys Asp Lys Gly Ala Ala Glu Leu Glu Lys Leu Phe Lys Ala Val
            340                 345                 350

Glu Asn Leu Ala Lys Ala Ala Lys Glu Met Leu Ala Asn Ser Val Lys
        355                 360                 365

Glu Leu
    370

<210> SEQ ID NO 37
<211> LENGTH: 1106
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1106)
```

-continued

```
<400> SEQUENCE: 37 atg gct tgt aat aat tca gga aaa gat ggg aat gca tct gca aat tct      48
Met Ala Cys Asn Asn Ser Gly Lys Asp Gly Asn Ala Ser Ala Asn Ser
 1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
             20                  25                  30 att aca gaa tct aac gca gtt gtt ctg gcc gtg aaa gaa gtt gag acc     144
Ile Thr Glu Ser Asn Ala Val Val Leu Ala Val Lys Glu Val Glu Thr
         35                  40                  45 tta ctt gca tct ata gat gaa ctt gct acc aaa gct att ggt aaa aaa     192
Leu Leu Ala Ser Ile Asp Glu Leu Ala Thr Lys Ala Ile Gly Lys Lys
     50                  55                  60 ata ggc aat aat ggt tta gag gcc aat cag agt aaa aac aca tca ttg     240
Ile Gly Asn Asn Gly Leu Glu Ala Asn Gln Ser Lys Asn Thr Ser Leu
 65                  70                  75                  80 tta tca gga gct tat gca ata tct gac cta ata gca gaa aaa tta aat     288
Leu Ser Gly Ala Tyr Ala Ile Ser Asp Leu Ile Ala Glu Lys Leu Asn
                 85                  90                  95 gta ttg aaa aat gaa gaa tta aag gaa aag att gat aca gct aag caa     336
Val Leu Lys Asn Glu Glu Leu Lys Glu Lys Ile Asp Thr Ala Lys Gln
            100                 105                 110 tgt tct aca gaa ttt act aat aaa cta aaa agt gaa cat gca gtg ctt     384
Cys Ser Thr Glu Phe Thr Asn Lys Leu Lys Ser Glu His Ala Val Leu
        115                 120                 125 ggt ctg gac aat ctt act gat gat aat gca caa aga gct att tta aaa     432
Gly Leu Asp Asn Leu Thr Asp Asp Asn Ala Gln Arg Ala Ile Leu Lys
    130                 135                 140 aaa cat gca aat aaa gat aag ggt gct gca gaa ctt gaa aag tta ttt     480
Lys His Ala Asn Lys Asp Lys Gly Ala Ala Glu Leu Glu Lys Leu Phe
145                 150                 155                 160 aaa gcg gta gaa aac tta tca aaa gca gct caa gac aca tta aaa aat     528
Lys Ala Val Glu Asn Leu Ser Lys Ala Ala Gln Asp Thr Leu Lys Asn
                165                 170                 175 gct gtt aaa gag ctt aca agt cct att gtc cat ggt aat aat tca aga     576
Ala Val Lys Glu Leu Thr Ser Pro Ile Val His Gly Asn Asn Ser Arg
            180                 185                 190 aaa gat ggg aat gca tct aca aat tct gcc gat gag tct gtt aaa ggg     624
Lys Asp Gly Asn Ala Ser Thr Asn Ser Ala Asp Glu Ser Val Lys Gly
        195                 200                 205 cct aat ctt aca gaa ata agt aaa aaa att aca gaa tct aac gca gtt     672
Pro Asn Leu Thr Glu Ile Ser Lys Lys Ile Thr Glu Ser Asn Ala Val
    210                 215                 220 gtt ctg gcc gtg aaa gaa gtt gag acc tta ctt gca tct ata gat gaa     720
Val Leu Ala Val Lys Glu Val Glu Thr Leu Leu Ala Ser Ile Asp Glu
225                 230                 235                 240 ctt gct acc aaa gct att ggt aag aaa ata ggc aat aat ggt tta gag     768
Leu Ala Thr Lys Ala Ile Gly Lys Lys Ile Gly Asn Asn Gly Leu Glu
                245                 250                 255 gcc aat cag agt aaa aac aca tca ttg tta tca gga gct tat gca ata     816
Ala Asn Gln Ser Lys Asn Thr Ser Leu Leu Ser Gly Ala Tyr Ala Ile
            260                 265                 270 tct gac cta ata gca gaa aaa tta aat gta ttg aaa aat gaa gaa tta     864
Ser Asp Leu Ile Ala Glu Lys Leu Asn Val Leu Lys Asn Glu Glu Leu
        275                 280                 285 aag gaa aag att gat aca gct aag caa tgt tct aca gaa ttt act aat     912
Lys Glu Lys Ile Asp Thr Ala Lys Gln Cys Ser Thr Glu Phe Thr Asn
    290                 295                 300 aaa cta aaa agt gaa cat gca gtg ctt ggt ctg gac aat ctt act gat     960
```

```
Lys Leu Lys Ser Glu His Ala Val Leu Gly Leu Asp Asn Leu Thr Asp
305                 310                 315                 320 gat aat gca caa aga gct att tta aaa aaa cat gca aat aaa gat aag    1008
Asp Asn Ala Gln Arg Ala Ile Leu Lys Lys His Ala Asn Lys Asp Lys
                325                 330                 335 ggt gct gca gaa ctt gaa aag tta ttt aaa gcg gta gaa aac tta tca    1056
Gly Ala Ala Glu Leu Glu Lys Leu Phe Lys Ala Val Glu Asn Leu Ser
            340                 345                 350 aaa gca gct caa gac aca tta aaa aat gct gtt aaa gag ctt aca agt    1104
Lys Ala Ala Gln Asp Thr Leu Lys Asn Ala Val Lys Glu Leu Thr Ser
        355                 360                 365 cc                                                                 1106

<210> SEQ ID NO 38
<211> LENGTH: 368
<212> TYPE: PRT
<213> ORGANISM: Artificial Sequence
<220> FEATURE:
<223> OTHER INFORMATION: OspC Chimera

<400> SEQUENCE: 38

Met Ala Cys Asn Asn Ser Gly Lys Asp Gly Asn Ala Ser Ala Asn Ser
1               5                   10                  15

Ala Asp Glu Ser Val Lys Gly Pro Asn Leu Thr Glu Ile Ser Lys Lys
            20                  25                  30

Ile Thr Glu Ser Asn Ala Val Val Leu Ala Val Lys Glu Val Glu Thr
        35                  40                  45

Leu Leu Ala Ser Ile Asp Glu Leu Ala Thr Lys Ala Ile Gly Lys Lys
    50                  55                  60

Ile Gly Asn Asn Gly Leu Glu Ala Asn Gln Ser Lys Asn Thr Ser Leu
65                  70                  75                  80

Leu Ser Gly Ala Tyr Ala Ile Ser Asp Leu Ile Ala Glu Lys Leu Asn
                85                  90                  95

Val Leu Lys Asn Glu Glu Leu Lys Glu Lys Ile Asp Thr Ala Lys Gln
            100                 105                 110

Cys Ser Thr Glu Phe Thr Asn Lys Leu Lys Ser Glu His Ala Val Leu
        115                 120                 125

Gly Leu Asp Asn Leu Thr Asp Asp Asn Ala Gln Arg Ala Ile Leu Lys
    130                 135                 140

Lys His Ala Asn Lys Asp Lys Gly Ala Ala Glu Leu Glu Lys Leu Phe
145                 150                 155                 160

Lys Ala Val Glu Asn Leu Ser Lys Ala Ala Gln Asp Thr Leu Lys Asn
                165                 170                 175

Ala Val Lys Glu Leu Thr Ser Pro Ile Val His Gly Asn Asn Ser Arg
            180                 185                 190

Lys Asp Gly Asn Ala Ser Thr Asn Ser Ala Asp Glu Ser Val Lys Gly
        195                 200                 205

Pro Asn Leu Thr Glu Ile Ser Lys Lys Ile Thr Glu Ser Asn Ala Val
    210                 215                 220

Val Leu Ala Val Lys Glu Val Glu Thr Leu Leu Ala Ser Ile Asp Glu
225                 230                 235                 240

Leu Ala Thr Lys Ala Ile Gly Lys Lys Ile Gly Asn Asn Gly Leu Glu
                245                 250                 255

Ala Asn Gln Ser Lys Asn Thr Ser Leu Leu Ser Gly Ala Tyr Ala Ile
            260                 265                 270

Ser Asp Leu Ile Ala Glu Lys Leu Asn Val Leu Lys Asn Glu Glu Leu
```

```
                        275                 280                 285
Lys Glu Lys Ile Asp Thr Ala Lys Gln Cys Ser Thr Glu Phe Thr Asn
    290                 295                 300

Lys Leu Lys Ser Glu His Ala Val Leu Gly Leu Asp Asn Leu Thr Asp
305                 310                 315                 320

Asp Asn Ala Gln Arg Ala Ile Leu Lys Lys His Ala Asn Lys Asp Lys
                325                 330                 335

Gly Ala Ala Glu Leu Glu Lys Leu Phe Lys Ala Val Glu Asn Leu Ser
                340                 345                 350

Lys Ala Ala Gln Asp Thr Leu Lys Asn Ala Val Lys Glu Leu Thr Ser
                355                 360                 365

<210> SEQ ID NO 39
<211> LENGTH: 1107
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1107)

<400> SEQUENCE: 39 atg gct tgt aat aat tca gga aaa gat ggg aat gca tct gca aat tct      48
Met Ala Cys Asn Asn Ser Gly Lys Asp Gly Asn Ala Ser Ala Asn Ser
  1               5                  10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
                 20                  25                  30 att aca gaa tct aac gca gtt gtt ctg gcc gtg aaa gaa gtt gag acc     144
Ile Thr Glu Ser Asn Ala Val Val Leu Ala Val Lys Glu Val Glu Thr
             35                  40                  45 tta ctt gca tct ata gat gaa ctt gct acc aaa gct att ggt aaa aaa     192
Leu Leu Ala Ser Ile Asp Glu Leu Ala Thr Lys Ala Ile Gly Lys Lys
         50                  55                  60 ata ggc aat aat ggt tta gag gcc aat cag agt aaa aac aca tca ttg     240
Ile Gly Asn Asn Gly Leu Glu Ala Asn Gln Ser Lys Asn Thr Ser Leu
 65                  70                  75                  80 tta tca gga gct tat gca ata tct gac cta ata gca gaa aaa tta aat     288
Leu Ser Gly Ala Tyr Ala Ile Ser Asp Leu Ile Ala Glu Lys Leu Asn
                 85                  90                  95 gta ttg aaa aat gaa gaa tta aag gaa aag att gat aca gct aag caa     336
Val Leu Lys Asn Glu Glu Leu Lys Glu Lys Ile Asp Thr Ala Lys Gln
                100                 105                 110 tgt tct aca gaa ttt act aat aaa cta aaa agt gaa cat gca gtg ctt     384
Cys Ser Thr Glu Phe Thr Asn Lys Leu Lys Ser Glu His Ala Val Leu
            115                 120                 125 ggt ctg gac aat ctt act gat gat aat gca caa aga gct att tta aaa     432
Gly Leu Asp Asn Leu Thr Asp Asp Asn Ala Gln Arg Ala Ile Leu Lys
        130                 135                 140 aaa cat gca aat aaa gat aag ggt gct gca gaa ctt gaa aag tta ttt     480
Lys His Ala Asn Lys Asp Lys Gly Ala Ala Glu Leu Glu Lys Leu Phe
145                 150                 155                 160 aaa gcg gta gaa aac tta tca aaa gca gct caa gac aca tta aaa aat     528
Lys Ala Val Glu Asn Leu Ser Lys Ala Ala Gln Asp Thr Leu Lys Asn
                165                 170                 175 gct gtt aaa gag ctt aca agt cct att gtc cat ggt aat aat tca ggg     576
Ala Val Lys Glu Leu Thr Ser Pro Ile Val His Gly Asn Asn Ser Gly
            180                 185                 190 aaa gat ggg aat aca tct gca aat tct gct gat gag tct gtt aaa ggg     624
```

```
cct aat ctt aca gaa ata agt aaa aaa att aca gaa tct aac gca gtt         672
Pro Asn Leu Thr Glu Ile Ser Lys Lys Ile Thr Glu Ser Asn Ala Val
        210                 215                 220 gtt ctc gcc gtg aaa gaa gtt gaa act ttg ctt aca tct ata gat gag         720
Val Leu Ala Val Lys Glu Val Glu Thr Leu Leu Thr Ser Ile Asp Glu
225                 230                 235                 240 ctt gct aaa gct att ggt aaa aaa ata aaa aac gat gtt agt tta gat         768
Leu Ala Lys Ala Ile Gly Lys Lys Ile Lys Asn Asp Val Ser Leu Asp
                245                 250                 255 aat gag gca gat cac aac gga tca tta ata tca gga gca tat tta att         816
Asn Glu Ala Asp His Asn Gly Ser Leu Ile Ser Gly Ala Tyr Leu Ile
            260                 265                 270 tca aac tta ata aca aaa aaa ata agt gca ata aaa gat tca gga gaa         864
Ser Asn Leu Ile Thr Lys Lys Ile Ser Ala Ile Lys Asp Ser Gly Glu
        275                 280                 285 ttg aag gca gaa att gaa aag gct aag aaa tgt tct gaa gaa ttt act         912
Leu Lys Ala Glu Ile Glu Lys Ala Lys Lys Cys Ser Glu Glu Phe Thr
    290                 295                 300 gct aaa tta aaa ggt gaa cac aca gat ctt ggt aaa gaa ggc gtt act         960
Ala Lys Leu Lys Gly Glu His Thr Asp Leu Gly Lys Glu Gly Val Thr
305                 310                 315                 320 gat gat aat gca aaa aaa gcc att tta aaa aca aat aat gat aaa act        1008
Asp Asp Asn Ala Lys Lys Ala Ile Leu Lys Thr Asn Asn Asp Lys Thr
                325                 330                 335 aag ggc gct gat gaa ctt gaa aag tta ttt gaa tca gta aaa aac ttg        1056
Lys Gly Ala Asp Glu Leu Glu Lys Leu Phe Glu Ser Val Lys Asn Leu
            340                 345                 350 tca aaa gca gct aaa gag atg ctt act aat tca gtt aaa gag ctt aca        1104
Ser Lys Ala Ala Lys Glu Met Leu Thr Asn Ser Val Lys Glu Leu Thr
        355                 360                 365 agc                                                                    1107
Ser
```

<210> SEQ ID NO 40
<211> LENGTH: 369
<212> TYPE: PRT
<213> ORGANISM: Artificial Sequence
<220> FEATURE:
<223> OTHER INFORMATION: OspC Chimera

<400> SEQUENCE: 40

```
Met Ala Cys Asn Asn Ser Gly Lys Asp Gly Asn Ala Ser Ala As

```
Gly Leu Asp Asn Leu Thr Asp Asp Asn Ala Gln Arg Ala Ile Leu Lys
    130                 135                 140
Lys His Ala Asn Lys Asp Lys Gly Ala Ala Glu Leu Glu Lys Leu Phe
145                 150                 155                 160
Lys Ala Val Glu Asn Leu Ser Lys Ala Ala Gln Asp Thr Leu Lys Asn
                165                 170                 175
Ala Val Lys Glu Leu Thr Ser Pro Ile Val His Gly Asn Asn Ser Gly
            180                 185                 190
Lys Asp Gly Asn Thr Ser Ala Asn Ser Ala Asp Glu Ser Val Lys Gly
        195                 200                 205
Pro Asn Leu Thr Glu Ile Ser Lys Lys Ile Thr Glu Ser Asn Ala Val
    210                 215                 220
Val Leu Ala Val Lys Glu Val Glu Thr Leu Leu Thr Ser Ile Asp Glu
225                 230                 235                 240
Leu Ala Lys Ala Ile Gly Lys Lys Ile Lys Asn Asp Val Ser Leu Asp
                245                 250                 255
Asn Glu Ala Asp His Asn Gly Ser Leu Ile Ser Gly Ala Tyr Leu Ile
            260                 265                 270
Ser Asn Leu Ile Thr Lys Lys Ile Ser Ala Ile Lys Asp Ser Gly Glu
        275                 280                 285
Leu Lys Ala Glu Ile Glu Lys Ala Lys Lys Cys Ser Glu Glu Phe Thr
    290                 295                 300
Ala Lys Leu Lys Gly Glu His Thr Asp Leu Gly Lys Glu Gly Val Thr
305                 310                 315                 320
Asp Asp Asn Ala Lys Lys Ala Ile Leu Lys Thr Asn Asn Asp Lys Thr
                325                 330                 335
Lys Gly Ala Asp Glu Leu Glu Lys Leu Phe Glu Ser Val Lys Asn Leu
            340                 345                 350
Ser Lys Ala Ala Lys Glu Met Leu Thr Asn Ser Val Lys Glu Leu Thr
        355                 360                 365
Ser

<210> SEQ ID NO 41
<211> LENGTH: 1106
<212> TYPE: DNA
<213> ORGANISM: Artificial Sequence
<220> FEATURE:
<223> OTHER INFORMATION: OspC Chimera
<220> FEATURE:
<221> NAME/KEY: CDS
<222> LOCATION: (1)...(1106)

<400> SEQUENCE: 41 atg gct tgt aat aat tca gga aaa gat ggg aat gca tct gca aat tct      48
Met Ala Cys Asn Asn Ser Gly Lys Asp Gly Asn Ala Ser Ala Asn Ser
1               5                   10                  15 gct gat gag tct gtt aaa ggg cct aat ctt aca gaa ata agt aaa aaa      96
Ala Asp Glu Ser Val Lys Gly Pro Asn Leu Thr Glu Ile Ser Lys Lys
                20                  25                  30 att aca gaa tct aac gca gtt gtt ctg gcc gtg aaa gaa gtt gag acc    144
Ile Thr Glu Ser Asn Ala Val Val Leu Ala Val Lys Glu Val Glu Thr
            35                  40                  45 tta ctt gca tct ata gat gaa ctt gct acc aaa gct att ggt aaa aaa    192
Leu Leu Ala Ser Ile Asp Glu Leu Ala Thr Lys Ala Ile Gly Lys Lys
        50                  55                  60 ata ggc aat aat ggt tta gag gcc aat cag agt aaa aac aca tca ttg    240
Ile Gly Asn Asn Gly Leu Glu Ala Asn Gln Ser Lys Asn Thr Ser Leu
```

```
                65                  70                  75                  80
tta tca gga gct tat gca ata tct gac cta ata gca gaa aaa tta aat        288
Leu Ser Gly Ala Tyr Ala Ile Ser Asp Leu Ile Ala Glu Lys Leu Asn
                    85                  90                  95 gta ttg aaa aat gaa gaa tta aag gaa aag att gat aca gct aag caa        336
Val Leu Lys Asn Glu Glu Leu Lys Glu Lys Ile Asp Thr Ala Lys Gln
            100                 105                 110 tgt tct aca gaa ttt act aat aaa cta aaa agt gaa cat gca gtg ctt        384
Cys Ser Thr Glu Phe Thr Asn Lys Leu Lys Ser Glu His Ala Val Leu
        115                 120                 125 ggt ctg gac aat ctt act gat gat aat gca caa aga gct att tta aaa        432
Gly Leu Asp Asn Leu Thr Asp Asp Asn Ala Gln Arg Ala Ile Leu Lys
    130                 135                 140 aaa cat gca aat aaa gat aag ggt gct gca gaa ctt gaa aag tta ttt        480
Lys His Ala Asn Lys Asp Lys Gly Ala Ala Glu Leu Glu Lys Leu Phe
145                 150                 155                 160 aaa gcg gta gaa aac tta tca aaa gca gct caa gac aca tta aaa aat        528
Lys Ala Val Glu Asn Leu Ser Lys Ala Ala Gln Asp Thr Leu Lys Asn
                165                 170                 175 gct gtt aaa gag ctt aca agt cct att gtc cat ggt aat aat tca gga        576
Ala Val Lys Glu Leu Thr Ser Pro Ile Val His Gly Asn Asn Ser Gly
            180                 185                 190 aaa gat ggg aat aca tct gca aat tct gct gat gag tct gtt aaa ggg        624
Lys Asp Gly Asn Thr Ser Ala Asn Ser Ala Asp Glu Ser Val Lys Gly
        195                 200                 205 cct aat ctt aca gaa ata agt aaa aaa att aca gaa tct aac gca gtt        672
Pro Asn Leu Thr Glu Ile Ser Lys Lys Ile Thr Glu Ser Asn Ala Val
    210                 215                 220 gtt ctg gct gtg aaa gaa att gaa act ttg ctt gca tct ata gat gaa        720
Val Leu Ala Val Lys Glu Ile Glu Thr Leu Leu Ala Ser Ile Asp Glu
225                 230                 235                 240 ctt gct act aaa gct att ggt aaa aaa ata caa caa aat ggt ggt tta        768
Leu Ala Thr Lys Ala Ile Gly Lys Lys Ile Gln Gln Asn Gly Gly Leu
                245                 250                 255 gct gtc gaa gcg ggg cat aat gga aca ttg tta gca ggt gct tat aca        816
Ala Val Glu Ala Gly His Asn Gly Thr Leu Leu Ala Gly Ala Tyr Thr
            260                 265                 270 ata tca aaa cta ata aca caa aaa tta gat gga ttg aaa aat tca gaa        864
Ile Ser Lys Leu Ile Thr Gln Lys Leu Asp Gly Leu Lys Asn Ser Glu
        275                 280                 285 aaa tta aag gaa aaa att gaa aat gct aag aaa tgt tct gaa gat ttt        912
Lys Leu Lys Glu Lys Ile Glu Asn Ala Lys Lys Cys Ser Glu Asp Phe
    290                 295                 300 act aaa aaa cta gaa gga gaa cat gcg caa ctt gga att gaa aat gtt        960
Thr Lys Lys Leu Glu Gly Glu His Ala Gln Leu Gly Ile Glu Asn Val
305                 310                 315                 320 act gat gag aat gca aaa aaa gct att tta ata aca gat gca gct aaa       1008
Thr Asp Glu Asn Ala Lys Lys Ala Ile Leu Ile Thr Asp Ala Ala Lys
                325                 330                 335 gat aag ggc gct gca gag ctt gaa aag cta ttt aaa gca gta gaa aac       1056
Asp Lys Gly Ala Ala Glu Leu Glu Lys Leu Phe Lys Ala Val Glu Asn
            340                 345                 350 ttg gca aaa gca gct aaa gag atg ctt gct aat tca gtt aaa gag ctt       1104
Leu Ala Lys Ala Ala Lys Glu Met Leu Ala Asn Ser Val Lys Glu Leu
        355                 360                 365 ac                                                                    1106

<210> SEQ ID NO 42
<211> LENGTH: 368
```

<212> TYPE: PRT
<213> ORGANISM: Artificial Sequence
<220> FEATURE:
<223> OTHER INFORMATION: OspC Chimera

<400> SEQUENCE:

<212> TYPE: DNA
<213> ORGANISM: Borrelia burgdorferi
<220> FEATURE:
<221> NAME/KEY: CDS
<222> LOCATION: (1)...(633)

<400> SEQUENCE: 43

| | | | | | | | | | | | | | | | | |
|---|---|---|---|---|---|---|---|---|---|---|---|---|---|---|---|---|
| atg | aaa | aag | aat | aca | tta | agt | gcg | ata | tta | atg | act | tta | ttt | tta | ttt | 48 |
| Met | Lys | Lys | Asn | Thr | Leu | Ser | Ala | Ile | Leu | Met | Thr | Leu | Phe | Leu | Phe | |
| 1 | | | | 5 | | | | | 10 | | | | | 15 | | |
| ata | tct | tgt | aat | aat | tca | ggg | aaa | gat | ggg | aat | aca | tct | gca | aat | tct | 96 |
| Ile | Ser | Cys | Asn | Asn | Ser | Gly | Lys | Asp | Gly | Asn | Thr | Ser | Ala | Asn | Ser | |
| | | | | 20 | | | | | 25 | | | | | 30 | | |
| gct | gat | gag | tct | gtt | aaa | ggg | cct | aat | ctt | aca | gaa | ata | aat | aaa | aaa | 144 |
| Ala | Asp | Glu | Ser | Val | Lys | Gly | Pro | Asn | Leu | Thr | Glu | Ile | Asn | Lys | Lys | |
| | | | 35 | | | | | 40 | | | | | 45 | | | |
| att | acg | gat | tct | aat | gcg | gtt | tta | ctt | gct | gtg | aaa | gag | gtt | gaa | gcg | 192 |
| Ile | Thr | Asp | Ser | Asn | Ala | Val | Leu | Leu | Ala | Val | Lys | Glu | Val | Glu | Ala | |
| | 50 | | | | | 55 | | | | | 60 | | | | | |
| ttg | ctg | tca | tct | ata | gat | gaa | att | gct | gct | aaa | gct | att | ggt | aaa | aaa | 240 |
| Leu | Leu | Ser | Ser | Ile | Asp | Glu | Ile | Ala | Ala | Lys | Ala | Ile | Gly | Lys | Lys | |
| 65 | | | | | 70 | | | | | 75 | | | | | 80 | |
| ata | cac | caa | aat | aat | ggt | ttg | gat | acc | gaa | aat | aat | cac | aat | gga | tca | 288 |
| Ile | His | Gln | Asn | Asn | Gly | Leu | Asp | Thr | Glu | Asn | Asn | His | Asn | Gly | Ser | |
| | | | | 85 | | | | | 90 | | | | | 95 | | |
| ttg | tta | gcg | gga | gct | tat | gca | ata | tca | acc | cta | ata | aaa | caa | aaa | tta | 336 |
| Leu | Leu | Ala | Gly | Ala | Tyr | Ala | Ile | Ser | Thr | Leu | Ile | Lys | Gln | Lys | Leu | |
| | | | 100 | | | | | 105 | | | | | 110 | | | |
| gat | gga | ttg | aaa | aat | gaa | gga | tta | aag | gaa | aaa | att | gat | gcg | gct | aag | 384 |
| Asp | Gly | Leu | Lys | Asn | Glu | Gly | Leu | Lys | Glu | Lys | Ile | Asp | Ala | Ala | Lys | |
| | | 115 | | | | | 120 | | | | | 125 | | | | |
| aaa | tgt | tct | gaa | aca | ttt | act | aat | aaa | tta | aaa | gaa | aaa | cac | aca | gat | 432 |
| Lys | Cys | Ser | Glu | Thr | Phe | Thr | Asn | Lys | Leu | Lys | Glu | Lys | His | Thr | Asp | |
| | 130 | | | | | 135 | | | | | 140 | | | | | |
| ctt | ggt | aaa | gaa | ggt | gtt | act | gat | gct | gat | gca | aaa | gaa | gcc | att | tta | 480 |
| Leu | Gly | Lys | Glu | Gly | Val | Thr | Asp | Ala | Asp | Ala | Lys | Glu | Ala | Ile | Leu | |
| 145 | | | | | 150 | | | | | 155 | | | | | 160 | |
| aaa | gca | aat | ggt | act | aaa | act | aaa | ggt | gct | gaa | gaa | ctt | gga | aaa | tta | 528 |
| Lys | Ala | Asn | Gly | Thr | Lys | Thr | Lys | Gly | Ala | Glu | Glu | Leu | Gly | Lys | Leu | |
| | | | | 165 | | | | | 170 | | | | | 175 | | |
| ttt | gaa | tca | gta | gag | gtc | ttg | tca | aaa | gca | gct | aaa | gag | atg | ctt | gct | 576 |
| Phe | Glu | Ser | Val | Glu | Val | Leu | Ser | Lys | Ala | Ala | Lys | Glu | Met | Leu | Ala | |
| | | | 180 | | | | | 185 | | | | | 190 | | | |
| aat | tca | gtt | aaa | gag | ctt | aca | agc | cct | gtt | gtg | gca | gaa | agt | cca | aaa | 624 |
| Asn | Ser | Val | Lys | Glu | Leu | Thr | Ser | Pro | Val | Val | Ala | Glu | Ser | Pro | Lys | |
| | | 195 | | | | | 200 | | | | | 205 | | | | |
| aaa | cct | taa | | | | | | | | | | | | | | 633 |
| Lys | Pro | * | | | | | | | | | | | | | | |
| 210 | | | | | | | | | | | | | | | | |

<210> SEQ ID NO 44
<211> LENGTH: 210
<212> TYPE: PRT
<213> ORGANISM: Borrelia burgdorferi

<400> SEQUENCE: 44

| | | | | | | | | | | | | | | |
|---|---|---|---|---|---|---|---|---|---|---|---|---|---|---|
| Met | Lys | Lys | Asn | Thr | Leu | Ser | Ala | Ile | Leu | Met | Thr | Leu | Phe | Leu | Phe |
| 1 | | | | 5 | | | | | 10 | | | | | 15 | |

| Ile | Ser | Cys | Asn | Asn | Ser | Gly | Lys | Asp | Gly | Asn | Thr | Ser | Ala | Asn | Ser |
|---|---|---|---|---|---|---|---|---|---|---|---|---|---|---|---|
| | | | | 20 | | | | | 25 | | | | | 30 | |

| Ala | Asp | Glu | Ser | Val | Lys | Gly | Pro | Asn | Leu | Thr | Glu | Ile | Asn | Lys | Lys |
|---|---|---|---|---|---|---|---|---|---|---|---|---|---|---|---|

-continued

```
                    35                  40                  45
Ile Thr Asp Ser Asn Ala Val Leu Leu Ala Val Lys Glu Val Glu Ala
     50                  55                  60

Leu Leu Ser Ser Ile Asp Glu Ile Ala Ala Lys Ala Ile Gly Lys Lys
 65                  70                  75                  80

Ile His Gln Asn Asn Gly Leu Asp Thr Glu Asn Asn His Asn Gly Ser
                 85                  90                  95

Leu Leu Ala Gly Ala Tyr Ala Ile Ser Thr Leu Ile Lys Gln Lys Leu
                100                 105                 110

Asp Gly Leu Lys Asn Glu Gly Leu Lys Glu Lys Ile Asp Ala Ala Lys
            115                 120                 125

Lys Cys Ser Glu Thr Phe Thr Asn Lys Leu Lys Glu Lys His Thr Asp
130                 135                 140

Leu Gly Lys Glu Gly Val Thr Asp Ala Asp Ala Lys Glu Ala Ile Leu
145                 150                 155                 160

Lys Ala Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
                180                 185                 190

Asn Ser Val Lys Glu Leu Thr Ser Pro Val Val Ala Glu Ser Pro Lys
            195                 200                 205

Lys Pro
    210

<210> SEQ ID NO 45
<211> LENGTH: 580
<212> TYPE: DNA
<213> ORGANISM: Borrelia burgdorferi
<220> FEATURE:
<221> NAME/KEY: CDS
<222> LOCATION: (1)...(580)

<400> SEQUENCE: 45 atg gct tgt aat aat tca ggg aaa gat ggg aat aca tct gca aat tct        48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata aat aaa aaa        96
Ala Asp Glu Ser Val Lys Gly Pro Asn Leu Thr Glu Ile Asn Lys Lys
                20                  25                  30 att acg gat tct aat gcg gtt tta ctt gct gtg aaa gag gtt gaa gcg       144
Ile Thr Asp Ser Asn Ala Val Leu Leu Ala Val Lys Glu Val Glu Ala
             35                  40                  45 ttg ctg tca tct ata gat gaa att gct gct aaa gct att ggt aaa aaa       192
Leu Leu Ser Ser Ile Asp Glu Ile Ala Ala Lys Ala Ile Gly Lys Lys
 50                  55                  60 ata cac caa aat aat ggt ttg gat acc gaa aat aat cac aat gga tca       240
Ile His Gln Asn Asn Gly Leu Asp Thr Glu Asn Asn His Asn Gly Ser
 65                  70                  75                  80 ttg tta gcg gga gct tat gca ata tca acc cta ata aaa caa aaa tta       288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag       336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat       384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta       432
```

```
Leu Gly Lys Glu Gly Val Thr Asp Ala Asp Ala Lys Glu Ala Ile Leu
            130                 135                 140 aaa gca aat ggt act aaa act aaa ggt gct gaa gaa ctt gga aaa tta        480
Lys Ala Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct        528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca tcc        576
Asn Ser Val Lys Glu Leu Thr Ser Pro Val Val Ala Glu Ser Pro Ser
            180                 185                 190 atg g                                                                   580
Met

<210> SEQ ID NO 46
<211> LENGTH: 193
<212> TYPE: PRT
<213> ORGANISM: Borrelia burgdorferi

<400> SEQUENCE: 46

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Asn Lys Lys
            20                  25                  30

Ile Thr Asp Ser Asn Ala Val Leu Leu Ala Val Lys Glu Val Glu Ala
        35                  40                  45

Leu Leu Ser Ser Ile Asp Glu Ile Ala Ala Lys Ala Ile Gly Lys Lys
    50                  55                  60

Ile His Gln Asn Asn Gly Leu Asp Thr Glu Asn Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Glu Lys Ile Asp Ala Ala Lys
            100                 105                 110

Lys Cys Ser Glu Thr Phe Thr Asn Lys Leu Lys Glu Lys His Thr Asp
        115                 120                 125

Leu Gly Lys Glu Gly Val Thr Asp Ala Asp Ala Lys Glu Ala Ile Leu
    130                 135                 140

Lys Ala Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Ser
            180                 185                 190

Met

<210> SEQ ID NO 47
<211> LENGTH: 639
<212> TYPE: DNA
<213> ORGANISM: Borrelia garinii
<220> FEATURE:
<221> NAME/KEY: CDS
<222> LOCATION: (1)...(639)

<400> SEQUENCE: 47 at

```
ata tct tgt agt aat tca ggg aaa ggt ggg gat tct gca t

```
                  100                 105                 110
Leu Ser Lys Leu Lys Asn Leu Glu Glu Leu Lys Thr Glu Ile Ala Lys
            115                 120                 125

Ala Lys Lys Cys Ser Glu Glu Phe Thr Asn Lys Leu Lys Ser Gly His
        130                 135                 140

Ala Asp Leu Gly Lys Gln Asp Ala Thr Asp His Ala Lys Ala Ala
145                 150                 155                 160

Ile Leu Lys Thr His Ala Thr Thr Asp Lys Gly Ala Lys Glu Phe Lys
                165                 170                 175

Asp Leu Phe Glu Ser Val Glu Gly Leu Leu Lys Ala Ala Gln Val Ala
            180                 185                 190

Leu Thr Asn Ser Val Lys Glu Leu Thr Ser Pro Val Val Ala Glu Ser
        195                 200                 205

Pro Lys Lys Pro
    210

<210> SEQ ID NO 49
<211> LENGTH: 624
<212> TYPE: DNA
<213> ORGANISM: Borrelia afzelii
<220> FEATURE:
<221> NAME/KEY: CDS
<222> LOCATION: (1)...(624)

<400> SEQUENCE: 49 atg aaa aag a

```
Leu Glu Ser Leu Ser Lys Ala Ala Gln Ala Ala Leu Thr Asn Ser Val
        180                 185                 190 aaa gag ctt aca aat cct gtt gtg gca gaa agt cca aaa aaa cct taa       624
Lys Glu Leu Thr Asn Pro Val Val Ala Glu Ser Pro Lys Lys Pro *
        195                 200                 205

<210> SEQ ID NO 50
<211> LENGTH: 207
<212> TYPE: PRT
<213> ORGANISM: Borrelia afzelii

<400> SEQUENCE: 50

Met Lys Lys Asn Thr Leu Ser Ala Ile Leu Met Thr Leu Phe Leu Phe
 1               5                  10                  15

Ile Ser Cys Asn Asn Ser Gly Gly Asp Ser Ala Ser Thr Asn Pro Asp
            20                  25                  30

Glu Ser Ala Lys Gly Pro Asn Leu Thr Val Ile Ser Lys Lys Ile Thr
        35                  40                  45

Asp Ser Asn Ala Phe Leu Leu Ala Val Lys Glu Val Glu Ala Leu Leu
    50                  55                  60

Ser Ser Ile Asp Glu Leu Ser Lys Ala Ile Gly Lys Lys Ile Lys Asn
65                  70                  75                  80

Asp Gly Thr Leu Asp Asn Glu Ala Asn Arg Asn Glu Ser Leu Ile Ala
                85                  90                  95

Gly Ala Tyr Glu Ile Ser Lys Leu Ile Thr Gln Lys Leu Ser Val Leu
            100                 105                 110

Asn Ser Glu Glu Leu Lys Lys Lys Ile Lys Glu Ala Lys Asp Cys Ser
        115                 120                 125

Gln Lys Phe Thr Thr Lys Leu Lys Asp Ser His Ala Glu Leu Gly Ile
    130                 135                 140

Gln Ser Val Gln Asp Asp Asn Ala Lys Lys Ala Ile Leu Lys Thr His
145                 150                 155                 160

Gly Thr Lys Asp Lys Gly Ala Lys Glu Leu Glu Leu Phe Lys Ser
                165                 170                 175

Leu Glu Ser Leu Ser Lys Ala Ala Gln Ala Ala Leu Thr Asn Ser Val
        180                 185                 190

Lys Glu Leu Thr Asn Pro Val Val Ala Glu Ser Pro Lys Lys Pro
        195                 200                 205

<210> SEQ ID NO 51
<211> LENGTH: 1680
<212> TYPE: DNA
<213> ORGANISM: ospC Chimera
<220> FEATURE:
<221> NAME/KEY: CDS
<222> LOCATION: (1)...(1680)

<400> SEQUENCE: 51 atg gct tgt aat aat tca ggg aaa gat ggg aat aca tct gca aat tct       48
Met Ala Cys Asn Asn Ser Gly Lys Asp Gly Asn Thr Ser Ala Asn Ser
 1               5                  10                  15 gct gat gag tct gtt aaa ggg cct aat ctt aca gaa ata agt aaa aaa       96
Ala Asp Glu Ser Val Lys Gly Pro Asn Leu Thr Glu Ile Ser Lys Lys
            20                  25                  30 att acg gat tct aat gcg gtt tta ctt gct gtg aaa gag gtt gaa gcg      144
Ile Thr Asp Ser Asn Ala Val Leu Leu Ala Val Lys Glu Val Glu Ala
        35                  40                  45 ttg ctg tca tct ata gat gaa att gct gct aaa gct att ggt aaa aaa      192
Leu Leu Ser Ser Ile Asp Glu Ile Ala Ala Lys Ala Ile Gly Lys Lys
```

```
            50                  55                  60
ata cac caa aat aat ggt ttg gat acc gaa tat aat cac aat gga tca      240
Ile His Gln Asn Asn Gly Leu Asp Thr Glu Tyr Asn His Asn Gly Ser
 65                  70                  75                  80 ttg tta gcg gga gct tat gca ata tca acc cta ata aaa caa aaa tta      288
Leu Leu Ala Gly Ala Tyr Ala Ile Ser Thr Leu Ile Lys Gln Lys Leu
                 85                  90                  95 gat gga ttg aaa aat gaa gga tta aag gaa aaa att gat gcg gct aag      336
Asp Gly Leu Lys Asn Glu Gly Leu Lys Glu Lys Ile Asp Ala Ala Lys
            100                 105                 110 aaa tgt tct gaa aca ttt act aat aaa tta aaa gaa aaa cac aca gat      384
Lys Cys Ser Glu Thr Phe Thr Asn Lys Leu Lys Glu Lys His Thr Asp
        115                 120                 125 ctt ggt aaa gaa ggt gtt act gat gct gat gca aaa gaa gcc att tta      432
Leu Gly Lys Glu Gly Val Thr Asp Ala Asp Ala Lys Glu Ala Ile Leu
    130                 135                 140 aaa aca aat ggt act aaa act aaa ggt gct gaa gaa ctt gga aaa tta      480
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct      528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca gcc      576
Asn Ser Val Lys Glu Leu Thr Ser Pro Val Val Ala Glu Ser Pro Ala
            180                 185                 190 atg ggt agt aat tca ggg aaa ggt ggg gat tct gca tct act aat cct      624
Met Gly Ser Asn Ser Gly Lys Gly Gly Asp Ser Ala Ser Thr Asn Pro
        195                 200                 205 gct gac gag tct gcg aaa ggg cct aat ctt aca gaa ata agc aaa aaa      672
Ala Asp Glu Ser Ala Lys Gly Pro Asn Leu Thr Glu Ile Ser Lys Lys
    210                 215                 220 att aca gat tct aat gca ttt gta ctt gct gtt aaa gaa gtt gag act      720
Ile Thr Asp Ser Asn Ala Phe Val Leu Ala Val Lys Glu Val Glu Thr
225                 230                 235                 240 ttg gtt tta tct ata gat gaa ctt gct aag aaa gct att ggt caa aaa      768
Leu Val Leu Ser Ile Asp Glu Leu Ala Lys Lys Ala Ile Gly Gln Lys
                245                 250                 255 ata gac aat aat aat ggt tta gct gct tta aat aat cag aat gga tcg      816
Ile Asp Asn Asn Asn Gly Leu Ala Ala Leu Asn Asn Gln Asn Gly Ser
            260                 265                 270 ttg tta gca gga gcc tat gca ata tca acc cta ata aca gaa aaa ttg      864
Leu Leu Ala Gly Ala Tyr Ala Ile Ser Thr Leu Ile Thr Glu Lys Leu
        275                 280                 285 agt aaa ttg aaa aat tta gaa gaa tta aag aca gaa att gca aag gct      912
Ser Lys Leu Lys Asn Leu Glu Glu Leu Lys Thr Glu Ile Ala Lys Ala
    290                 295                 300 aag aaa tgt tcc gaa gaa ttt act aat aaa cta aaa agt ggt cat gca      960
Lys Lys Cys Ser Glu Glu Phe Thr Asn Lys Leu Lys Ser Gly His Ala
305                 310                 315                 320 gat ctt ggc aaa cag gat gct acc gat gat cat gca aaa gca gct att     1008
Asp Leu Gly Lys Gln Asp Ala Thr Asp Asp His Ala Lys Ala Ala Ile
                325                 330                 335 tta aaa aca cat gca act acc gat aaa ggt gct aaa gaa ttt aaa gat     1056
Leu Lys Thr His Ala Thr Thr Asp Lys Gly Ala Lys Glu Phe Lys Asp
            340                 345                 350 tta ttt gaa tca gta gaa ggt ttg tta aaa gca gct caa gta gca cta     1104
Leu Phe Glu Ser Val Glu Gly Leu Leu Lys Ala Ala Gln Val Ala Leu
        355                 360                 365 act aat tca gtt aaa gaa ctt ggt cac cgt aat aat tca ggt ggg gat     1152
```

```
Thr Asn Ser Val Lys Glu Leu Gly His Arg Asn Asn Ser Gly Gly Asp
    370                 375                 380 tct gca tct act aat cct gat gag tct gca aaa gga cct aat ctt acc    1200
Ser Ala Ser Thr Asn Pro Asp Glu Ser Ala Lys Gly Pro Asn Leu Thr
385                 390                 395                 400 gta ata agc aaa aaa att aca gat tct aat gca ttt tta ctg gct gtg    1248
Val Ile Ser Lys Lys Ile Thr Asp Ser Asn Ala Phe Leu Leu Ala Val
                405                 410                 415 aaa gaa gtt gag gct ttg ctt tca tct ata gat gaa ctt tct aaa gct    1296
Lys Glu Val Glu Ala Leu Leu Ser Ser Ile Asp Glu Leu Ser Lys Ala
            420                 425                 430 att ggt aaa aaa ata aaa aat gat ggt act tta gat aac gaa gca aat    1344
Ile Gly Lys Lys Ile Lys Asn Asp Gly Thr Leu Asp Asn Glu Ala Asn
        435                 440                 445 cga aac gaa tca ttg ata gca gga gct tat gaa ata tca aaa cta ata    1392
Arg Asn Glu Ser Leu Ile Ala Gly Ala Tyr Glu Ile Ser Lys Leu Ile
    450                 455                 460 aca caa aaa tta agt gta ttg aat tca gaa gaa tta aag aaa aaa att    1440
Thr Gln Lys Leu Ser Val Leu Asn Ser Glu Glu Leu Lys Lys Lys Ile
465                 470                 475                 480 aaa gag gct aag gat tgt tcc caa aaa ttt act act aag cta aaa gat    1488
Lys Glu Ala Lys Asp Cys Ser Gln Lys Phe Thr Thr Lys Leu Lys Asp
                485                 490                 495 agt cat gca gag ctt ggt ata caa agc gtt cag gat gat aat gca aaa    1536
Ser His Ala Glu Leu Gly Ile Gln Ser Val Gln Asp Asp Asn Ala Lys
            500                 505                 510 aaa gct att tta aaa aca cat gga act aaa gac aag ggt gct aaa gaa    1584
Lys Ala Ile Leu Lys Thr His Gly Thr Lys Asp Lys Gly Ala Lys Glu
        515                 520                 525 ctt gaa gag tta ttt aaa tca cta gaa agc ttg tca aaa gca gcg caa    1632
Leu Glu Glu Leu Phe Lys Ser Leu Glu Ser Leu Ser Lys Ala Ala Gln
    530                 535                 540 gca gca tta act aat tca gtt aaa gag ctt aca aat cct gtt gtg gca    1680
Ala Ala Leu Thr Asn Ser Val Lys Glu Leu Thr Asn Pro Val Val Ala
545                 550                 555                 560

<210> SEQ ID NO 52
<211> LENGTH: 560
<212> TYPE: PRT
<213> ORGANISM: ospC Chimera

<400> SEQUENCE: 52

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
                20                  25                  30

Ile Thr Asp Ser Asn Ala Val Leu Leu Ala Val Lys Glu Val Glu Ala
            35                  40                  45

Leu Leu Ser Ser Ile Asp Glu Ile Ala Ala Lys Ala Ile Gly Lys Lys
        50                  55                  60

Ile His Gln Asn Asn Gly Leu Asp Thr Glu Tyr Asn His Asn Gly Ser
65                  70                  75                  80

Leu Leu Ala Gly Ala Tyr Ala Ile Ser Thr Leu Ile Lys Gln Lys Leu
                85                  90                  95

Asp Gly Leu Lys Asn Glu Gly Leu Lys Glu Lys Ile Asp Ala Ala Lys
            100                 105                 110

Lys Cys Ser Glu Thr Phe Thr Asn Lys Leu Lys Glu Lys His Thr Asp
        115                 120                 125
```

-continued

```
Leu Gly Lys Glu Gly Val Thr Asp Ala Asp Ala Lys Glu Ala Ile Leu
    130                 135                 140

Lys Thr Asn Gly Thr Lys Thr Lys Gly Ala Glu Glu Leu Gly Lys Leu
145                 150                 155                 160

Phe Glu Ser Val Glu Val Leu Ser Lys Ala Ala Lys Glu Met Leu Ala
                165                 170                 175

Asn Ser Val Lys Glu Leu Thr Ser Pro Val Val Ala Glu Ser Pro Ala
                180                 185                 190

Met Gly Ser Asn Ser Gly Lys Gly Gly Asp Ser Ala Ser Thr Asn Pro
            195                 200                 205

Ala Asp Glu Ser Ala Lys Gly Pro Asn Leu Thr Glu Ile Ser Lys Lys
    210                 215                 220

Ile Thr Asp Ser Asn Ala Phe Val Leu Ala Val Lys Glu Val Glu Thr
225                 230                 235                 240

Leu Val Leu Ser Ile Asp Glu Leu Ala Lys Lys Ala Ile Gly Gln Lys
                245                 250                 255

Ile Asp Asn Asn Asn Gly Leu Ala Ala Leu Asn Asn Gln Asn Gly Ser
            260                 265                 270

Leu Leu Ala Gly Ala Tyr Ala Ile Ser Thr Leu Ile Thr Glu Lys Leu
    275                 280                 285

Ser Lys Leu Lys Asn Leu Glu Glu Leu Lys Thr Glu Ile Ala Lys Ala
290                 295                 300

Lys Lys Cys Ser Glu Glu Phe Thr Asn Lys Leu Lys Ser Gly His Ala
305                 310                 315                 320

Asp Leu Gly Lys Gln Asp Ala Thr Asp His Ala Lys Ala Ala Ile
                325                 330                 335

Leu Lys Thr His Ala Thr Thr Asp Lys Gly Ala Lys Glu Phe Lys Asp
            340                 345                 350

Leu Phe Glu Ser Val Glu Gly Leu Leu Lys Ala Ala Gln Val Ala Leu
    355                 360                 365

Thr Asn Ser Val Lys Glu Leu Gly His Arg Asn Asn Ser Gly Gly Asp
370                 375                 380

Ser Ala Ser Thr Asn Pro Asp Glu Ser Ala Lys Gly Pro Asn Leu Thr
385                 390                 395                 400

Val Ile Ser Lys Lys Ile Thr Asp Ser Asn Ala Phe Leu Leu Ala Val
                405                 410                 415

Lys Glu Val Glu Ala Leu Leu Ser Ser Ile Asp Glu Leu Ser Lys Ala
            420                 425                 430

Ile Gly Lys Lys Ile Lys Asn Asp Gly Thr Leu Asp Asn Glu Ala Asn
    435                 440                 445

Arg Asn Glu Ser Leu Ile Ala Gly Ala Tyr Glu Ile Ser Lys Leu Ile
450                 455                 460

Thr Gln Lys Leu Ser Val Leu Asn Ser Glu Glu Leu Lys Lys Lys Ile
465                 470                 475                 480

Lys Glu Ala Lys Asp Cys Ser Gln Lys Phe Thr Thr Lys Leu Lys Asp
                485                 490                 495

Ser His Ala Glu Leu Gly Ile Gln Ser Val Gln Asp Asn Ala Lys
            500                 505                 510

Lys Ala Ile Leu Lys Thr His Gly Thr Lys Asp Lys Gly Ala Lys Glu
    515                 520                 525

Leu Glu Glu Leu Phe Lys Ser Leu Glu Ser Leu Ser Lys Ala Ala Gln
530                 535                 540

Ala Ala Leu Thr Asn Ser Val Lys Glu Leu Thr Asn Pro Val Val Ala
```

<210> SEQ ID NO 53
<211> LENGTH: 1137
<212> TYPE: DNA
<213> ORGANISM: ospC Chimera
<220> FEATURE:
<221> NAME/KEY: CDS
<222> LOCATION: (1)...(1137)

<400> SEQUENCE: 53

| | | | | | | | | | | | | | | | | |
|---|---|---

```
                              260                  265                  270
tca aaa cta ata aca caa aaa tta agt gta ttg aat tca gaa gaa tta           864
Ser Lys Leu Ile Thr Gln Lys Leu Ser Val Leu Asn Ser Glu Glu Leu
        275                  280                  285 aag aaa aaa att aaa gag gct aag gat tgt tcc caa aaa ttt act act           912
Lys Lys Lys Ile Lys Glu Ala Lys Asp Cys Ser Gln Lys Phe Thr Thr
        290                  295                  300 aag cta aaa gat agt cat gca gag ctt ggt ata caa agc gtt cag gat           960
Lys Leu Lys Asp Ser His Ala Glu Leu Gly Ile Gln Ser Val Gln Asp
305                  310                  315                  320 gat aat gca aaa aaa gct att tta aaa aca cat gga act aaa gac aag          1008
Asp Asn Ala Lys Lys Ala Ile Leu Lys Thr His Gly Thr Lys Asp Lys
                325                  330                  335 ggt gct aaa gaa ctt gaa gag tta ttt aaa tca cta gaa agc ttg tca          1056
Gly Ala Lys Glu Leu Glu Glu Leu Phe Lys Ser Leu Glu Ser Leu Ser
        340                  345                  350 aaa gca gcg caa gca gca tta act aat tca gtt aaa gag ctt aca aat          1104
Lys Ala Ala Gln Ala Ala Leu Thr Asn Ser Val Lys Glu Leu Thr Asn
        355                  360                  365 cct gtt gtg gca gaa agt cca aaa aaa cct taa                             1137
Pro Val Val Ala Glu Ser Pro Lys Lys Pro  *
        370                  375

<210> SEQ ID NO 54
<211> LENGTH: 378
<212> TYPE: PRT
<213> ORGANISM: ospC Chimera

<400> SEQUENCE: 54

Met Ala Cys Asn Asn Ser Gly Lys Asp Gly Asn Thr Ser Ala Asn Ser
 1               5                   10                  15

Ala Asp Glu Ser Val Lys Gly Pro Asn Leu Thr Glu Ile Ser Lys Lys
             20                  25                  30

Ile Thr Asp

```
Leu Leu Ala Val Lys Glu Val Glu Ala Leu Leu Ser Ser Ile Asp Glu
225                 230                 235                 240

Leu Ser Lys Ala Ile Gly Lys Lys Ile Lys Asn Asp Gly Thr Leu Asp
            245                 250                 255

Asn Glu Ala Asn Arg Asn Glu Ser Leu Ile Ala Gly Ala Tyr Glu Ile
            260                 265                 270

Ser Lys Leu Ile Thr Gln Lys Leu Ser Val Leu Asn Ser Glu Glu Leu
        275                 280                 285

Lys Lys Lys Ile Lys Glu Ala Lys Asp Cys Ser Gln Lys Phe Thr Thr
290                 295                 300

Lys Leu Lys Asp Ser His Ala Glu Leu Gly Ile Gln Ser Val Gln Asp
305                 310                 315                 320

Asp Asn Ala Lys Lys Ala Ile Leu Lys Thr His Gly Thr Lys Asp Lys
                325                 330                 335

Gly Ala Lys Glu Leu Glu Glu Leu Phe Lys Ser Leu Glu Ser Leu Ser
            340                 345                 350

Lys Ala Ala Gln Ala Ala Leu Thr Asn Ser Val Lys Glu Leu Thr Asn
        355                 360                 365

Pro Val Val Ala Glu Ser Pro Lys Lys Pro
370                 375

<210> SEQ ID NO 55
<211> LENGTH: 1158
<212> TYPE: DNA
<213> ORGANISM: ospC Chimera
<220> FEATURE:

```
Lys Thr Asn Gly Thr Lys Thr Lys Gly Ala Glu Glu Leu Gly Lys Leu
145                 150                 155                 160 ttt gaa tca gta gag gtc ttg tca aaa gca gct aaa gag atg ctt gct    528
Phe Glu Ser Val Glu Val Leu Ser Lys Ala Ala Lys Glu Met Leu Ala
                165                 170                 175 aat tca gtt aaa gag ctt aca agc cct gtt gtg gca gaa agt cca aaa    576
Asn Ser Val Lys Glu Leu Thr Ser Pro Val Val Ala Glu Ser Pro Lys
            180                 185                 190 aaa cct ttc cat ggt aat aat tca ggt ggg gat tct gca tct act aat    624
Lys Pro Phe His Gly Asn Asn Ser Gly Gly Asp Ser Ala Ser Thr Asn
        195                 200                 205 cct gat gag tct gca aaa gga cct aat ctt acc gta ata agc aaa aaa    672
Pro Asp Glu Ser Ala Lys Gly Pro Asn Leu Thr Val Ile Ser Lys Lys
    210                 215                 220 att aca gat tct aat gca ttt tta ctg gct gtg aaa gaa gtt gag gct    720
Ile Thr Asp Ser Asn Ala Phe Leu Leu Ala Val Lys Glu Val Glu Ala
225                 230                 235                 240 ttg ctt tca tct ata gat gaa ctt tct aaa gct att ggt aaa aaa ata    768
Leu Leu Ser Ser Ile Asp Glu Leu Ser Lys Ala Ile Gly Lys Lys Ile
                245                 250                 255 aaa aat gat ggt act tta gat aac gaa gca aat cga aac gaa tca ttg    816
Lys Asn Asp Gly Thr Leu Asp Asn Glu Ala Asn Arg Asn Glu Ser Leu
            260                 265                 270 ata gca gga gct tat gaa ata tca aaa cta ata aca caa aaa tta agt    864
Ile Ala Gly Ala Tyr Glu Ile Ser Lys Leu Ile Thr Gln Lys Leu Ser
        275                 280                 285 gta ttg aat tca gaa gaa tta aag aaa aaa att aaa gag gct aag gat    912
Val Leu Asn Ser Glu Glu Leu Lys Lys Lys Ile Lys Glu Ala Lys Asp
    290                 295                 300 tgt tcc caa aaa ttt act act aag cta aaa gat agt cat gca gag ctt    960
Cys Ser Gln Lys Phe Thr Thr Lys Leu Lys Asp Ser His Ala Glu Leu
305                 310                 315                 320 ggt ata caa agc gtt cag gat gat aat gca aaa aaa gct att tta aaa    1008
Gly Ile Gln Ser Val Gln Asp Asp Asn Ala Lys Lys Ala Ile Leu Lys
                325                 330                 335 aca cat gga act aaa gac aag ggt gct aaa gaa ctt gaa gag tta ttt    1056
Thr His Gly Thr Lys Asp Lys Gly Ala Lys Glu Leu Glu Glu Leu Phe
            340                 345                 350 aaa tca cta gaa agc ttg tca aaa gca gcg caa gca gca tta act aat    1104
Lys Ser Leu Glu Ser Leu Ser Lys Ala Ala Gln Ala Ala Leu Thr Asn
        355                 360                 365 tca gtt aaa gag ctt aca aat cct gtt gtg gca gaa agt cca aaa aaa    1152
Ser Val Lys Glu Leu Thr Asn Pro Val Val Ala Glu Ser Pro Lys Lys
    370                 375                 380 cct taa                                                            1158
Pro *
385

<210> SEQ ID NO 56
<211> LENGTH: 385
<212> TYPE: PRT
<213> ORGANISM: ospC Chimera

<400> SEQUENCE: 56

Met Ala Cys Asn Asn Ser Gly Lys Asp Gly Asn Thr Ser Ala Asn Ser
1               5                   10                  15

Ala Asp Glu Ser Val Lys Gly Pro Asn Leu Thr Glu Ile Ser Lys Lys
            20                  25                  30

Ile Thr Asp Ser Asn Ala Val Leu Leu Ala Val Lys Glu Val Glu Ala
        35                  40                  45
```

```
Leu Leu Ser Ser Ile Asp Glu Ile Ala Ala Lys Ala Ile Gly Lys Lys
     50                  55                  60
Ile His Gln Asn Asn Gly Leu Asp Thr Glu Tyr Asn His Asn Gly Ser
 65                  70                  75                  80
Leu Leu Ala Gly Ala Tyr Ala Ile Ser Thr Leu Ile Lys Gln Lys Leu
                 85                  90                  95
Asp Gly Leu Lys Asn Glu Gly Leu Lys Glu Lys Ile Asp Ala Ala Lys
            100                 105                 110
Lys Cys Ser Glu Thr Phe Thr Asn Lys Leu Lys Glu Lys His Thr Asp
            115                 120                 125
Leu Gly Lys Glu Gly Val Thr Asp Ala Asp Ala Lys Glu Ala Ile Leu
            130                 135                 140
Lys Thr Asn Gly Thr Lys Thr Lys Gly Ala Glu Glu Leu Gly Lys Leu
145                 150                 155                 160
Phe Glu Ser Val Glu Val Leu Ser Lys Ala Ala Lys Glu Met Leu Ala
                165                 170                 175
Asn Ser Val Lys Glu Leu Thr Ser Pro Val Val Ala Glu Ser Pro Lys
            180                 185                 190
Lys Pro Phe His Gly Asn Asn Ser Gly Gly Asp Ser Ala Ser Thr Asn
            195                 200                 205
Pro Asp Glu Ser Ala Lys Gly Pro Asn Leu Thr Val Ile Ser Lys Lys
210                 215                 220
Ile Thr Asp Ser Asn Ala Phe Leu Leu Ala Val Lys Glu Val Glu Ala
225                 230                 235                 240
Leu Leu Ser Ser Ile Asp Glu Leu Ser Lys Ala Ile Gly Lys Lys Ile
                245                 250                 255
Lys Asn Asp Gly Thr Leu Asp Asn Glu Ala Asn Arg Asn Glu Ser Leu
            260                 265                 270
Ile Ala Gly Ala Tyr Glu Ile Ser Lys Leu Ile Thr Gln Lys Leu Ser
            275                 280                 285
Val Leu Asn Ser Glu Glu Leu Lys Lys Ile Lys Glu Ala Lys Asp
            290                 295                 300
Cys Ser Gln Lys Phe Thr Thr Lys Leu Lys Asp Ser His Ala Glu Leu
305                 310                 315                 320
Gly Ile Gln Ser Val Gln Asp Asp Asn Ala Lys Lys Ala Ile Leu Lys
                325                 330                 335
Thr His Gly Thr Lys Asp Lys Gly Ala Lys Glu Leu Glu Gly Leu Phe
            340                 345                 350
Lys Ser Leu Glu Ser Leu Ser Lys Ala Ala Gln Ala Ala Leu Thr Asn
            355                 360                 365
Ser Val Lys Glu Leu Thr Asn Pro Val Val Ala Glu Ser Pro Lys Lys
            370                 375                 380
Pro
385

<210> SEQ ID NO 57
<211> LENGTH: 1161
<212> TYPE: DNA
<213> ORGANISM: ospC Chimera
<220> FEATURE:
<221> NAME/KEY: CDS
<222> LOCATION: (1)...(1161)

<400> SEQUENCE: 57 atg tgt agt aat tca ggg aaa ggt ggg gat tct gca tct act aat cct      48
```

```
Met Cys Ser Asn Ser Gly Lys Gly Gly Asp Ser Ala Ser Thr Asn Pro
 1               5                  10                 15 gct gac gag tct gcg aaa ggg cct aat ctt aca gaa ata agc aaa aaa      96
Ala Asp Glu Ser Ala Lys Gly Pro Asn Leu Thr Glu Ile Ser Lys Lys
            20                  25                  30 att aca gat tct aat gca ttt gta ctt gct gtt aaa gaa gtt gag act     144
Ile Thr Asp Ser Asn Ala Phe Val Leu Ala Val Lys Glu Val Glu Thr
         35                  40                  45 ttg gtt tta tct ata gat gaa ctt gct aag aaa gct att ggt caa aaa     192
Leu Val Leu Ser Ile Asp Glu Leu Ala Lys Lys Ala Ile Gly Gln Lys
     50                  55                  60 ata gac aat aat aat ggt tta gct gct tta aat aat cag aat gga tcg     240
Ile Asp Asn Asn Asn Gly Leu Ala Ala Leu Asn Asn Gln Asn Gly Ser
 65                  70                  75                  80 ttg tta gca gga gcc tat gca ata tca acc cta ata aca gaa aaa ttg     288
Leu Leu Ala Gly Ala Tyr Ala Ile Ser Thr Leu Ile Thr Glu Lys Leu
                 85                  90                  95 agt aaa ttg aaa aat tta gaa gaa tta aag aca gaa att gca aag gct     336
Ser Lys Leu Lys Asn Leu Glu Glu Leu Lys Thr Glu Ile Ala Lys Ala
            100                 105                 110 aag aaa tgt tcc gaa gaa ttt act aat aaa cta aaa agt ggt cat gca     384
Lys Lys Cys Ser Glu Glu Phe Thr Asn Lys Leu Lys Ser Gly His Ala
        115                 120                 125 gat ctt ggc aaa cag gat gct acc gat gat cat gca aaa gca gct att     432
Asp Leu Gly Lys Gln Asp Ala Thr Asp Asp His Ala Lys Ala Ala Ile
    130                 135                 140 tta aaa aca cat gca act acc gat aaa ggt gct aaa gaa ttt aaa gat     480
Leu Lys Thr His Ala Thr Thr Asp Lys Gly Ala Lys Glu Phe Lys Asp
145                 150                 155                 160 tta ttt gaa tca gta gaa ggt ttg tta aaa gca gct caa gta gca cta     528
Leu Phe Glu Ser Val Glu Gly Leu Leu Lys Ala Ala Gln Val Ala Leu
                165                 170                 175 act aat tca gtt aaa gaa ctt aca agt cct gtt gta gca gaa agt cca     576
Thr Asn Ser Val Lys Glu Leu Thr Ser Pro Val Val Ala Glu Ser Pro
            180                 185                 190 aaa aaa cct cat atg gct aat aat tca ggt ggg gat tct gca tct act     624
Lys Lys Pro His Met Ala Asn Asn Ser Gly Gly Asp Ser Ala Ser Thr
        195                 200                 205 aat cct gat gag tct gca aaa gga cct aat ctt acc gta ata agc aaa     672
Asn Pro Asp Glu Ser Ala Lys Gly Pro Asn Leu Thr Val Ile Ser Lys
    210                 215                 220 aaa att aca gat tct aat gca ttt tta ctg gct gtg aaa gaa gtt gag     720
Lys Ile Thr Asp Ser Asn Ala Phe Leu Leu Ala Val Lys Glu Val Glu
225                 230                 235                 240 gct ttg ctt tca tct ata gat gaa ctt tct aaa gct att ggt aaa aaa     768
Ala Leu Leu Ser Ser Ile Asp Glu Leu Ser Lys Ala Ile Gly Lys Lys
                245                 250                 255 ata aaa aat gat ggt act tta gat aac gaa gca aat cga aac gaa tca     816
Ile Lys Asn Asp Gly Thr Leu Asp Asn Glu Ala Asn Arg Asn Glu Ser
            260                 265                 270 ttg ata gca gga gct tat gaa ata tca aaa cta ata aca caa aaa tta     864
Leu Ile Ala Gly Ala Tyr Glu Ile Ser Lys Leu Ile Thr Gln Lys Leu
        275                 280                 285 agt gta ttg aat tca gaa gaa tta aag aaa aaa att aaa gag gct aag     912
Ser Val Leu Asn Ser Glu Glu Leu Lys Lys Lys Ile Lys Glu Ala Lys
    290                 295                 300 gat tgt tcc caa aaa ttt act act aag cta aaa gat agt cat gca gag     960
Asp Cys Ser Gln Lys Phe Thr Thr Lys Leu Lys Asp Ser His Ala Glu
305                 310                 315                 320
```

```
ctt ggt ata caa agc gtt cag gat gat aat gca aaa aaa gct att tta      1008
Leu Gly Ile Gln Ser Val Gln Asp Asp Asn Ala Lys Lys Ala Ile Leu
            325                 330                 335 aaa aca cat gga act aaa gac aag ggt gct aaa gaa ctt gaa gag tta      1056
Lys Thr His Gly Thr Lys Asp Lys Gly Ala Lys Glu Leu Glu Glu Leu
        340                 345                 350 ttt aaa tca cta gaa agc ttg tca aaa gca gcg caa gca gca tta act      1104
Phe Lys Ser Leu Glu Ser Leu Ser Lys Ala Ala Gln Ala Ala Leu Thr
                355                 360                 365 aat tca gtt aaa gag ctt aca aat cct gtt gtg gca gaa agt cca aaa      1152
Asn Ser Val Lys Glu Leu Thr Asn Pro Val Val Ala Glu Ser Pro Lys
            370                 375                 380 aaa cct taa                                                           1161
Lys Pro *
385

<210> SEQ ID NO 58
<211> LENGTH: 386
<212> TYPE: PRT
<213> ORGANISM: ospC Chimera

<400> SEQUENCE: 58

Met Cys Ser Asn Ser Gly Lys Gly Gly Asp Ser Ala Ser Thr Asn Pro
 1               5                  10                  15

Ala Asp Glu Ser Ala Lys Gly Pro Asn Leu Thr Glu Ile Ser Lys Lys
             20                  25                  30

Ile Thr Asp Ser Asn Ala Phe Val Leu Ala Val Lys Glu Val

```
Leu Ile Ala Gly Ala Tyr Glu Ile Ser Lys Leu Ile Thr Gln Lys Leu
            275                 280                 285

Ser Val Leu Asn Ser Glu Glu Leu Lys Lys Lys Ile Lys Glu Ala Lys
            290                 295                 300

Asp Cys Ser Gln Lys Phe Thr Lys Leu Lys Asp Ser His Ala Glu
305                 310                 315                 320

Leu Gly Ile Gln Ser Val Gln Asp Asp Asn Ala Lys Lys Ala Ile Leu
                    325                 330                 335

Lys Thr His Gly Thr Lys Asp Lys Gly Ala Lys Glu Leu Glu Glu Leu
                340                 345                 350

Phe Lys Ser Leu Glu Ser Leu Ser Lys Ala Ala Gln Ala Ala Leu Thr
            355                 360                 365

Asn Ser Val Lys Glu Leu Thr Asn Pro Val Val Ala Glu Ser Pro Lys
            370                 375                 380

Lys Pro
385

<210> SEQ ID NO 59
<211> LENGTH: 1197
<212> TYPE: DNA
<213> ORGANISM: ospC Chimera
<220> FEATURE:
<221> NAME/KEY: CDS
<222> LOCATION: (1)...(1197)

<400> SEQUENCE: 59 atg aga tta tta ata gga ttt gct tta gcg tta gct tta ata gga tgt      48
Met Arg Leu Leu Ile Gly Phe Ala Leu Ala Leu Ala Leu Ile Gly Cys
  1               5                  10                  15 gca caa aaa ggt gct gag tca att gga tcc tg

-continued

| | | |
|---|---|---|
| ggt gct gaa gaa ctt gga aaa tta ttt gaa tca gta gag gtc ttg tca<br>Gly Ala Glu Glu Leu Gly Lys Leu Phe Glu Ser Val Glu Val Leu Ser<br>              180                        185                    190 | 576 |

```
ggt gct gaa gaa ctt gga aaa tta ttt gaa tca gta gag gtc ttg tca      576
Gly Ala Glu Glu Leu Gly Lys Leu Phe Glu Ser Val Glu Val Leu Ser
            180                 185                 190 aaa gca gct aaa gag atg ctt gct aat tca gtt aaa gag ctt aca agc      624
Lys Ala Ala Lys Glu Met Leu Ala Asn Ser Val Lys Glu Leu Thr Ser
            195                 200                 205 cct gtt gtg gca gaa agt cca gcc atg gta aat aat tca ggg aaa gat      672
Pro Val Val Ala Glu Ser Pro Ala Met Val Asn Asn Ser Gly Lys Asp
210                 215                 220 ggg aat aca tct gca aat tct gct gat gag tct gtt aaa ggg cct aat      720
Gly Asn Thr Ser Ala Asn Ser Ala Asp Glu Ser Val Lys Gly Pro Asn
225                 230                 235                 240 ctt aca gaa ata agt aaa aaa att aca gaa tct aac gca gtt gtt ctc      768
Leu Thr Glu Ile Ser Lys Lys Ile Thr Glu Ser Asn Ala Val Val Leu
            245                 250                 255 gcc gtg aaa gaa gtt gaa act ttg ctt aca tct ata gat gag ctt gct      816
Ala Val Lys Glu Val Glu Thr Leu Leu Thr Ser Ile Asp Glu Leu Ala
            260                 265                 270 aaa gct att ggt aaa aaa ata aaa aac gat gtt agt tta gat aat gag      864
Lys Ala Ile Gly Lys Lys Ile Lys Asn Asp Val Ser Leu Asp Asn Glu
            275                 280                 285 gca gat cac aac gga tca tta ata tca gga gca tat tta att tca aac      912
Ala Asp His Asn Gly Ser Leu Ile Ser Gly Ala Tyr Leu Ile Ser Asn
290                 295                 300 tta ata aca aaa aaa ata agt gca ata aaa gat tca gga gaa ttg aag      960
Leu Ile Thr Lys Lys Ile Ser Ala Ile Lys Asp Ser Gly Glu Leu Lys
305                 310                 315                 320 gca gaa att gaa aag gct aag aaa tgt tct gaa gaa ttt act gct aaa     1008
Ala Glu Ile Glu Lys Ala Lys Lys Cys Ser Glu Glu Phe Thr Ala Lys
            325                 330                 335 tta aaa ggt gaa cac aca gat ctt ggt aaa gaa ggc gtt act gat gat     1056
Leu Lys Gly Glu His Thr Asp Leu Gly Lys Glu Gly Val Thr Asp Asp
            340                 345                 350 aat gca aaa aaa gcc att tta aaa aca aat aat gat aaa act aag ggc     1104
Asn Ala Lys Lys Ala Ile Leu Lys Thr Asn Asn Asp Lys Thr Lys Gly
            355                 360                 365 gct gat gaa ctt gaa aag tta ttt gaa tca gta aaa aac ttg tca aaa     1152
Ala Asp Glu Leu Glu Lys Leu Phe Glu Ser Val Lys Asn Leu Ser Lys
370                 375                 380 gca gct aaa gag atg ctt act aat tca gtt aaa gag ctt aca agc         1197
Ala Ala Lys Glu Met Leu Thr Asn Ser Val Lys Glu Leu Thr Ser
385                 390                 395
```

<210> SEQ ID NO 60
<211> LENGTH: 399
<212> TYPE: PRT
<213> ORGANISM: ospC Chimera

<400> SEQUENCE: 60

```
Met Arg Leu Leu Ile Gly Phe Ala Leu Ala Leu Ile Gly Cys
 1               5                  10                  15

Ala Gln Lys Gly Ala Glu Ser Ile Gly Ser Cys Asn Asn Ser Gly Lys
                20                  25                  30

Asp Gly Asn Thr Ser Ala Asn Ser Ala Asp Glu Ser Val Lys Gly Pro
            35                  40                  45

Asn Leu Thr Glu Ile Ser Lys Lys Ile Thr Asp Ser Asn Ala Val Leu
        50                  55                  60

Leu Ala Val Lys Glu Val Glu Ala Leu Leu Ser Ser Ile Asp Glu Ile
65                  70                  75                  80
```

-continued

```
Ala Ala Lys Ala Ile Gly Lys Lys Ile His Gln Asn Asn Gly Leu Asp
                85                  90                  95

Thr Glu Tyr Asn His Asn Gly Ser Leu Leu Ala Gly Ala Tyr Ala Ile
            100                 105                 110

Ser Thr Leu Ile Lys Gln Lys Leu Asp Gly Leu Lys Asn Glu Gly Leu
        115                 120                 125

Lys Glu Lys Ile Asp Ala Ala Lys Lys Cys Ser Glu Thr Phe Thr Asn
    130                 135                 140

Lys Leu Lys Glu Lys His Thr Asp Leu Gly Lys Glu Gly Val Thr Asp
145                 150                 155                 160

Ala Asp Ala Lys Glu Ala Ile Leu Lys Thr Asn Gly Thr Lys Thr Lys
                165                 170                 175

Gly Ala Glu Glu Leu Gly Lys Leu Phe Glu Ser Val Glu Val Leu Ser
            180                 185                 190

Lys Ala Ala Lys Glu Met Leu Ala Asn Ser Val Lys Glu Leu Thr Ser
        195                 200                 205

Pro Val Val Ala Glu Ser Pro Ala Met Val Asn Asn Ser Gly Lys Asp
    210                 215                 220

Gly Asn Thr Ser Ala Asn Ser Ala Asp Glu Ser Val Lys Gly Pro Asn
225                 230                 235                 240

Leu Thr Glu Ile Ser Lys Lys Ile Thr Glu Ser Asn Ala Val Val Leu
                245                 250                 255

Ala Val Lys Glu Val Glu Thr Leu Leu Thr Ser Ile Asp Glu Leu Ala
            260                 265                 270

Lys Ala Ile Gly Lys Lys Ile Lys Asn Asp Val Ser Leu Asp Asn Glu
        275                 280                 285

Ala Asp His Asn Gly Ser Leu Ile Ser Gly Ala Tyr Leu Ile Ser Asn
    290                 295                 300

Leu Ile Thr Lys Lys Ile Ser Ala Ile Lys Asp Ser Gly Glu Leu Lys
305                 310                 315                 320

Ala Glu Ile Glu Lys Ala Lys Lys Cys Ser Glu Glu Phe Thr Ala Lys
                325                 330                 335

Leu Lys Gly Glu His Thr Asp Leu Gly Lys Glu Gly Val Thr Asp Asp
            340                 345                 350

Asn Ala Lys Lys Ala Ile Leu Lys Thr Asn Asn Asp Lys Thr Lys Gly
        355                 360                 365

Ala Asp Glu Leu Glu Lys Leu Phe Glu Ser Val Lys Asn Leu Ser Lys
    370                 375                 380

Ala Ala Lys Glu Met Leu Thr Asn Ser Val Lys Glu Leu Thr Ser
385                 390                 395
```

<210> SEQ ID NO 61
<211> LENGTH: 1196
<212> TYPE: DNA
<213> ORGANISM: ospC Chimera
<220> FEATURE:
<221> NAME/KEY: CDS
<222> LOCATION: (1)...(1196)

<400> SEQUENCE: 61

```
atg aga tta tta ata gga ttt gct tta gcg tta gct tta ata gga tgt    48
Met Arg Leu Leu Ile Gly Phe Ala Leu Ala Le -continued

| | |
|---|---|
| gat ggg aat aca tct gca aat tct gct gat gag tct gtt aaa ggg cct<br>Asp Gly Asn Thr Ser Ala Asn Ser Ala Asp Glu Ser Val Lys Gly Pro<br>35                    40                    45 | 144 |
| aat ctt aca gaa ata agt aaa aaa att acg gat tct aat gcg gtt tta<br>Asn Leu Thr Glu Ile Ser Lys Lys Ile Thr Asp Ser Asn Ala Val Leu<br>50                    55                    60 | 192 |
| ctt gct gtg aaa gag gtt gaa gcg ttg ctg tca tct ata gat gaa att<br>Leu Ala Val Lys Glu Val Glu Ala Leu Leu Ser Ser Ile Asp Glu Ile<br>65                    70                    75                    80 | 240 |
| gct gct aaa gct att ggt aaa aaa ata cac caa aat aat ggt ttg gat<br>Ala Ala Lys Ala Ile Gly Lys Lys Ile His Gln Asn Asn Gly Leu Asp<br>                    85                    90                    95 | 288 |
| acc gaa tat aat cac aat gga tca ttg tta gcg gga gct tat gca ata<br>Thr Glu Tyr Asn His Asn Gly Ser Leu Leu Ala Gly Ala Tyr Ala Ile<br>                    100                 105                 110 | 336 |
| tca acc cta ata aaa caa aaa tta gat gga ttg aaa aat gaa gga tta<br>Ser Thr Leu Ile Lys Gln Lys Leu Asp Gly Leu Lys Asn Glu Gly Leu<br>                    115                 120                 125 | 384 |
| aag gaa aaa att gat gcg gct aag aaa tgt tct gaa aca ttt act aat<br>Lys Glu Lys Ile Asp Ala Ala Lys Lys Cys Ser Glu Thr Phe Thr Asn<br>130                    135                 140 | 432 |
| aaa tta aaa gaa aaa cac aca gat ctt ggt aaa gaa ggt gtt act gat<br>Lys Leu Lys Glu Lys His Thr Asp Leu Gly Lys Glu Gly Val Thr Asp<br>145                    150                 155                 160 | 480 |
| gct gat gca aaa gaa gcc att tta aaa aca aat ggt act aaa act aaa<br>Ala Asp Ala Lys Glu Ala Ile Leu Lys Thr Asn Gly Thr Lys Thr Lys<br>                    165                 170                 175 | 528 |
| ggt gct gaa gaa ctt gga aaa tta ttt gaa tca gta gag gtc ttg tca<br>Gly Ala Glu Glu Leu Gly Lys Leu Phe Glu Ser Val Glu Val Leu Ser<br>                    180                 185                 190 | 576 |
| aaa gca gct aaa gag atg ctt gct aat tca gtt aaa gag ctt aca agc<br>Lys Ala Ala Lys Glu Met Leu Ala Asn Ser Val Lys Glu Leu Thr Ser<br>                    195                 200                 205 | 624 |
| cct gtt gtg gca gaa agt cca gcc atg gta aat aat tca gga aaa gat<br>Pro Val Val Ala Glu Ser Pro Ala Met Val Asn Asn Ser Gly Lys Asp<br>210                    215                 220 | 672 |
| ggg aat aca tct gca aat tct gct gat gag tct gtt aaa ggg cct aat<br>Gly Asn Thr Ser Ala Asn Ser Ala Asp Glu Ser Val Lys Gly Pro Asn<br>225                    230                 235                 240 | 720 |
| ctt aca gaa ata agt aaa aaa att aca gaa tct aac gca gtt gtt ctg<br>Leu Thr Glu Ile Ser Lys Lys Ile Thr Glu Ser Asn Ala Val Val Leu<br>                    245                 250                 255 | 768 |
| gct gtg aaa gaa att gaa act ttg ctt gca tct ata gat gaa ctt gct<br>Ala Val Lys Glu Ile Glu Thr Leu Leu Ala Ser Ile Asp Glu Leu Ala<br>                    260                 265                 270 | 816 |
| act aaa gct att ggt aaa aaa ata caa caa aat ggt ggt tta gct gtc<br>Thr Lys Ala Ile Gly Lys Lys Ile Gln Gln Asn Gly Gly Leu Ala Val<br>                    275                 280                 285 | 864 |
| gaa gcg ggg cat aat gga aca ttg tta gca ggt gct tat aca ata tca<br>Glu Ala Gly His Asn Gly Thr Leu Leu Ala Gly Ala Tyr Thr Ile Ser<br>290                    295                 300 | 912 |
| aaa cta ata aca caa aaa tta gat gga ttg aaa aat tca gaa aaa tta<br>Lys Leu Ile Thr Gln Lys Leu Asp Gly Leu Lys Asn Ser Glu Lys Leu<br>305                    310                 315                 320 | 960 |
| aag gaa aaa att gaa aat gct aag aaa tgt tct gaa gat ttt act aaa<br>Lys Glu Lys Ile Glu Asn Ala Lys Lys Cys Ser Glu Asp Phe Thr Lys<br>                    325                 330                 335 | 1008 |
| aaa cta gaa gga gaa cat gcg caa ctt gga att gaa aat gtt act gat<br>Lys Leu Glu Gly Glu His Ala Gln Leu Gly Ile Glu Asn Val Thr Asp<br>                    340                 345                 350 | 1056 |

```
gag aat gca aaa aaa gct att tta ata aca gat gca gct aaa gat aag      1104
Glu Asn Ala Lys Lys Ala Ile Leu Ile Thr Asp Ala Ala Lys Asp Lys
    355                 360                 365 ggc gct gca gag ctt gaa aag cta ttt aaa gca gta gaa aac ttg gca      1152
Gly Ala Ala Glu Leu Glu Lys Leu Phe Lys Ala Val Glu Asn Leu Ala
370                 375                 380 aaa gca gct aaa gag atg ctt gct aat tca gtt aaa gag ctt ac           1196
Lys Ala Ala Lys Glu Met Leu Ala Asn Ser Val Lys Glu Leu
385                 390                 395

<210> SEQ ID NO 62
<211> LENGTH: 398
<212> TYPE: PRT
<213> ORGANISM: ospC Chimera

<400> SEQUENCE: 62

Met Arg Leu Leu Ile Gly Phe Ala Leu Ala Leu Ala Leu Ile Gly Cys
1               5                   10                  15

Ala Gln Lys Gly Ala Gl

```
                        305                 310                 315                 320
Lys Glu Lys Ile Glu Asn Ala Lys Lys Cys Ser Glu Asp Phe Thr Lys
                    325                 330                 335

Lys Leu Glu Gly Glu His Ala Gln Leu Gly Ile Glu Asn Val Thr Asp
                340                 345                 350

Glu Asn Ala Lys Lys Ala Ile Leu Ile Thr Asp Ala Lys Asp Lys
            355                 360                 365

Gly Ala Ala Glu Leu Glu Lys Leu Phe Lys Ala Val Glu Asn Leu Ala
    370                 375                 380

Lys Ala Ala Lys Glu Met Leu Ala Asn Ser Val Lys Glu Leu
385                 390                 395

<210> SEQ ID NO 63
<211> LENGTH: 1185
<212> TYPE: DNA
<213> ORGANISM: ospC Chimera
<220> FEATURE:
<221> NAME/KEY: CDS
<222> LOCATION: (1)...(1185)

<400> SEQUENCE: 63 atg aga tta tta ata gga ttt gct tta gcg tta gct tta ata gga tgt      48
Met Arg Leu Leu Ile Gly Phe Ala Leu Ala Leu Ala Leu Ile Gly Cys
1               5                   10                  15 gca caa aaa ggt gct gag tca att gga tcc tgt aat aat tca ggg aaa      96
Ala Gln Lys Gly Ala Glu Ser Ile Gly Ser Cys Asn Asn Ser Gly Lys
            20                  25                  30 gat ggg aat aca tct gca aat tct gct gat gag tct gtt aaa ggg cct     144
Asp Gly Asn Thr Ser Ala Asn Ser Ala Asp Glu Ser Val Lys Gly Pro
        35                  40                  45 aat ctt aca gaa ata agt aaa aaa att acg gat tct aat gcg gtt tta     192
Asn Leu Thr Glu Ile Ser Lys Lys Ile Thr Asp Ser Asn Ala Val Leu
    50                  55                  60 ctt gct gtg aaa gag gtt gaa gcg ttg ctg tca tct ata gat gag ctt     240
Leu Ala Val Lys Glu Val Glu Ala Leu Leu Ser Ser Ile Asp Glu Leu
65                  70                  75                  80 gct aaa gct att ggt aaa aaa ata aaa aac gat ggt agt tta gat aat     288
Ala Lys Ala Ile Gly Lys Lys Ile Lys Asn Asp Gly Ser Leu Asp Asn
                85                  90                  95 gaa gca aat cgc aac gag tca ttg tta gca gga gct tat aca ata tca     336
Glu Ala Asn Arg Asn Glu Ser Leu Leu Ala Gly Ala Tyr Thr Ile Ser
            100                 105                 110 acc tta ata aca caa aaa tta agt aaa tta aac gga tca gaa ggt tta     384
Thr Leu Ile Thr Gln Lys Leu Ser Lys Leu Asn Gly Ser Glu Gly Leu
        115                 120                 125 aag gaa aag att gcc gca gct aag aaa tgc tct gaa gag ttt agt act     432
Lys Glu Lys Ile Ala Ala Ala Lys Lys Cys Ser Glu Glu Phe Ser Thr
130                 135                 140 aaa cta aaa gat aat cat gca cag ctt ggt ata cag ggc gtt act gat     480
Lys Leu Lys Asp Asn His Ala Gln Leu Gly Ile Gln Gly Val Thr Asp
145                 150                 155                 160 gaa aat gca aaa aaa gct att tta aaa gca aat gca gcg ggt aaa gat     528
Glu Asn Ala Lys Lys Ala Ile Leu Lys Ala Asn Ala Ala Gly Lys Asp
                165                 170                 175 aag ggc gtt gaa gaa ctt gaa aag ttg tcc gga tca tta gaa agc tta     576
Lys Gly Val Glu Glu Leu Glu Lys Leu Ser Gly Ser Leu Glu Ser Leu
            180                 185                 190 tca aaa gca gct aaa gag atg ctt gct aat tca gtt aaa gag ctt aca     624
Ser Lys Ala Ala Lys Glu Met Leu Ala Asn Ser Val Lys Glu Leu Thr
        195                 200                 205
```

```
agc cct gtt gtc cat ggt aat aat tca ggg aaa gat ggg aat aca tct        672
Ser Pro Val Val His Gly Asn Asn Ser Gly Lys Asp Gly Asn Thr Ser
    210                 215                 220 gca aat tct gct gat gag tct gtt aaa ggg cct aat ctt aca gaa ata        720
Ala Asn Ser Ala Asp Glu Ser Val Lys Gly Pro Asn Leu Thr Glu Ile
225                 230                 235                 240 agt aaa aaa att aca gaa tct aac gca gtt gtt ctc gcc gtg aaa gaa        768
Ser Lys Lys Ile Thr Glu Ser Asn Ala Val Val Leu Ala Val Lys Glu
            245                 250                 255 gtt gaa act ttg ctt aca tct ata gat gag ctt gct aaa gct att ggt        816
Val Glu Thr Leu Leu Thr Ser Ile Asp Glu Leu Ala Lys Ala Ile Gly
        260                 265                 270 aaa aaa ata aaa aac gat gtt agt tta gat aat gag gca gat cac aac        864
Lys Lys Ile Lys Asn Asp Val Ser Leu Asp Asn Glu Ala Asp His Asn
    275                 280                 285 gga tca tta ata tca gga gca tat tta att tca aac tta ata aca aaa        912
Gly Ser Leu Ile Ser Gly Ala Tyr Leu Ile Ser Asn Leu Ile Thr Lys
290                 295                 300 aaa ata agt gca ata aaa gat tca gga gaa ttg aag gca gaa att gaa        960
Lys Ile Ser Ala Ile Lys Asp Ser Gly Glu Leu Lys Ala Glu Ile Glu
305                 310                 315                 320 aag gct aag aaa tgt tct gaa gaa ttt act gct aaa tta aaa ggt gaa       1008
Lys Ala Lys Lys Cys Ser Glu Glu Phe Thr Ala Lys Leu Lys Gly Glu
            325                 330                 335 cac aca gat ctt ggt aaa gaa ggc gtt act gat gat aat gca aaa aaa       1056
His Thr Asp Leu Gly Lys Glu Gly Val Thr Asp Asp Asn Ala Lys Lys
        340                 345                 350 gcc att tta aaa aca aat aat gat aaa act aag ggc gct gat gaa ctt       1104
Ala Ile Leu Lys Thr Asn Asn Asp Lys Thr Lys Gly Ala Asp Glu Leu
    355                 360                 365 gaa aag tta ttt gaa tca gta aaa aac ttg tca aaa gca gct aaa gag       1152
Glu Lys Leu Phe Glu Ser Val Lys Asn Leu Ser Lys Ala Ala Lys Glu
370                 375                 380 atg ctt act aat tca gtt aaa gag ctt aca agc                          1185
Met Leu Thr Asn Ser Val Lys Glu Leu Thr Ser
385                 390                 395

<210> SEQ ID NO 64
<211> LENGTH: 395
<212> TYPE: PRT
<213> ORGANISM: ospC Chimera

<400> SEQUENCE: 64

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Cys Asn Asn Ser Gly Lys
            20                  25                  30

Asp Gly Asn Thr Ser Ala Asn Ser Ala Asp Glu Ser Val Lys Gly Pro
        35                  40                  45

Asn Leu Thr Glu Ile Ser Lys Lys Ile Thr Asp Ser Asn Ala Val Leu
    50                  55                  60

Leu Ala Val Lys Glu Val Glu Ala Leu Leu Ser Ser Ile Asp Glu Leu
65                  70                  75                  80

Ala Lys Ala Ile Gly Lys Lys Ile Lys Asn Asp Gly Ser Leu Asp Asn
            85                  90                  95

Glu Ala Asn Arg Asn Glu Ser Leu Leu Ala Gly Ala Tyr Thr Ile Ser
        100                 105                 110

Thr Leu Ile Thr Gln Lys Leu Ser Lys Leu Asn Gly Ser Glu Gly Leu
```

```
            115                 120                 125
Lys Glu Lys Ile Ala Ala Lys Lys Cys Ser Glu Glu Phe Ser Thr
        130                 135                 140

Lys Leu Lys Asp Asn His Ala Gln Leu Gly Ile Gln Gly Val Thr Asp
145                 150                 155                 160

Glu Asn Ala Lys Lys Ala Ile Leu Lys Ala Asn Ala Ala Gly Lys Asp
                165                 170                 175

Lys Gly Val Glu Glu Leu Glu Lys Leu Ser Gly Ser Leu Glu Ser Leu
            180                 185                 190

Ser Lys Ala Ala Lys Glu Met Leu Ala Asn Ser Val Lys Glu Leu Thr
        195                 200                 205

Ser Pro Val Val His Gly Asn Asn Ser Gly Lys Asp Gly Asn Thr Ser
210                 215                 220

Ala Asn Ser Ala Asp Glu Ser Val Lys Gly Pro Asn Leu Thr Glu Ile
225                 230                 235                 240

Ser Lys Lys Ile Thr Glu Ser Asn Ala Val Val Leu Ala Val Lys Glu
                245                 250                 255

Val Glu Thr Leu Leu Thr Ser Ile Asp Glu Leu Ala Lys Ala Ile Gly
            260                 265                 270

Lys Lys Ile Lys Asn Asp Val Ser Leu Asp Asn Glu Ala Asp His Asn
        275                 280                 285

Gly Ser Leu Ile Ser Gly Ala Tyr Leu Ile Ser Asn Leu Ile Thr Lys
        290                 295                 300

Lys Ile Ser Ala Ile Lys Asp Ser Gly Glu Leu Lys Ala Glu Ile Glu
305                 310                 315                 320

Lys Ala Lys Lys Cys Ser Glu Glu Phe Thr Ala Lys Leu Lys Gly Glu
                325                 330                 335

His Thr Asp Leu Gly Lys Glu Gly Val Thr Asp Asp Asn Ala Lys Lys
            340                 345                 350

Ala Ile Leu Lys Thr Asn Asn Asp Lys Thr Lys Gly Ala Asp Glu Leu
        355                 360                 365

Glu Lys Leu Phe Glu Ser Val Lys Asn Leu Ser Lys Ala Ala Lys Glu
        370                 375                 380

Met Leu Thr Asn Ser Val Lys Glu Leu Thr Ser
385                 390                 395

<210> SEQ ID NO 65
<211> LENGTH: 1184
<212> TYPE: DNA
<213> ORGANISM: ospC Chimera
<220> FEATURE:
<221> NAME/KEY: CDS
<222> LOCATION: (1)...(1184)

<400> SEQUENCE: 65 atg aga tta tta ata gga ttt gct tta gcg tta gct tta ata gga tgt    48
Met Arg Leu Leu Ile Gly Phe Ala Leu Ala Leu Ala Leu Ile G -continued

```
ctt gct gtg aaa gag gtt gaa gcg ttg ctg tca tct ata gat gag ctt     240
Leu Ala Val Lys Glu Val Glu Ala Leu Leu Ser Ser Ile Asp Glu Leu
 65              70                  75                  80 gct aaa gct att ggt aaa aaa ata aaa aac gat ggt agt tta gat aat     288
Ala Lys Ala Ile Gly Lys Lys Ile Lys Asn Asp Gly Ser Leu Asp Asn
                 85                  90                  95 gaa gca aat cgc aac gag tca ttg tta gca gga gct tat aca ata tca     336
Glu Ala Asn Arg Asn Glu Ser Leu Leu Ala Gly Ala Tyr Thr Ile Ser
            100                 105                 110 acc tta ata aca caa aaa tta agt aaa tta aac gga tca gaa ggt tta     384
Thr Leu Ile Thr Gln Lys Leu Ser Lys Leu Asn Gly Ser Glu Gly Leu
        115                 120                 125 aag gaa aag att gcc gca gct aag aaa tgc tct gaa gag ttt agt act     432
Lys Glu Lys Ile Ala Ala Ala Lys Lys Cys Ser Glu Glu Phe Ser Thr
    130                 135                 140 aaa cta aaa gat aat cat gca cag ctt ggt ata cag ggc gtt act gat     480
Lys Leu Lys Asp Asn His Ala Gln Leu Gly Ile Gln Gly Val Thr Asp
145                 150                 155                 160 gaa aat gca aaa aaa gct att tta aaa gca aat gca gcg ggt aaa gat     528
Glu Asn Ala Lys Lys Ala Ile Leu Lys Ala Asn Ala Ala Gly Lys Asp
                165                 170                 175 aag ggc gtt gaa gaa ctt gaa aag ttg tcc gga tca tta gaa agc tta     576
Lys Gly Val Glu Glu Leu Glu Lys Leu Ser Gly Ser Leu Glu Ser Leu
            180                 185                 190 tca aaa gca gct aaa gag atg ctt gct aat tca gtt aaa gag ctt aca     624
Ser Lys Ala Ala Lys Glu Met Leu Ala Asn Ser Val Lys Glu Leu Thr
        195                 200                 205 agc cct gtt gtc cat ggt aat aat tca gga aaa gat ggg aat aca tct     672
Ser Pro Val Val His Gly Asn Asn Ser Gly Lys Asp Gly Asn Thr Ser
    210                 215                 220 gca aat tct gct gat gag tct gtt aaa ggg cct aat ctt aca gaa ata     720
Ala Asn Ser Ala Asp Glu Ser Val Lys Gly Pro Asn Leu Thr Glu Ile
225                 230                 235                 240 agt aaa aaa att aca gaa tct aac gca gtt gtt ctg gct gtg aaa gaa     768
Ser Lys Lys Ile Thr Glu Ser Asn Ala Val Val Leu Ala Val Lys Glu
                245                 250                 255 att gaa act ttg ctt gca tct ata gat gaa ctt gct act aaa gct att     816
Ile Glu Thr Leu Leu Ala Ser Ile Asp Glu Leu Ala Thr Lys Ala Ile
            260                 265                 270 ggt aaa aaa ata caa caa aat ggt ggt tta gct gtc gaa gcg ggg cat     864
Gly Lys Lys Ile Gln Gln Asn Gly Gly Leu Ala Val Glu Ala Gly His
        275                 280                 285 aat gga aca ttg tta gca ggt gct tat aca ata tca aaa cta ata aca     912
Asn Gly Thr Leu Leu Ala Gly Ala Tyr Thr Ile Ser Lys Leu Ile Thr
    290                 295                 300 caa aaa tta gat gga ttg aaa aat tca gaa aaa tta aag gaa aaa att     960
Gln Lys Leu Asp Gly Leu Lys Asn Ser Glu Lys Leu Lys Glu Lys Ile
305                 310                 315                 320 gaa aat gct aag aaa tgt tct gaa gat ttt act aaa aaa cta gaa gga    1008
Glu Asn Ala Lys Lys Cys Ser Glu Asp Phe Thr Lys Lys Leu Glu Gly
                325                 330                 335 gaa cat gcg caa ctt gga att gaa aat gtt act gat gag aat gca aaa    1056
Glu His Ala Gln Leu Gly Ile Glu Asn Val Thr Asp Glu Asn Ala Lys
            340                 345                 350 aaa gct att tta ata aca gat gca gct aaa gat aag ggc gct gca gag    1104
Lys Ala Ile Leu Ile Thr Asp Ala Ala Lys Asp Lys Gly Ala Ala Glu
        355                 360                 365 ctt gaa aag cta ttt aaa gca gta gaa aac ttg gca aaa gca gct aaa    1152
Leu Glu Lys Leu Phe Lys Ala Val Glu Asn Leu Ala Lys Ala Ala Lys
```

```
              370             375             380
gag atg ctt gct aat tca gtt aaa gag ctt ac                                    1184
Glu Met Leu Ala Asn Ser Val Lys Glu Leu
385                 390
```

<210> SEQ ID NO 66
<211> LENGTH: 394
<212> TYPE: PRT
<213> ORGANISM: ospC Chimera

<400> SEQUENCE: 66

```
Met Arg Leu Leu Ile Gly Phe Ala Leu Ala Leu Ala Leu Ile Gly Cys
 1               5                  10                  15

Ala Gln Lys Gly Ala Glu Ser Ile Gly Ser Cys Asn Asn Ser Gly Lys
            20                  25                  30

Asp Gly Asn Thr Ser Ala Asn Ser Ala Asp Glu Ser Val Lys Gly Pro
        35                  40                  45

Asn Leu Thr Glu Ile Ser Lys Lys Ile Thr Asp Ser Asn Ala Val Leu
    50                  55                  60

Leu Ala Val Lys Glu Val Glu Ala Leu Ser Ser Ile Asp Glu Leu
65                  70                  75                  80

Ala Lys Ala Ile Gly Lys Lys Ile Lys Asn Asp Gly Ser Leu Asp Asn
                85                  90                  95

Glu Ala Asn Arg Asn Glu Ser Leu Leu Ala Gly Ala Tyr Thr Ile Ser
            100                 105                 110

Thr Leu Ile Thr Gln Lys Leu Ser Lys Leu Asn Gly Ser Glu Gly Leu
        115                 120                 125

Lys Glu Lys Ile Ala Ala Lys Lys Cys Ser Glu Glu Phe Ser Thr
130                 135                 140

Lys Leu Lys Asp Asn His Ala Gln Leu Gly Ile Gln Gly Val Thr Asp
145                 150                 155                 160

Glu Asn Ala Lys Lys Ala Ile Leu Lys Ala Asn Ala Ala Gly Lys Asp
                165                 170                 175

Lys Gly Val Glu Glu Leu Glu Lys Leu Ser Gly Ser Leu Glu Ser Leu
            180                 185                 190

Ser Lys Ala Ala Lys Glu Met Leu Ala Asn Ser Val Lys Glu Leu Thr
        195                 200                 205

Ser Pro Val Val His Gly Asn Asn Ser Gly Lys Asp Gly Asn Thr Ser
    210                 215                 220

Ala Asn Ser Ala Asp Glu Ser Val Lys Gly Pro Asn Leu Thr Glu Ile
225                 230                 235                 240

Ser Lys Lys Ile Thr Glu Ser Asn Ala Val Val Leu Ala Val Lys Glu
                245                 250                 255

Ile Glu Thr Leu Leu Ala Ser Ile Asp Glu Leu Ala Thr Lys Ala Ile
            260                 265                 270

Gly Lys Lys Ile Gln Gln Asn Gly Gly Leu Ala Val Glu Ala Gly His
        275                 280                 285

Asn Gly Thr Leu Leu Ala Gly Ala Tyr Thr Ile Ser Lys Leu Ile Thr
    290                 295                 300

Gln Lys Leu Asp Gly Leu Lys Asn Ser Glu Lys Leu Lys Glu Lys Ile
305                 310                 315                 320

Glu Asn Ala Lys Lys Cys Ser Glu Asp Phe Thr Lys Leu Glu Gly
                325                 330                 335

Glu His Ala Gln Leu Gly Ile Glu Asn Val Thr Asp Glu Asn Ala Lys
            340                 345                 350
```

```
Lys Ala Ile Leu Ile Thr Asp Ala Ala Lys Asp Lys Gly Ala Ala Glu
            355                 360                 365

Leu Glu Lys Leu Phe Lys Ala Val Glu Asn Leu Ala Lys Ala Ala Lys
        370                 375                 380

Glu Met Leu Ala Asn Ser Val Lys Glu Leu
385                 390

<210> SEQ ID NO 67
<211> LENGTH: 1184
<212> TYPE: DNA
<213> ORGANISM: ospC Chimera
<220> FEATURE:
<221> NAME/KEY: CDS
<222> LOCATION: (1)...(1184)

<400> SEQUENCE: 67
```

| | | | | | | | | | | | | | | | | |
|---|---|---|---|---|---|---|---|---|---|---|---|---|---|---|---|---|
| atg | aga | tta | tta | ata | gga | ttt | gct | tta | gcg | tta | gct | tta | ata | gga | tgt | 48 |
| Met | Arg | Leu | Leu | Ile | Gly | Phe | Ala | Leu | Ala | Leu | Ala | Leu | Ile | Gly | Cys | |
| 1 | | | | 5 | | | | | 10 | | | | | 15 | | |
| gca | caa | aaa | ggt | gct | gag | tca | att | gga | tcc | tgt | aat | aat | tca | ggg | aaa | 96 |
| Ala | Gln | Lys | Gly | Ala | Glu | Ser | Ile | Gly | Ser | Cys | Asn | Asn | Ser | Gly | Lys | |
| | | | 20 | | | | | 25 | | | | | 30 | | | |
| gat | ggg | aat | aca | tct | gca | aat | tct | gct | gat | gag | tct | gtt | aaa | ggg | cct | 144 |
| Asp | Gly | Asn | Thr | Ser | Ala | Asn | Ser | Ala | Asp | Glu | Ser | Val | Lys | Gly | Pro | |
| | | 35 | | | | | 40 | | | | | 45 | | | | |
| aat | ctt | aca | gaa | ata | agt | aaa | aaa | att | acg | gat | tct | aat | gcg | gtt | tta | 192 |
| Asn | Leu | Thr | Glu | Ile | Ser | Lys | Lys | Ile | Thr | Asp | Ser | Asn | Ala | Val | Leu | |
| | 50 | | | | | 55 | | | | | 60 | | | | | |
| ctt | gct | gtg | aaa | gag | gtt | gaa | gcg | ttg | ctg | tca | tct | ata | gat | gag | ctt | 240 |
| Leu | Ala | Val | Lys | Glu | Val | Glu | Ala | Leu | Leu | Ser | Ser | Ile | Asp | Glu | Leu | |
| 65 | | | | | 70 | | | | | 75 | | | | | 80 | |
| gct | aaa | gct | att | ggt | aaa | aaa | ata | aaa | aac | gat | ggt | agt | tta | gat | aat | 288 |
| Ala | Lys | Ala | Ile | Gly | Lys | Lys | Ile | Lys | Asn | Asp | Gly | Ser | Leu | Asp | Asn | |
| | | | | 85 | | | | | 90 | | | | | 95 | | |
| gaa | gca | aat | cgc | aac | gag | tca | ttg | tta | gca | gga | gct | tat | aca | ata | tca | 336 |
| Glu | Ala | Asn | Arg | Asn | Glu | Ser | Leu | Leu | Ala | Gly | Ala | Tyr | Thr | Ile | Ser | |
| | | | 100 | | | | | 105 | | | | | 110 | | | |
| acc | tta | ata | aca | caa | aaa | tta | agt | aaa | tta | aac | gga | tca | gaa | ggt | tta | 384 |
| Thr | Leu | Ile | Thr | Gln | Lys | Leu | Ser | Lys | Leu | Asn | Gly | Ser | Glu | Gly | Leu | |
| | | 115 | | | | | 120 | | | | | 125 | | | | |
| aag | gaa | aag | att | gcc | gca | gct | aag | aaa | tgc | tct | gaa | gag | ttt | agt | act | 432 |
| Lys | Glu | Lys | Ile | Ala | Ala | Ala | Lys | Lys | Cys | Ser | Glu | Glu | Phe | Ser | Thr | |
| | 130 | | | | | 135 | | | | | 140 | | | | | |
| aaa | cta | aaa | gat | aat | cat | gca | cag | ctt | ggt | ata | cag | ggc | gtt | act | gat | 480 |
| Lys | Leu | Lys | Asp | Asn | His | Ala | Gln | Leu | Gly | Ile | Gln | Gly | Val | Thr | Asp | |
| 145 | | | | | 150 | | | | | 155 | | | | | 160 | |
| gaa | aat | gca | aaa | aaa | gct | att | tta | aaa | gca | aat | gca | gcg | ggt | aaa | gat | 528 |
| Glu | Asn | Ala | Lys | Lys | Ala | Ile | Leu | Lys | Ala | Asn | Ala | Ala | Gly | Lys | Asp | |
| | | | | 165 | | | | | 170 | | | | | 175 | | |
| aag | ggc | gtt | gaa | gaa | ctt | gaa | aag | ttg | tcc | gga | tca | tta | gaa | agc | tta | 576 |
| Lys | Gly | Val | Glu | Glu | Leu | Glu | Lys | Leu | Ser | Gly | Ser | Leu | Glu | Ser | Leu | |
| | | | 180 | | | | | 185 | | | | | 190 | | | |
| tca | aaa | gca | gct | aaa | gag | atg | ctt | gct | aat | tca | gtt | aaa | gag | ctt | aca | 624 |
| Ser | Lys | Ala | Ala | Lys | Glu | Met | Leu | Ala | Asn | Ser | Val | Lys | Glu | Leu | Thr | |
| | | 195 | | | | | 200 | | | | | 205 | | | | |
| agc | cct | gtt | gtc | cat | ggt | aat | aat | tca | aga | aaa | gat | ggg | aat | gca | tct | 672 |
| Ser | Pro | Val | Val | His | Gly | Asn | Asn | Ser | Arg | Lys | Asp | Gly | Asn | Ala | Ser | |
| | 210 | | | | | 215 | | | | | 220 | | | | | |
| aca | aat | tct | gcc | gat | gag | tct | gtt | aaa | ggg | cct | aat | ctt | aca | gaa | ata | 720 |
| Thr | Asn | Ser | Ala | Asp | Glu | Ser | Val | Lys | Gly | Pro | Asn | Leu | Thr | Glu | Ile | |

-continued

| | | |
|---|---|---|
| agt aaa aaa att aca gaa tct aac gca gtt gtt ctg gcc gtg aaa gaa<br>Ser Lys Lys Ile Thr Glu Ser Asn Ala Val Val Leu Ala Val Lys Glu<br>                        245                            250                           255 | 768 |
| gtt gag acc tta ctt gca tct ata gat gaa ctt gct acc aaa gct att<br>Val Glu Thr Leu Leu Ala Ser Ile Asp Glu Leu Ala Thr Lys Ala Ile<br>                   260                            265                           270 | 816 |
| ggt aag aaa ata ggc aat aat ggt tta gag gcc aat cag agt aaa aac<br>Gly Lys Lys Ile Gly Asn Asn Gly Leu Glu Ala Asn Gln Ser Lys Asn<br>        275                            280                           285 | 864 |
| aca tca ttg tta tca gga gct tat gca ata tct gac cta ata gca gaa<br>Thr Ser Leu Leu Ser Gly Ala Tyr Ala Ile Ser Asp Leu Ile Ala Glu<br>        290                            295                           300 | 912 |
| aaa tta aat gta ttg aaa aat gaa gaa tta aag gaa aag att gat aca<br>Lys Leu Asn Val Leu Lys Asn Glu Glu Leu Lys Glu Lys Ile Asp Thr<br>305                            310                           315                        320 | 960 |
| gct aag caa tgt tct aca gaa ttt act aat aaa cta aaa agt gaa cat<br>Ala Lys Gln Cys Ser Thr Glu Phe Thr Asn Lys Leu Lys Ser Glu His<br>                   325                           330                           335 | 1008 |
| gca gtg ctt ggt ctg gac aat ctt act gat gat aat gca caa aga gct<br>Ala Val Leu Gly Leu Asp Asn Leu Thr Asp Asp Asn Ala Gln Arg Ala<br>              340                            345                           350 | 1056 |
| att tta aaa aaa cat gca aat aaa gat aag ggt gct gca gaa ctt gaa<br>Ile Leu Lys Lys His Ala Asn Lys Asp Lys Gly Ala Ala Glu Leu Glu<br>                   355                           360                           365 | 1104 |
| aag tta ttt aaa gcg gta gaa aac tta tca aaa gca gct caa gac aca<br>Lys Leu Phe Lys Ala Val Glu Asn Leu Ser Lys Ala Ala Gln Asp Thr<br>370                            375                           380 | 1152 |
| tta aaa aat gct gtt aaa gag ctt aca agt cc<br>Leu Lys Asn Ala Val Lys Glu Leu Thr Ser<br>385                            390 | 1184 |

<210> SEQ ID NO 68
<211> LENGTH: 394
<212> TYPE: PRT
<213> ORGANISM: ospC Chimera

<400> SEQUENCE: 68

```
Met Arg Leu Leu Ile Gly Phe Ala Leu Ala Leu Ala Leu Ile Gly Cys
 1               5                   10                  15

Ala Gln Lys Gly Ala Glu Ser Ile Gly Ser Cys Asn Asn Ser Gly Lys
             20                  25                  30

Asp Gly Asn Thr Ser Ala Asn Ser Ala Asp Glu Ser Val Lys Gly Pro
         35                  40                  45

Asn Leu Thr Glu Ile Ser Lys Lys Ile Thr Asp Ser Asn Ala Val Leu
     50                  55                  60

Leu Ala Val Lys Glu Val Glu Ala Leu Leu Ser Ser Ile Asp Glu Leu
 65                  70                  75                  80

Ala Lys Ala Ile Gly Lys Lys Ile Lys Asn Asp Gly Ser Leu Asp Asn
                 85                  90                  95

Glu Ala Asn Arg Asn Glu Ser Leu Leu Ala Gly Ala Tyr Thr Ile Ser
            100                 105                 110

Thr Leu Ile Thr Gln Lys Leu Ser Lys Leu Asn Gly Ser Glu Gly Leu
        115                 120                 125

Lys Glu Lys Ile Ala Ala Ala Lys Cys Ser Glu Glu Phe Ser Thr
    130                 135                 140

Lys Leu Lys Asp Asn His Ala Gln Leu Gly Ile Gln Gly Val Thr Asp
145                 150                 155                 160
```

```
Glu Asn Ala Lys Lys Ala Ile Leu Lys Ala Asn Ala Ala Gly Lys Asp
            165                 170                 175

Lys Gly Val Glu Glu Leu Glu Lys Leu Ser Gly Ser Leu Glu Ser Leu
        180                 185                 190

Ser Lys Ala Ala Lys Glu Met Leu Ala Asn Ser Val Lys Glu Leu Thr
    195                 200                 205

Ser Pro Val Val His Gly Asn Asn Ser Arg Lys Asp Gly Asn Ala Ser
210                 215                 220

Thr Asn Ser Ala Asp Glu Ser Val Lys Gly Pro Asn Leu Thr Glu Ile
225                 230                 235                 240

Ser Lys Lys Ile Thr Glu Ser Asn Ala Val Leu Ala Val Lys Glu
                245                 250                 255

Val Glu Thr Leu Leu Ala Ser Ile Asp Glu Leu Ala Thr Lys Ala Ile
                260                 265                 270

Gly Lys Lys Ile Gly Asn Asn Gly Leu Glu Ala Asn Gln Ser Lys Asn
            275                 280                 285

Thr Ser Leu Leu Ser Gly Ala Tyr Ala Ile Ser Asp Leu Ile Ala Glu
290                 295                 300

Lys Leu Asn Val Leu Lys Asn Glu Glu Leu Lys Glu Lys Ile Asp Thr
305                 310                 315                 320

Ala Lys Gln Cys Ser Thr Glu Phe Thr Asn Lys Leu Lys Ser Glu His
                325                 330                 335

Ala Val Leu Gly Leu Asp Asn Leu Thr Asp Asp Asn Ala Gln Arg Ala
            340                 345                 350

Ile Leu Lys Lys His Ala Asn Lys Asp Lys Gly Ala Ala Glu Leu Glu
        355                 360                 365

Lys Leu Phe Lys Ala Val Glu Asn Leu Ser Lys Ala Ala Gln Asp Thr
    370                 375                 380

Leu Lys Asn Ala Val Lys Glu Leu Thr Ser
385                 390
```

<210> SEQ ID NO 69
<211> LENGTH: 1209
<212> TYPE: DNA
<213> ORGANISM: ospC Chimera
<220> FEATURE:
<221> NAME/KEY: CDS
<222> LOCATION: (1)...(1209)

<400> SEQUENCE: 69

```
atg aga tta tta ata gga ttt gct tta gcg tta gct tta ata gga tgt      48
Met Arg Leu Leu Ile Gly Phe Ala Leu Ala Leu Ala Leu Ile Gly Cys
  1               5                  10                  15 gca caa aaa ggt gct gag tca att gga tcc tgt aat aat tca ggg aaa      96
Ala Gln Lys Gly Ala Glu Ser Ile Gly Ser Cys Asn Asn Ser Gly Lys
             20                  25                  30 gat ggg aat aca tct gca aat tct gct gat gag tct gtt aaa ggg cct     144
Asp Gly Asn Thr Ser Ala Asn Ser Ala Asp Glu Ser Val Lys Gly Pro
         35                  40                  45 aat ctt aca gaa ata agt aaa aaa att acg gat tct aat gcg gtt tta     192
Asn Leu Thr Glu Ile Ser Lys Lys Ile Thr Asp Ser Asn Ala Val Leu
     50                  55                  60 ctt gct gtg aaa gag gtt gaa gcg ttg ctg tca tct ata gat gag ctt     240
Leu Ala Val Lys Glu Val Glu Ala Leu Leu Ser Ser Ile Asp Glu Leu
 65                  70                  75                  80 gct aaa gct att ggt aaa aaa ata aaa aac gat ggt agt tta gat aat     288
Ala Lys Ala Ile Gly Lys Lys Ile Lys Asn Asp Gly Ser Leu Asp Asn
```

```
                              85                    90                    95
gaa gca aat cgc aac gag tca ttg tta gca gga gct tat aca ata tca       336
Glu Ala Asn Arg Asn Glu Ser Leu Leu Ala Gly Ala Tyr Thr Ile Ser
            100                 105                 110 acc tta ata aca caa aaa tta agt aaa tta aac gga tca gaa ggt tta       384
Thr Leu Ile Thr Gln Lys Leu Ser Lys Leu Asn Gly Ser Glu Gly Leu
            115                 120                 125 aag gaa aag att gcc gca gct aag aaa tgc tct gaa gag ttt agt act       432
Lys Glu Lys Ile Ala Ala Ala Lys Lys Cys Ser Glu Glu Phe Ser Thr
            130                 135                 140 aaa cta aaa gat aat cat gca cag ctt ggt ata cag ggc gtt act gat       480
Lys Leu Lys Asp Asn His Ala Gln Leu Gly Ile Gln Gly Val Thr Asp
145                 150                 155                 160 gaa aat gca aaa aaa gct att tta aaa gca aat gca gcg ggt aaa gat       528
Glu Asn Ala Lys Lys Ala Ile Leu Lys Ala Asn Ala Ala Gly Lys Asp
            165                 170                 175 aag ggc gtt gaa gaa ctt gaa aag ttg tcc gga tca tta gaa agc tta       576
Lys Gly Val Glu Glu Leu Glu Lys Leu Ser Gly Ser Leu Glu Ser Leu
            180                 185                 190 tca aaa gca gct aaa gag atg ctt gct aat tca gtt aaa gag ctt aca       624
Ser Lys Ala Ala Lys Glu Met Leu Ala Asn Ser Val Lys Glu Leu Thr
            195                 200                 205 agc cct gtt gtc cat ggt aat aat tca ggt ggg gat tct gca tct act       672
Ser Pro Val Val His Gly Asn Asn Ser Gly Gly Asp Ser Ala Ser Thr
210                 215                 220 aat cct gat gag tct gca aaa gga cct aat ctt acc gta ata agc aaa       720
Asn Pro Asp Glu Ser Ala Lys Gly Pro Asn Leu Thr Val Ile Ser Lys
225                 230                 235                 240 aaa att aca gat tct aat gca ttt tta ctg gct gtg aaa gaa gtt gag       768
Lys Ile Thr Asp Ser Asn Ala Phe Leu Leu Ala Val Lys Glu Val Glu
            245                 250                 255 gct ttg ctt tca tct ata gat gaa ctt tct aaa gct att ggt aaa aaa       816
Ala Leu Leu Ser Ser Ile Asp Glu Leu Ser Lys Ala Ile Gly Lys Lys
            260                 265                 270 ata aaa aat gat ggt act tta gat aac gaa gca aat cga aac gaa tca       864
Ile Lys Asn Asp Gly Thr Leu Asp Asn Glu Ala Asn Arg Asn Glu Ser
            275                 280                 285 ttg ata gca gga gct tat gaa ata tca aaa cta ata aca caa aaa tta       912
Leu Ile Ala Gly Ala Tyr Glu Ile Ser Lys Leu Ile Thr Gln Lys Leu
            290                 295                 300 agt gta ttg aat tca gaa gaa tta aag aaa aaa att aaa gag gct aag       960
Ser Val Leu Asn Ser Glu Glu Leu Lys Lys Lys Ile Lys Glu Ala Lys
305                 310                 315                 320 gat tgt tcc caa aaa ttt act act aag cta aaa gat agt cat gca gag      1008
Asp Cys Ser Gln Lys Phe Thr Thr Lys Leu Lys Asp Ser His Ala Glu
            325                 330                 335 ctt ggt ata caa agc gtt cag gat gat aat gca aaa aaa gct att tta      1056
Leu Gly Ile Gln Ser Val Gln Asp Asp Asn Ala Lys Lys Ala Ile Leu
            340                 345                 350 aaa aca cat gga act aaa gac aag ggt gct aaa gaa ctt gaa gag tta      1104
Lys Thr His Gly Thr Lys Asp Lys Gly Ala Lys Glu Leu Glu Glu Leu
            355                 360                 365 ttt aaa tca cta gaa agc ttg tca aaa gca gcg caa gca gca tta act      1152
Phe Lys Ser Leu Glu Ser Leu Ser Lys Ala Ala Gln Ala Ala Leu Thr
370                 375                 380 aat tca gtt aaa gag ctt aca aat cct gtt gtg gca gaa agt cca aaa      1200
Asn Ser Val Lys Glu Leu Thr Asn Pro Val Val Ala Glu Ser Pro Lys
385                 390                 395                 400 aaa cct taa                                                          1209
```

Lys Pro *

<210> SEQ ID NO 70
<211> LENGTH: 402
<212> TYPE: PRT
<213> ORGANISM: ospC Chimera

<400> SEQUENCE: 70

```
Met Arg Leu Leu Ile Gly Phe Ala Leu Ala Leu Ile Gly Cys
 1               5                  10                  15

Ala Gln Lys Gly Ala Glu Ser Ile Gly Ser Cys Asn Asn Ser Gly Lys
            20                  25                  30

Asp Gly Asn Thr Ser Ala Asn Ser Ala Asp Glu Ser Val Lys Gly Pro
        35                  40                  45

Asn Leu Thr Glu Ile Ser Lys Lys Ile Thr Asp Ser Asn Ala Val Leu
    50                  55                  60

Leu Ala Val Lys Glu Val Glu Ala Leu Leu Ser Ser Ile Asp Glu Leu
65                  70                  75                  80

Ala Lys Ala Ile Gly Lys Lys Ile Lys Asn Asp Gly Ser Leu Asp Asn
                85                  90                  95

Glu Ala Asn Arg Asn Glu Ser Leu Leu Ala Gly Ala Tyr Thr Ile Ser
            100                 105                 110

Thr Leu Ile Thr Gln Lys Leu Ser Lys Leu Asn Gly Ser Glu Gly Leu
        115                 120                 125

Lys Glu Lys Ile Ala Ala Lys Lys Cys Ser Glu Glu Phe Ser Thr
    130                 135                 140

Lys Leu Lys Asp Asn His Ala Gln Leu Gly Ile Gln Gly Val Thr Asp
145                 150                 155                 160

Glu Asn Ala Lys Lys Ala Ile Leu Lys Ala Asn Ala Ala Gly Lys Asp
                165                 170                 175

Lys Gly Val Glu Glu Leu Glu Lys Leu Ser Gly Ser Leu Glu Ser Leu
            180                 185                 190

Ser Lys Ala Ala Lys Glu Met Leu Ala Asn Ser Val Lys Glu Leu Thr
        195                 200                 205

Ser Pro Val Val His Gly Asn Asn Ser Gly Gly Asp Ser Ala Ser Thr
    210                 215                 220

Asn Pro Asp Glu Ser Ala Lys Gly Pro Asn Leu Thr Val Ile Ser Lys
225                 230                 235                 240

Lys Ile Thr Asp Ser Asn Ala Phe Leu Leu Ala Val Lys Glu Val Glu
                245                 250                 255

Ala Leu Leu Ser Ser Ile Asp Glu Leu Ser Lys Ala Ile Gly Lys Lys
            260                 265                 270

Ile Lys Asn Asp Gly Thr Leu Asp Asn Glu Ala Asn Arg Asn Glu Ser
        275                 280                 285

Leu Ile Ala Gly Ala Tyr Glu Ile Ser Lys Leu Ile Thr Gln Lys Leu
    290                 295                 300

Ser Val Leu Asn Ser Glu Glu Leu Lys Lys Ile Lys Glu Ala Lys
305                 310                 315                 320

Asp Cys Ser Gln Lys Phe Thr Thr Lys Leu Lys Asp Ser His Ala Glu
                325                 330                 335

Leu Gly Ile Gln Ser Val Gln Asp Asp Asn Ala Lys Lys Ala Ile Leu
            340                 345                 350

Lys Thr His Gly Thr Lys Asp Lys Gly Ala Lys Glu Leu Glu Glu Leu
        355                 360                 365
```

-continued

```
Phe Lys Ser Leu Glu Ser Leu Ser Lys Ala Ala Gln Ala Ala Leu Thr
    370                 375                 380

Asn Ser Val Lys Glu Leu Thr Asn Pro Val Val Ala Glu Ser Pro Lys
385                 390                 395                 400

Lys Pro
```

<210> SEQ ID NO 71
<211> LENGTH: 1179
<212> TYPE: DNA
<213> ORGANISM: ospC Chimera
<220> FEATURE:
<221> NAME/KEY: CDS
<222> LOCATION: (1)...(1179)

<400> SEQUENCE: 71

```
atg aga tta tta ata gga ttt gct tta gcg tta gct tta ata gga tgt        48
Met Arg Leu Leu Ile Gly Phe Ala Leu Ala Leu Ala Leu Ile Gly Cys
1               5                   10                  15 gca caa aaa ggt gct gag tca att gga tcc tgt aat aat tca gga aaa        96
Ala Gln Lys Gly Ala Glu Ser Ile Gly Ser Cys Asn Asn Ser Gly Lys
                20                  25                  30 gat ggg aat gca tct gca aat tct gct gat gag tct gtt aaa ggg cct      144
Asp Gly Asn Ala Ser Ala Asn Ser Ala Asp Glu Ser Val Lys Gly Pro
            35                  40                  45 aat ctt aca gaa ata agt aaa aaa att aca gaa tct aac gca gtt gtt      192
Asn Leu Thr Glu Ile Ser Lys Lys Ile Thr Glu Ser Asn Ala Val Val
        50                  55                  60 ctg gcc gtg aaa gaa gtt gag acc tta ctt gca tct ata gat gaa ctt      240
Leu Ala Val Lys Glu Val Glu Thr Leu Leu Ala Ser Ile Asp Glu Leu
65                  70                  75                  80 gct acc aaa gct att ggt aaa aaa ata ggc aat aat ggt tta gag gcc      288
Ala Thr Lys Ala Ile Gly Lys Lys Ile Gly Asn Asn Gly Leu Glu Ala
                85                  90                  95 aat cag agt aaa aac aca tca ttg tta tca gga gct tat gca ata tct      336
Asn Gln Ser Lys Asn Thr Ser Leu Leu Ser Gly Ala Tyr Ala Ile Ser
            100                 105                 110 gac cta ata gca gaa aaa tta aat gta ttg aaa aat gaa gaa tta aag      384
Asp Leu Ile Ala Glu Lys Leu Asn Val Leu Lys Asn Glu Glu Leu Lys
        115                 120                 125 gaa aag att gat aca gct aag caa tgt tct aca gaa ttt act aat aaa      432
Glu Lys Ile Asp Thr Ala Lys Gln Cys Ser Thr Glu Phe Thr Asn Lys
    130                 135                 140 cta aaa agt gaa cat gca gtg ctt ggt ctg gac aat ctt act gat gat      480
Leu Lys Ser Glu His Ala Val Leu Gly Leu Asp Asn Leu Thr Asp Asp
145                 150                 155                 160 aat gca caa aga gct att tta aaa aaa cat gca aat aaa gat aag ggt      528
Asn Ala Gln Arg Ala Ile Leu Lys Lys His Ala Asn Lys Asp Lys Gly
                165                 170                 175 gct gca gaa ctt gaa aag tta ttt aaa gcg gta gaa aac tta tca aaa      576
Ala Ala Glu Leu Glu Lys Leu Phe Lys Ala Val Glu Asn Leu Ser Lys
            180                 185                 190 gca gct caa gac aca tta aaa aat gct gtt aaa gag ctt aca agt cct      624
Ala Ala Gln Asp Thr Leu Lys Asn Ala Val Lys Glu Leu Thr Ser Pro -continued

```
aaa att aca gaa tct aac gca gtt gtt ctc gcc gtg aaa gaa gtt gaa      768
Lys Ile Thr Glu Ser Asn Ala Val Val Leu Ala Val Lys Glu Val Glu
                245                 250                 255 act ttg ctt aca tct ata gat gag ctt gct aaa gct att ggt aaa aaa      816
Thr Leu Leu Thr Ser Ile Asp Glu Leu Ala Lys Ala Ile Gly Lys Lys
            260                 265                 270 ata aaa aac gat gtt agt tta gat aat gag gca gat cac aac gga tca      864
Ile Lys Asn Asp Val Ser Leu Asp Asn Glu Ala Asp His Asn Gly Ser
        275                 280                 285 tta ata tca gga gca tat tta att tca aac tta ata aca aaa aaa ata      912
Leu Ile Ser Gly Ala Tyr Leu Ile Ser Asn Leu Ile Thr Lys Lys Ile
    290                 295                 300 agt gca ata aaa gat tca gga gaa ttg aag gca gaa att gaa aag gct      960
Ser Ala Ile Lys Asp Ser Gly Glu Leu Lys Ala Glu Ile Glu Lys Ala
305                 310                 315                 320 aag aaa tgt tct gaa gaa ttt act gct aaa tta aaa ggt gaa cac aca     1008
Lys Lys Cys Ser Glu Glu Phe Thr Ala Lys Leu Lys Gly Glu His Thr
                325                 330                 335 gat ctt ggt aaa gaa ggc gtt act gat gat aat gca aaa aaa gcc att     1056
Asp Leu Gly Lys Glu Gly Val Thr Asp Asp Asn Ala Lys Lys Ala Ile
            340                 345                 350 tta aaa aca aat aat gat aaa act aag ggc gct gat gaa ctt gaa aag     1104
Leu Lys Thr Asn Asn Asp Lys Thr Lys Gly Ala Asp Glu Leu Glu Lys
        355                 360                 365 tta ttt gaa tca gta aaa aac ttg tca aaa gca gct aaa gag atg ctt     1152
Leu Phe Glu Ser Val Lys Asn Leu Ser Lys Ala Ala Lys Glu Met Leu
    370                 375                 380 act aat tca gtt aaa gag ctt aca agc                                 1179
Thr Asn Ser Val Lys Glu Leu Thr Ser
385                 390
```

<210> SEQ ID NO 72
<211> LENGTH: 393
<212> TYPE: PRT
<213> ORGANISM: ospC Chimera

<400> SEQUENCE: 72

```
Met Arg Leu Leu Ile Gly Phe Ala Leu Ala Leu Ala Leu Ile Gly Cys
  1               5                  10                  15

Ala Gln Lys Gly Ala Glu Ser Ile Gly Ser Cys Asn Asn Ser Gly Lys
             20                  25                  30

Asp Gly Asn Ala Ser Ala Asn Ser Ala Asp Glu Ser Val Lys Gly Pro
         35                  40                  45

```
                        165                 170                 175
Ala Ala Glu Leu Glu Lys Leu Phe Lys Ala Val Glu Asn Leu Ser Lys
                180                 185                 190

Ala Ala Gln Asp Thr Leu Lys Asn Ala Val Lys Glu Leu Thr Ser Pro
            195                 200                 205

Ile Val His Gly Asn Asn Ser Gly Lys Asp Gly Asn Thr Ser Ala Asn
        210                 215                 220

Ser Ala Asp Glu Ser Val Lys Gly Pro Asn Leu Thr Glu Ile Ser Lys
225                 230                 235                 240

Lys Ile Thr Glu Ser Asn Ala Val Val Leu Ala Val Lys Glu Val Glu
                245                 250                 255

Thr Leu Leu Thr Ser Ile Asp Glu Leu Ala Lys Ala Ile Gly Lys Lys
            260                 265                 270

Ile Lys Asn Asp Val Ser Leu Asp Asn Glu Ala Asp His Asn Gly Ser
        275                 280                 285

Leu Ile Ser Gly Ala Tyr Leu Ile Ser Asn Leu Ile Thr Lys Lys Ile
    290                 295                 300

Ser Ala Ile Lys Asp Ser Gly Glu Leu Lys Ala Glu Ile Glu Lys Ala
305                 310                 315                 320

Lys Lys Cys Ser Glu Glu Phe Thr Ala Lys Leu Lys Gly Glu His Thr
                325                 330                 335

Asp Leu Gly Lys Glu Gly Val Thr Asp Asp Asn Ala Lys Lys Ala Ile
            340                 345                 350

Leu Lys Thr Asn Asn Asp Lys Thr Lys Gly Ala Asp Glu Leu Glu Lys
        355                 360                 365

Leu Phe Glu Ser Val Lys Asn Leu Ser Lys Ala Lys Glu Met Leu
    370                 375                 380

Thr Asn Ser Val Lys Glu Leu Thr Ser
385                 390

<210> SEQ ID NO 73
<211> LENGTH: 1178
<212> TYPE: DNA
<213> ORGANISM: ospC Chimera
<220> FEATURE:
<221> NAME/KEY: CDS
<222> LOCATION: (1)...(1178)

<400> SEQUENCE: 73 atg aga tta tta ata gga ttt gct tta gcg tta gct tta ata gga tgt        48
Met Arg Leu Leu Ile Gly Phe Ala Leu Ala Leu Ala Leu Ile Gly Cys

```
aat cag agt aaa aac aca tca ttg tta tca gga gct tat gca ata tct    336
Asn Gln Ser Lys Asn Thr Ser Leu Leu Ser Gly Ala Tyr Ala Ile Ser
        100                 105                 110 gac cta ata gca gaa aaa tta aat gta ttg aaa aat gaa gaa tta aag    384
Asp Leu Ile Ala Glu Lys Leu Asn Val Leu Lys Asn Glu Glu Leu Lys
            115                 120                 125 gaa aag att gat aca gct aag caa tgt tct aca gaa ttt act aat aaa    432
Glu Lys Ile Asp Thr Ala Lys Gln Cys Ser Thr Glu Phe Thr Asn Lys
130                 135                 140 cta aaa agt gaa cat gca gtg ctt ggt ctg gac aat ctt act gat gat    480
Leu Lys Ser Glu His Ala Val Leu Gly Leu Asp Asn Leu Thr Asp Asp
145                 150                 155                 160 aat gca caa aga gct att tta aaa aaa cat gca aat aaa gat aag ggt    528
Asn Ala Gln Arg Ala Ile Leu Lys Lys His Ala Asn Lys Asp Lys Gly
                165                 170                 175 gct gca gaa ctt gaa aag tta ttt aaa gcg gta gaa aac tta tca aaa    576
Ala Ala Glu Leu Glu Lys Leu Phe Lys Ala Val Glu Asn Leu Ser Lys
            180                 185                 190 gca gct caa gac aca tta aaa aat gct gtt aaa gag ctt aca agt cct    624
Ala Ala Gln Asp Thr Leu Lys Asn Ala Val Lys Glu Leu Thr Ser Pro
        195                 200                 205 att gtc cat ggt aat aat tca gga aaa gat ggg aat aca tct gca aat    672
Ile Val His Gly Asn Asn Ser Gly Lys Asp Gly Asn Thr Ser Ala Asn
    210                 215                 220 tct gct gat gag tct gtt aaa ggg cct aat ctt aca gaa ata agt aaa    720
Ser Ala Asp Glu Ser Val Lys Gly Pro Asn Leu Thr Glu Ile Ser Lys
225                 230                 235                 240 aaa att aca gaa tct aac gca gtt gtt ctg gct gtg aaa gaa att gaa    768
Lys Ile Thr Glu Ser Asn Ala Val Val Leu Ala Val Lys Glu Ile Glu
                245                 250                 255 act ttg ctt gca tct ata gat gaa ctt gct act aaa gct att ggt aaa    816
Thr Leu Leu Ala Ser Ile Asp Glu Leu Ala Thr Lys Ala Ile Gly Lys
            260                 265                 270 aaa ata caa caa aat ggt ggt tta gct gtc gaa gcg ggg cat aat gga    864
Lys Ile Gln Gln Asn Gly Gly Leu Ala Val Glu Ala Gly His Asn Gly
        275                 280                 285 aca ttg tta gca ggt gct tat aca ata tca aaa cta ata aca caa aaa    912
Thr Leu Leu Ala Gly Ala Tyr Thr Ile Ser Lys Leu Ile Thr Gln Lys
    290                 295                 300 tta gat gga ttg aaa aat tca gaa aaa tta aag gaa aaa att gaa aat    960
Leu Asp Gly Leu Lys Asn Ser Glu Lys Leu Lys Glu Lys Ile Glu Asn
305                 310                 315                 320 gct aag aaa tgt tct gaa gat ttt act aaa aaa cta gaa gga gaa cat   1008
Ala Lys Lys Cys Ser Glu Asp Phe Thr Lys Lys Leu Glu Gly Glu His
                325                 330                 335 gcg caa ctt gga att gaa aat gtt act gat gag aat gca aaa aaa gct   1056
Ala Gln Leu Gly Ile Glu Asn Val Thr Asp Glu Asn Ala Lys Lys Ala
            340                 345                 350 att tta ata aca gat gca gct aaa gat aag ggc gct gca gag ctt gaa   1104
Ile Leu Ile Thr Asp Ala Ala Lys Asp Lys Gly Ala Ala Glu Leu Glu
        355                 360                 365 aag cta ttt aaa gca gta gaa aac ttg gca aaa gca gct aaa gag atg   1152
Lys Leu Phe Lys Ala Val Glu Asn Leu Ala Lys Ala Ala Lys Glu Met
    370                 375                 380 ctt gct aat tca gtt aaa gag ctt ac                                1178
Leu Ala Asn Ser Val Lys Glu Leu
385                 390
```

<210> SEQ ID NO 74
<211> LENGTH: 392

<212> TYPE: PRT
<213> ORGANISM: ospC Chimera

<400> SEQUENCE: 74

```
Met Arg Leu Leu Ile Gly Phe Ala Leu Ala Leu Ala Leu Ile Gly Cys
 1               5                  10                  15

Ala Gln Lys Gly Ala Glu Ser Ile Gly Ser Cys Asn Asn Ser Gly Lys
            20                  25                  30

Asp Gly Asn Ala Ser Ala Asn Ser Ala Asp Glu Ser Val Lys Gly Pro
        35                  40                  45

Asn Leu Thr Glu Ile Ser Lys L

<210> SEQ ID NO 75
<211> LENGTH: 1178
<212> TYPE: DNA
<213> ORGANISM: ospC Chimera
<220> FEATURE -continued

```
aaa ata ggc aat aat ggt tta gag gcc aat cag agt aaa aac aca tca      864
Lys Ile Gly Asn Asn Gly Leu Glu Ala Asn Gln Ser Lys Asn Thr Ser
        275                 280                 285 ttg tta tca gga gct tat gca ata tct gac cta ata gca gaa aaa tta      912
Leu Leu Ser Gly Ala Tyr Ala Ile Ser Asp Leu Ile Ala Glu Lys Leu
    290                 295                 300 aat gta ttg aaa aat gaa gaa tta aag gaa aag att gat aca gct aag      960
Asn Val Leu Lys Asn Glu Glu Leu Lys Glu Lys Ile Asp Thr Ala Lys
305                 310                 315                 320 caa tgt tct aca gaa ttt act aat aaa cta aaa agt gaa cat gca gtg     1008
Gln Cys Ser Thr Glu Phe Thr Asn Lys Leu Lys Ser Glu His Ala Val
            325                 330                 335 ctt ggt ctg gac aat ctt act gat gat aat gca caa aga gct att tta     1056
Leu Gly Leu Asp Asn Leu Thr Asp Asp Asn Ala Gln Arg Ala Ile Leu
        340                 345                 350 aaa aaa cat gca aat aaa gat aag ggt gct gca gaa ctt gaa aag tta     1104
Lys Lys His Ala Asn Lys Asp Lys Gly Ala Ala Glu Leu Glu Lys Leu
    355                 360                 365 ttt aaa gcg gta gaa aac tta tca aaa gca gct caa gac aca tta aaa     1152
Phe Lys Ala Val Glu Asn Leu Ser Lys Ala Ala Gln Asp Thr Leu Lys
370                 375                 380 aat gct gtt aaa gag ctt aca agt cc                                  1178
Asn Ala Val Lys Glu Leu Thr Ser
385                 390

<210> SEQ ID NO 76
<211> LENGTH: 392
<212> TYPE: PRT
<213> ORGANISM: ospC Chimera

<400> SEQUENCE: 76

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Cys Asn Asn Ser Gly Lys
            20                  25                  30

Asp Gly Asn Ala Ser Ala Asn Ser Ala Asp Glu Ser Val Lys Gly Pro
        35                  40                  45

Asn Leu Thr Glu Ile Ser Lys Lys Ile Thr Glu Ser Asn Ala Val Val
    50                  55                  60

Leu Ala Val Lys Glu Val Glu Thr Leu Leu Ala Ser Ile Asp Glu Leu
65                  70                  75                  80

Ala Thr Lys Ala Ile Gly Lys Lys Ile Gly Asn Asn Gly Leu Glu Ala
                85                  90                  95

Asn Gln Ser Lys Asn Thr Ser Leu Leu Ser Gly Ala Tyr Ala Ile Ser
            100                 105                 110

Asp Leu Ile Ala Glu Lys Leu Asn Val Leu Lys Asn Glu Glu Leu Lys
        115                 120                 125

Glu Lys Ile Asp Thr Ala Lys Gln Cys Ser Thr Glu Phe Thr Asn Lys
    130                 135                 140

Leu Lys Ser Glu His Ala Val Leu Gly Leu Asp Asn Leu Thr Asp Asp
145                 150                 155                 160

Asn Ala Gln Arg Ala Ile Leu Lys Lys His Ala Asn Lys Asp Lys Gly
                165                 170                 175

Ala Ala Glu Leu Glu Lys Leu Phe Lys Ala Val Glu Asn Leu Ser Lys
            180                 185                 190

Ala Ala Gln Asp Thr Leu Lys Asn Ala Val Lys Glu Leu Thr Ser Pro
        195                 200                 205
```

```
Ile Val His Gly Asn Asn Ser Arg Lys Asp Gly Asn Ala Ser Thr Asn
    210                 215                 220
Ser Ala Asp Glu Ser Val Lys Gly Pro Asn Leu Thr Glu Ile Ser Lys
225                 230                 235                 240
Lys Ile Thr Glu Ser Asn Ala Val Val Leu Ala Val Lys Glu Val Glu
                245                 250                 255
Thr Leu Leu Ala Ser Ile Asp Glu Leu Ala Thr Lys Ala Ile Gly Lys
            260                 265                 270
Lys Ile Gly Asn Asn Gly Leu Glu Ala Asn Gln Ser Lys Asn Thr Ser
        275                 280                 285
Leu Leu Ser Gly Ala Tyr Ala Ile Ser Asp Leu Ile Ala Glu Lys Leu
    290                 295                 300
Asn Val Leu Lys Asn Glu Glu Leu Lys Glu Lys Ile Asp Thr Ala Lys
305                 310                 315                 320
Gln Cys Ser Thr Glu Phe Thr Asn Lys Leu Lys Ser Glu His Ala Val
                325                 330                 335
Leu Gly Leu Asp Asn Leu Thr Asp Asp Asn Ala Gln Arg Ala Ile Leu
            340                 345                 350
Lys Lys His Ala Asn Lys Asp Lys Gly Ala Ala Glu Leu Glu Lys Leu
        355                 360                 365
Phe Lys Ala Val Glu Asn Leu Ser Lys Ala Ala Gln Asp Thr Leu Lys
    370                 375                 380
Asn Ala Val Lys Glu Leu Thr Ser
385                 390
```

<210> SEQ ID NO 77
<211> LENGTH: 1230
<212> TYPE: DNA
<213> ORGANISM: ospC Chimera
<220> FE

| | | | | | | | | | | | | | | | | |
|---|---|---|---|---|---|---|---|---|---|---|---|---|---|---|---|---|
| aag | gaa | aaa | att | gat | gcg | gct | aag | aaa | tgt | tct | gaa | aca | ttt | act | aat | 432 |
| Lys | Glu | Lys | Ile | Asp | Ala | Ala | Lys | Lys | Cys | Ser | Glu | Thr | Phe | Thr | Asn | |
| | 130 | | | | 135 | | | | 140 | | | | | | | |
| aaa | tta | aaa | gaa | aaa | cac | aca | gat | ctt | ggt | aaa | gaa | ggt | gtt | act | gat | 480 |
| Lys | Leu | Lys | Glu | Lys | His | Thr | Asp | Leu | Gly | Lys | Glu | Gly | Val | Thr | Asp | |
| 145 | | | | | 150 | | | | 155 | | | | | 160 | | |
| gct | gat | gca | aaa | gaa | gcc | att | tta | aaa | aca | aat | ggt | act | aaa | act | aaa | 528 |
| Ala | Asp | Ala | Lys | Glu | Ala | Ile | Leu | Lys | Thr | Asn | Gly | Thr | Lys | Thr | Lys | |
| | | | | 165 | | | | | 170 | | | | | 175 | | |
| ggt | gct | gaa | gaa | ctt | gga | aaa | tta | ttt | gaa | tca | gta | gag | gtc | ttg | tca | 576 |
| Gly | Ala | Glu | Glu | Leu | Gly | Lys | Leu | Phe | Glu | Ser | Val | Glu | Val | Leu | Ser | |
| | | | 180 | | | | | 185 | | | | | 190 | | | |
| aaa | gca | gct | aaa | gag | atg | ctt | gct | aat | tca | gtt | aaa | gag | ctt | aca | agc | 624 |
| Lys | Ala | Ala | Lys | Glu | Met | Leu | Ala | Asn | Ser | Val | Lys | Glu | Leu | Thr | Ser | |
| | | | | 195 | | | | | 200 | | | | | 205 | | |
| cct | gtt | gtg | gca | gaa | agt | cca | aaa | aaa | cct | ttc | cat | ggt | aat | aat | tca | 672 |
| Pro | Val | Val | Ala | Glu | Ser | Pro | Lys | Lys | Pro | Phe | His | Gly | Asn | Asn | Ser | |
| | | 210 | | | | | 215 | | | | | 220 | | | | |
| ggt | ggg | gat | tct | gca | tct | act | aat | cct | gat | gag | tct | gca | aaa | gga | cct | 720 |
| Gly | Gly | Asp | Ser | Ala | Ser | Thr | Asn | Pro | Asp | Glu | Ser | Ala | Lys | Gly | Pro | |
| 225 | | | | | 230 | | | | | 235 | | | | | 240 | |
| aat | ctt | acc | gta | ata | agc | aaa | aaa | att | aca | gat | tct | aat | gca | ttt | tta | 768 |
| Asn | Leu | Thr | Val | Ile | Ser | Lys | Lys | Ile | Thr | Asp | Ser | Asn | Ala | Phe | Leu | |
| | | | | 245 | | | | | 250 | | | | | 255 | | |
| ctg | gct | gtg | aaa | gaa | gtt | gag | gct | ttg | ctt | tca | tct | ata | gat | gaa | ctt | 816 |
| Leu | Ala | Val | Lys | Glu | Val | Glu | Ala | Leu | Leu | Ser | Ser | Ile | Asp | Glu | Leu | |
| | | | 260 | | | | | 265 | | | | | 270 | | | |
| tct | aaa | gct | att | ggt | aaa | aaa | ata | aaa | aat | gat | ggt | act | tta | gat | aac | 864 |
| Ser | Lys | Ala | Ile | Gly | Lys | Lys | Ile | Lys | Asn | Asp | Gly | Thr | Leu | Asp | Asn | |
| | | 275 | | | | | 280 | | | | | 285 | | | | |
| gaa | gca | aat | cga | aac | gaa | tca | ttg | ata | gca | gga | gct | tat | gaa | ata | tca | 912 |
| Glu | Ala | Asn | Arg | Asn | Glu | Ser | Leu | Ile | Ala | Gly | Ala | Tyr | Glu | Ile | Ser | |
| 290 | | | | | 295 | | | | | 300 | | | | | | |
| aaa | cta | ata | aca | caa | aaa | tta | agt | gta | ttg | aat | tca | gaa | gaa | tta | aag | 960 |
| Lys | Leu | Ile | Thr | Gln | Lys | Leu | Ser | Val | Leu | Asn | Ser | Glu | Glu | Leu | Lys | |
| 305 | | | | 310 | | | | | 315 | | | | | 320 | | |
| aaa | aaa | att | aaa | gag | gct | aag | gat | tgt | tcc | caa | aaa | ttt | act | act | aag | 1008 |
| Lys | Lys | Ile | Lys | Glu | Ala | Lys | Asp | Cys | Ser | Gln | Lys | Phe | Thr | Thr | Lys | |
| | | | | 325 | | | | | 330 | | | | | 335 | | |
| cta | aaa | gat | agt | cat | gca | gag | ctt | ggt | ata | caa | agc | gtt | cag | gat | gat | 1056 |
| Leu | Lys | Asp | Ser | His | Ala | Glu | Leu | Gly | Ile | Gln | Ser | Val | Gln | Asp | Asp | |
| | | | 340 | | | | | 345 | | | | | 350 | | | |
| aat | gca | aaa | aaa | gct | att | tta | aaa | aca | cat | gga | act | aaa | gac | aag | ggt | 1104 |
| Asn | Ala | Lys | Lys | Ala | Ile | Leu | Lys | Thr | His | Gly | Thr | Lys | Asp | Lys | Gly | |
| | | 355 | | | | | 360 | | | | | 365 | | | | |
| gct | aaa | gaa | ctt | gaa | gag | tta | ttt | aaa | tca | cta | gaa | agc | ttg | tca | aaa | 1152 |
| Ala | Lys | Glu | Leu | Glu | Glu | Leu | Phe | Lys | Ser | Leu | Glu | Ser | Leu | Ser | Lys | |
| 370 | | | | | 375 | | | | | 380 | | | | | | |
| gca | gcg | caa | gca | gca | tta | act | aat | tca | gtt | aaa | gag | ctt | aca | aat | cct | 1200 |
| Ala | Ala | Gln | Ala | Ala | Leu | Thr | Asn | Ser | Val | Lys | Glu | Leu | Thr | Asn | Pro | |
| 385 | | | | 390 | | | | | 395 | | | | | 400 | | |
| gtt | gtg | gca | gaa | agt | cca | aaa | aaa | cct | taa | | | | | | | 1230 |
| Val | Val | Ala | Glu | Ser | Pro | Lys | Lys | Pro | * | | | | | | | |
| | | 405 | | | | | | | | | | | | | | |

<210> SEQ ID NO 78
<211> LENGTH: 409
<212> TYPE: PRT
<213> ORGANISM: ospC Chimera

<400> SEQUENCE: 78

```
Met Arg Leu Leu Ile Gly Phe Ala Leu Ala Leu Ile Gly Cys
 1               5                  10                  15

Ala Gln Lys Gly Ala Glu Ser Ile Gly Ser Cys Asn Asn Ser Gly Lys
            20                  25                  30

Asp Gly Asn Thr Ser Ala Asn Ser Ala Asp Glu Ser Val Lys Gly Pro
            35                  40                  45

Asn Leu Thr Glu Ile Ser Lys Lys Ile Thr Asp Ser Asn Ala Val Leu
        50                  55                  60

Leu Ala Val Lys Glu Val Glu Ala Leu Leu Ser Ser Ile Asp Glu Ile
65                  70                  75                  80

Ala Ala Lys Ala Ile Gly Lys Lys Ile His Gln Asn Asn Gly Leu Asp
                85                  90                  95

Thr Glu Tyr Asn His Asn Gly Ser Leu Leu Ala Gly Ala Tyr Ala Ile
            100                 105                 110

Ser Thr Leu Ile Lys Gln Lys Leu Asp Gly Leu Lys Asn Glu Gly Leu
        115                 120                 125

Lys Glu Lys Ile Asp Ala Ala Lys Lys Cys Ser Glu Thr Phe Thr Asn
130                 135                 140

Lys Leu Lys Glu Lys His Thr Asp Leu Gly Lys Glu Gly Val Thr Asp
145                 150                 155                 160

Ala Asp Ala Lys Glu Ala Ile Leu Lys Thr Asn Gly Thr Lys Thr Lys
                165                 170                 175

Gly Ala Glu Glu Leu Gly Lys Leu Phe Glu Ser Val Glu Val Leu Ser
            180                 185                 190

Lys Ala Ala Lys Glu Met Leu Ala Asn Ser Val Lys Glu Leu Thr Ser
        195                 200                 205

Pro Val Val Ala Glu Ser Pro Lys Lys Pro Phe His Gly Asn Asn Ser
210                 215                 220

Gly Gly Asp Ser Ala Ser Thr Asn Pro Asp Glu Ser Ala Lys Gly Pro
225                 230                 235                 240

Asn Leu Thr Val Ile Ser Lys Lys Ile Thr Asp Ser Asn Ala Phe Leu
                245                 250                 255

Leu Ala Val Lys Glu Val Glu Ala Leu Leu Ser Ser Ile Asp Glu Leu
            260                 265                 270

Ser Lys Ala Ile Gly Lys Lys Ile Lys Asn Asp Gly Thr Leu Asp Asn
        275                 280                 285

Glu Ala Asn Arg Asn Glu Ser Leu Ile Ala Gly Ala Tyr Glu Ile Ser
    290                 295                 300

Lys Leu Ile Thr Gln Lys Leu Ser Val Leu Asn Ser Glu Glu Leu Lys
305                 310                 315                 320

Lys Lys Ile Lys Glu Ala Lys Asp Cys Ser Gln Lys Phe Thr Thr Lys
                325                 330                 335

Leu Lys Asp Ser His Ala Glu Leu Gly Ile Gln Ser Val Gln Asp Asp
            340                 345                 350

Asn Ala Lys Lys Ala Ile Leu Lys Thr His Gly Thr Lys Asp Lys Gly
        355                 360                 365

Ala Lys Glu Leu Glu Glu Leu Phe Lys Ser Leu Glu Ser Leu Ser Lys
    370                 375                 380

Ala Ala Gln Ala Ala Leu Thr Asn Ser Val Lys Glu Leu Thr Asn Pro
385                 390                 395                 400

Val Val Ala Glu Ser Pro Lys Lys Pro
                405
```

-continued

<210> SEQ ID NO 79
<211> LENGTH: 1209
<212> TYPE: DNA
<213> ORGANISM: ospC Chimera
<220> FEATURE:
<221> NAME/KEY: CDS
<222> LOCATION: (1)...(1209)

<400> SEQUENCE: 79

| | | | | | | | | | | | | | | | | |
|---|---|---|---|---|---|---|---|---|---|---|---|---|---|---|---|---|
| atg | aga | tta | tta | ata | gga | ttt | gct | tta | gcg | tta | gct | tta | ata | gga | tgt | 48 |
| Met | Arg | Leu | Leu | Ile | Gly | Phe | Ala | Leu | Ala | Leu | Ala | Leu | Ile | Gly | Cys | |
| 1 | | | | 5 | | | | | 10 | | | | | 15 | | |
| gca | caa | aaa | ggt | gct | gag | tca | att | gga | tcc | tgt | aat | aat | tca | ggg | aaa | 96 |
| Ala | Gln | Lys | Gly | Ala | Glu | Ser | Ile | Gly | Ser | Cys | Asn | Asn | Ser | Gly | Lys | |
| | | | 20 | | | | | 25 | | | | | 30 | | | |
| gat | ggg | aat | aca | tct | gca | aat | tct | gct | gat | gag | tct | gtt | aaa | ggg | cct | 144 |
| Asp | Gly | Asn | Thr | Ser | Ala | Asn | Ser | Ala | Asp | Glu | Ser | Val | Lys | Gly | Pro | |
| | 35 | | | | | 40 | | | | | 45 | | | | | |
| aat | ctt | aca | gaa | ata | agt | aaa | aaa | att | acg | gat | tct | aat | gcg | gtt | tta | 192 |
| Asn | Leu | Thr | Glu | Ile | Ser | Lys | Lys | Ile | Thr | Asp | Ser | Asn | Ala | Val | Leu | |
| 50 | | | | | 55 | | | | | 60 | | | | | | |
| ctt | gct | gtg | aaa | gag | gtt | gaa | gcg | ttg | ctg | tca | tct | ata | gat | gaa | att | 240 |
| Leu | Ala | Val | Lys | Glu | Val | Glu | Ala | Leu | Leu | Ser | Ser | Ile | Asp | Glu | Ile | |
| 65 | | | | 70 | | | | | 75 | | | | | 80 | | |
| gct | gct | aaa | gct | att | ggt | aaa | aaa | ata | cac | caa | aat | aat | ggt | ttg | gat | 288 |
| Ala | Ala | Lys | Ala | Ile | Gly | Lys | Lys | Ile | His | Gln | Asn | Asn | Gly | Leu | Asp | |
| | | | 85 | | | | | 90 | | | | | 95 | | | |
| acc | gaa | tat | aat | cac | aat | gga | tca | ttg | tta | gcg | gga | gct | tat | gca | ata | 336 |
| Thr | Glu | Tyr | Asn | His | Asn | Gly | Ser | Leu | Leu | Ala | Gly | Ala | Tyr | Ala | Ile | |
| | | | 100 | | | | | 105 | | | | | 110 | | | |
| tca | acc | cta | ata | aaa | caa | aaa | tta | gat | gga | ttg | aaa | aat | gaa | gga | tta | 384 |
| Ser | Thr | Leu | Ile | Lys | Gln | Lys | Leu | Asp | Gly | Leu | Lys | Asn | Glu | Gly | Leu | |
| | | 115 | | | | | 120 | | | | | 125 | | | | |
| aag | gaa | aaa | att | gat | gcg | gct | aag | aaa | tgt | tct | gaa | aca | ttt | act | aat | 432 |
| Lys | Glu | Lys | Ile | Asp | Ala | Ala | Lys | Lys | Cys | Ser | Glu | Thr | Phe | Thr | Asn | |
| | 130 | | | | | 135 | | | | | 140 | | | | | |
| aaa | tta | aaa | gaa | aaa | cac | aca | gat | ctt | ggt | aaa | gaa | ggt | gtt | act | gat | 480 |
| Lys | Leu | Lys | Glu | Lys | His | Thr | Asp | Leu | Gly | Lys | Glu | Gly | Val | Thr | Asp | |
| 145 | | | | | 150 | | | | | 155 | | | | | 160 | |
| gct | gat | gca | aaa | gaa | gcc | att | tta | aaa | aca | aat | ggt | act | aaa | act | aaa | 528 |
| Ala | Asp | Ala | Lys | Glu | Ala | Ile | Leu | Lys | Thr | Asn | Gly | Thr | Lys | Thr | Lys | |
| | | | 165 | | | | | 170 | | | | | 175 | | | |
| ggt | gct | gaa | gaa | ctt | gga | aaa | tta | ttt | gaa | tca | gta | gag | gtc | ttg | tca | 576 |
| Gly | Ala | Glu | Glu | Leu | Gly | Lys | Leu | Phe | Glu | Ser | Val | Glu | Val | Leu | Ser | |
| | | | 180 | | | | | 185 | | | | | 190 | | | |
| aaa | gca | gct | aaa | gag | atg | ctt | gct | aat | tca | gtt | aaa | gag | ctt | aca | agc | 624 |
| Lys | Ala | Ala | Lys | Glu | Met | Leu | Ala | Asn | Ser | Val | Lys | Glu | Leu | Thr | Ser | |
| | | 195 | | | | | 200 | | | | | 205 | | | | |
| cct | gtt | gtg | gca | gaa | agt | cca | aaa | aaa | cct | tcc | atg | gta | aat | aat | tca | 672 |
| Pro | Val | Val | Ala | Glu | Ser | Pro | Lys | Lys | Pro | Ser | Met | Val | Asn | Asn | Ser | |
| | 210 | | | | | 215 | | | | | 220 | | | | | |
| ggg | aaa | gat | ggg | aat | aca | tct | gca | aat | tct | gct | gat | gag | tct | gtt | aaa | 720 |
| Gly | Lys | Asp | Gly | Asn | Thr | Ser | Ala | Asn | Ser | Ala | Asp | Glu | Ser | Val | Lys | |
| 225 | | | | | 230 | | | | | 235 | | | | | 240 | |
| ggg | cct | aat | ctt | aca | gaa | ata | agt | aaa | aaa | att | aca | gaa | tct | aac | gca | 768 |
| Gly | Pro | Asn | Leu | Thr | Glu | Ile | Ser | Lys | Lys | Ile | Thr | Glu | Ser | Asn | Ala | |
| | | | 245 | | | | | 250 | | | | | 255 | | | |
| gtt | gtt | ctc | gcc | gtg | aaa | gaa | gtt | gaa | act | ttg | ctt | aca | tct | ata | gat | 816 |
| Val | Val | Leu | Ala | Val | Lys | Glu | Val | Glu | Thr | Leu | Leu | Thr | Ser | Ile | Asp | |
| | | | 260 | | | | | 265 | | | | | 270 | | | |

```
gag ctt gct aaa gct att ggt aaa aaa ata aaa aac gat gtt agt tta      864
Glu Leu Ala Lys Ala Ile Gly Lys Lys Ile Lys Asn Asp Val Ser Leu
            275                 280                 285 gat aat gag gca gat cac aac gga tca tta ata tca gga gca tat tta      912
Asp Asn Glu Ala Asp His Asn Gly Ser Leu Ile Ser Gly Ala Tyr Leu
            290                 295                 300 att tca aac tta ata aca aaa aaa ata agt gca ata aaa gat tca gga      960
Ile Ser Asn Leu Ile Thr Lys Lys Ile Ser Ala Ile Lys Asp Ser Gly
305                 310                 315                 320 gaa ttg aag gca gaa att gaa aag gct aag aaa tgt tct gaa gaa ttt     1008
Glu Leu Lys Ala Glu Ile Glu Lys Ala Lys Lys Cys Ser Glu Glu Phe
                325                 330                 335 act gct aaa tta aaa ggt gaa cac aca gat ctt ggt aaa gaa ggc gtt     1056
Thr Ala Lys Leu Lys Gly Glu His Thr Asp Leu Gly Lys Glu Gly Val
            340                 345                 350 act gat gat aat gca aaa aaa gcc att tta aaa aca aat aat gat aaa     1104
Thr Asp Asp Asn Ala Lys Lys Ala Ile Leu Lys Thr Asn Asn Asp Lys
            355                 360                 365 act aag ggc gct gat gaa ctt gaa aag tta ttt gaa tca gta aaa aac     1152
Thr Lys Gly Ala Asp Glu Leu Glu Lys Leu Phe Glu Ser Val Lys Asn
370                 375                 380 ttg tca aaa gca gct aaa gag atg ctt act aat tca gtt aaa gag ctt     1200
Leu Ser Lys Ala Ala Lys Glu Met Leu Thr Asn Ser Val Lys Glu Leu
385                 390                 395                 400 aca agc taa                                                         1209
Thr Ser *

<210> SEQ ID NO 80
<211> LENGTH: 402
<212> TYPE: PRT
<213> ORGANISM: ospC Chimera

<400> SEQUENCE: 80

Met Arg Leu Leu Ile Gly Phe Ala Leu Ala Leu Ile Gly Cys
 1               5                  10                  15

Ala Gln Lys Gly Ala Glu Ser Ile Gly Ser Cys Asn Asn Ser Gly Lys
            20                  25                  30

Asp Gly Asn Thr Ser Ala Asn Ser Ala Asp Glu Ser Val Lys Gly Pro
        35                  40                  45

Asn Leu Thr Glu Ile Ser Lys Lys Ile Thr Asp Ser Asn Ala Val Leu
    50                  55                  60

Leu Ala Val Lys Glu Val Glu Ala Leu Leu Ser Ser Ile Asp Glu Ile
65                  70                  75                  80

Ala Ala Lys Ala Ile Gly Lys Lys Ile His Gln Asn Asn Gly Leu Asp
                85                  90                  95

Thr Glu Tyr Asn His Asn Gly Ser Leu Leu Ala Gly Ala Tyr Ala Ile
            100                 105                 110

Ser Thr Leu Ile Lys Gln Lys Leu Asp Gly Leu Lys Asn Glu Gly Leu
        115                 120                 125

Lys Glu Lys Ile Asp Ala Ala Lys Lys Cys Ser Glu Thr Phe Thr Asn
    130                 135                 140

Lys Leu Lys Glu Lys His Thr Asp Leu Gly Lys Glu Gly Val Thr Asp
145                 150                 155                 160

Ala Asp Ala Lys Glu Ala Ile Leu Lys Thr Asn Gly Thr Lys Thr Lys
                165                 170                 175

Gly Ala Glu Glu Leu Gly Lys Leu Phe Glu Ser Val Glu Val Leu Ser
            180                 185                 190
```

```
Lys Ala Ala Lys Glu Met Leu Ala Asn Ser Val Lys Glu Leu Thr Ser
            195                 200                 205

Pro Val Val Ala Glu Ser Pro Lys Pro Ser Met Val Asn Asn Ser
    210                 215                 220

Gly Lys Asp Gly Asn Thr Ser Ala Asn Ser Ala Asp Glu Ser Val Lys
225                 230                 235                 240

Gly Pro Asn Leu Thr Glu Ile Ser Lys Lys Ile Thr Glu Ser Asn Ala
                245                 250                 255

Val Val Leu Ala Val Lys Glu Val Glu Thr Leu Leu Thr Ser Ile Asp
            260                 265                 270

Glu Leu Ala Lys Ala Ile Gly Lys Lys Ile Lys Asn Asp Val Ser Leu
        275                 280                 285

Asp Asn Glu Ala Asp His Asn Gly Ser Leu Ile Ser Gly Ala Tyr Leu
    290                 295                 300

Ile Ser Asn Leu Ile Thr Lys Lys Ile Ser Ala Ile Lys Asp Ser Gly
305                 310                 315                 320

Glu Leu Lys Ala Glu Ile Glu Lys Ala Lys Lys Cys Ser Glu Glu Phe
                325                 330                 335

Thr Ala Lys Leu Lys Gly Glu His Thr Asp Leu Gly Lys Glu Gly Val
            340                 345                 350

Thr Asp Asp Asn Ala Lys Lys Ala Ile Leu Lys Thr Asn Asn Asp Lys
        355                 360                 365

Thr Lys Gly Ala Asp Glu Leu Glu Lys Leu Phe Glu Ser Val Lys Asn
    370                 375                 380

Leu Ser Lys Ala Ala Lys Glu Met Leu Thr Asn Ser Val Lys Glu Leu
385                 390                 395                 400

Thr Ser

<210> SEQ ID NO 81
<211> LENGTH: 1205
<212> TYPE: DNA
<213> ORGANISM: ospC Chimera
<220> FEATURE:

```
                100             105             110
tca acc cta ata aaa caa aaa tta gat gga ttg aaa aat gaa gga tta      384
Ser Thr Leu Ile Lys Gln Lys Leu Asp Gly Leu Lys Asn Glu Gly Leu
        115                 120                 125 aag gaa aaa att gat gcg gct aag aaa tgt tct gaa aca ttt act aat      432
Lys Glu Lys Ile Asp Ala Ala Lys Lys Cys Ser Glu Thr Phe Thr Asn
130                 135                 140 aaa tta aaa gaa aaa cac aca gat ctt ggt aaa gaa ggt gtt act gat      480
Lys Leu Lys Glu Lys His Thr Asp Leu Gly Lys Glu Gly Val Thr Asp
145                 150                 155                 160 gct gat gca aaa gaa gcc att tta aaa aca aat ggt act aaa act aaa      528
Ala Asp Ala Lys Glu Ala Ile Leu Lys Thr Asn Gly Thr Lys Thr Lys
                165                 170                 175 ggt gct gaa gaa ctt gga aaa tta ttt gaa tca gta gag gtc ttg tca      576
Gly Ala Glu Glu Leu Gly Lys Leu Phe Glu Ser Val Glu Val Leu Ser
            180                 185                 190 aaa gca gct aaa gag atg ctt gct aat tca gtt aaa gag ctt aca agc      624
Lys Ala Ala Lys Glu Met Leu Ala Asn Ser Val Lys Glu Leu Thr Ser
        195                 200                 205 cct gtt gtg gca gaa agt cca aaa aaa cct tcc atg gta aat aat tca      672
Pro Val Val Ala Glu Ser Pro Lys Lys Pro Ser Met Val Asn Asn Ser
    210                 215                 220 gga aaa gat ggg aat aca tct gca aat tct gct gat gag tct gtt aaa      720
Gly Lys Asp Gly Asn Thr Ser Ala Asn Ser Ala Asp Glu Ser Val Lys
225                 230                 235                 240 ggg cct aat ctt aca gaa ata agt aaa aaa att aca gaa tct aac gca      768
Gly Pro Asn Leu Thr Glu Ile Ser Lys Lys Ile Thr Glu Ser Asn Ala
                245                 250                 255 gtt gtt ctg gct gtg aaa gaa att gaa act ttg ctt gca tct ata gat      816
Val Val Leu Ala Val Lys Glu Ile Glu Thr Leu Leu Ala Ser Ile Asp
            260                 265                 270 gaa ctt gct act aaa gct att ggt aaa aaa ata caa caa aat ggt ggt      864
Glu Leu Ala Thr Lys Ala Ile Gly Lys Lys Ile Gln Gln Asn Gly Gly
        275                 280                 285 tta gct gtc gaa gcg ggg cat aat gga aca ttg tta gca ggt gct tat      912
Leu Ala Val Glu Ala Gly His Asn Gly Thr Leu Leu Ala Gly Ala Tyr
    290                 295                 300 aca ata tca aaa cta ata aca caa aaa tta gat gga ttg aaa aat tca      960
Thr Ile Ser Lys Leu Ile Thr Gln Lys Leu Asp Gly Leu Lys Asn Ser
305                 310                 315                 320 gaa aaa tta aag gaa aaa att gaa aat gct aag aaa tgt tct gaa gat     1008
Glu Lys Leu Lys Glu Lys Ile Glu Asn Ala Lys Lys Cys Ser Glu Asp
                325                 330                 335 ttt act aaa aaa cta gaa gga gaa cat gcg caa ctt gga att gaa aat     1056
Phe Thr Lys Lys Leu Glu Gly Glu His Ala Gln Leu Gly Ile Glu Asn
            340                 345                 350 gtt act gat gag aat gca aaa aaa gct att tta ata aca gat gca gct     1104
Val Thr Asp Glu Asn Ala Lys Lys Ala Ile Leu Ile Thr Asp Ala Ala
        355                 360                 365 aaa gat aag ggc gct gca gag ctt gaa aag cta ttt aaa gca gta gaa     1152
Lys Asp Lys Gly Ala Ala Glu Leu Glu Lys Leu Phe Lys Ala Val Glu
    370                 375                 380 aac ttg gca aaa gca gct aaa gag atg ctt gct aat tca gtt aaa gag     1200
Asn Leu Ala Lys Ala Ala Lys Glu Met Leu Ala Asn Ser Val Lys Glu
385                 390                 395                 400 ctt ac                                                              1205
Leu
```

<210> SEQ ID NO 82

<211> LENGTH: 401
<212> TYPE: PRT
<213> ORGANISM: ospC Chimera

<400> SEQUENCE: 82

Met Arg Leu Leu Ile Gly Phe Ala Leu Ala Leu Ala Leu Ile Gly Cys
1 5 10 15

Ala Gln Lys Gly Ala Glu Ser Ile Gly Ser Cys Asn Asn Ser Gly Lys
20 25 30

Asp Gly Asn Thr Ser Ala Asn Ser Ala Asp Glu Ser Val Lys Gly Pro
35 40 45

Asn Leu Thr Glu Ile Ser Lys Lys Ile Thr Asp Ser Asn Ala Val Leu
50 55 60

Leu Ala Val Lys Glu Val Glu Ala Leu Leu Ser Ser Ile Asp Glu Ile
65 70 75 80

Ala Ala Lys Ala Ile Gly Lys Lys Ile His Gln Asn Asn Gly Leu Asp
85 90 95

Thr Glu Tyr Asn His Asn Gly Ser Leu Leu Ala Gly Ala Tyr Ala Ile
100 105 110

Ser Thr Leu Ile Lys Gln Lys Leu Asp Gly Leu Lys Asn Glu Gly Leu
115 120 125

Lys Glu Lys Ile Asp Ala Ala Lys Lys Cys Ser Glu Thr Phe Thr Asn
130 135 140

Lys Leu Lys Glu Lys His Thr Asp Leu Gly Lys Glu Gly Val Thr Asp
145 150 155 160

Ala Asp Ala Lys Glu Ala Ile Leu Lys Thr Asn Gly Thr Lys Thr Lys
165 170 175

Gly Ala Glu Glu Leu Gly Lys Leu Phe Glu Ser Val Glu Val Leu Ser
180 185 190

Lys Ala Ala Lys Glu Met Leu Ala Asn Ser Val Lys Glu Leu Thr Ser
195 200 205

Pro Val Val Ala Glu Ser Pro Lys Lys Pro Ser Met Val Asn Asn Ser
210 215 220

Gly Lys Asp Gly Asn Thr Ser Ala Asn Ser Ala Asp Glu Ser Val Lys
225 230 235 240

Gly Pro Asn Leu Thr Glu Ile Ser Lys Lys Ile Thr Glu Ser Asn Ala
245 250 255

Val Val Leu Ala Val Lys Glu Ile Glu Thr Leu Leu Ala Ser Ile Asp
260 265 270

Glu Leu Ala Thr Lys Ala Ile Gly Lys Lys Ile Gln Gln Asn Gly Gly
275 280 285

Leu Ala Val Glu Ala Gly His Asn Gly Thr Leu Leu Ala Gly Ala Tyr
290 295 300

Thr Ile Ser Lys Leu Ile Thr Gln Lys Leu Asp Gly Leu Lys Asn Ser
305 310 315 320

Glu Lys Leu Lys Glu Lys Ile Glu Asn Ala Lys Lys Cys Ser Glu Asp
325 330 335

Phe Thr Lys Lys Leu Glu Gly Glu His Ala Gln Leu Gly Ile Glu Asn
340 345 350

Val Thr Asp Glu Asn Ala Lys Lys Ala Ile Leu Ile Thr Asp Ala Ala
355 360 365

Lys Asp Lys Gly Ala Ala Glu Leu Glu Lys Leu Phe Lys Ala Val Glu
370 375 380

Asn Leu Ala Lys Ala Ala Lys Glu Met Leu Ala Asn Ser Val Lys Glu

```
                385                 390                 395                 400
Leu

<210> SEQ ID NO 83
<211> LENGTH: 1236
<212> TYPE: DNA
<213> ORGANISM: ospC Chimera
<220> FEATURE:
<221> NAME/KEY: CDS
<222> LOCATION: (1)...(1236)

<400> SEQUENCE: 83 atg aga tta tta ata gga ttt gct tta gcg tta gct tta ata gga tgt      48
Met Arg Leu Leu Ile Gly Phe Ala Leu Ala Leu Ala Leu Ile Gly Cys -continued

```
ttt tta ctg gct gtg aaa gaa gtt gag gct ttg ctt tca tct ata gat      816
Phe Leu Leu Ala Val Lys Glu Val Glu Ala Leu Leu Ser Ser Ile Asp
            260                 265                 270 gaa ctt tct aaa gct att ggt aaa aaa ata aaa aat gat ggt act tta      864
Glu Leu Ser Lys Ala Ile Gly Lys Lys Ile Lys Asn Asp Gly Thr Leu
        275                 280                 285 gat aac gaa gca aat cga aac gaa tca ttg ata gca gga gct tat gaa      912
Asp Asn Glu Ala Asn Arg Asn Glu Ser Leu Ile Ala Gly Ala Tyr Glu
    290                 295                 300 ata tca aaa cta ata aca caa aaa tta agt gta ttg aat tca gaa gaa      960
Ile Ser Lys Leu Ile Thr Gln Lys Leu Ser Val Leu Asn Ser Glu Glu
305                 310                 315                 320 tta aag aaa aaa att aaa gag gct aag gat tgt tcc caa aaa ttt act     1008
Leu Lys Lys Lys Ile Lys Glu Ala Lys Asp Cys Ser Gln Lys Phe Thr
                325                 330                 335 act aag cta aaa gat agt cat gca gag ctt ggt ata caa agc gtt cag     1056
Thr Lys Leu Lys Asp Ser His Ala Glu Leu Gly Ile Gln Ser Val Gln
            340                 345                 350 gat gat aat gca aaa aaa gct att tta aaa aca cat gga act aaa gac     1104
Asp Asp Asn Ala Lys Lys Ala Ile Leu Lys Thr His Gly Thr Lys Asp
        355                 360                 365 aag ggt gct aaa gaa ctt gaa gag tta ttt aaa tca cta gaa agc ttg     1152
Lys Gly Ala Lys Glu Leu Glu Glu Leu Phe Lys Ser Leu Glu Ser Leu
    370                 375                 380 tca aaa gca gcg caa gca gca tta act aat tca gtt aaa gag ctt aca     1200
Ser Lys Ala Ala Gln Ala Ala Leu Thr Asn Ser Val Lys Glu Leu Thr
385                 390                 395                 400 aat cct gtt gtg gca gaa agt cca aaa aaa cct taa                     1236
Asn Pro Val Val Ala Glu Ser Pro Lys Lys Pro  *
                405                 410

<210> SEQ ID NO 84
<211> LENGTH: 411
<212> TYPE: PRT
<213> ORGANISM: ospC Chimera

<400> SEQUENCE: 84

Met Arg Leu Leu Ile Gly Phe Ala Leu Ala Leu Ala Leu Ile Gly Cys
 1               5                  10                  15

Ala Gln Lys Gly Ala Glu Ser Ile Gly Ser Cys Ser Asn Ser Gly Lys
            20                  25                  30

Gly Gly Asp Ser Ala Ser Thr Asn Pro Ala Asp Glu Ser Ala Lys Gly
        35                  40                  45

Pro Asn Leu Thr Glu Ile Ser Lys Lys Ile Thr Asp Ser Asn Ala Phe
    50                  55                  60

Val Leu Ala Val Lys Glu Val Glu Thr Leu Val Leu Ser Ile Asp Glu
65                  70                  75                  80

Leu Ala Lys Lys Ala Ile Gly Gln Lys Ile Asp Asn Asn Asn Gly Leu
                85                  90                  95

Ala Ala Leu Asn Asn Gln Asn Gly Ser Leu Leu Ala Gly Ala Tyr Ala
            100                 105                 110

Ile Ser Thr Leu Ile Thr Glu Lys Leu Ser Lys Leu Lys Asn Leu Glu
        115                 120                 125

Glu Leu Lys Thr Glu Ile Ala Lys Ala Lys Lys Cys Ser Glu Glu Phe
    130                 135                 140

Thr Asn Lys Leu Lys Ser Gly His Ala Asp Leu Gly Lys Gln Asp Ala
145                 150                 155                 160

Thr Asp Asp His Ala Lys Ala Ala Ile Leu Lys Thr His Ala Thr Thr
```

```
                    165                 170                 175

Asp Lys Gly Ala Lys Glu Phe Lys Asp Leu Phe Glu Ser Val Glu Gly
                180                 185                 190

Leu Leu Lys Ala Ala Gln Val Ala Leu Thr Asn Ser Val Lys Glu Leu
            195                 200                 205

Thr Ser Pro Val Val Ala Glu Ser Pro Lys Pro His Met Ala Asn
        210                 215                 220

Asn Ser Gly Gly Asp Ser Ala Ser Thr Asn Pro Asp Glu Ser Ala Lys
225                 230                 235                 240

Gly Pro Asn Leu Thr Val Ile Ser Lys Lys Ile Thr Asp Ser Asn Ala
                245                 250                 255

Phe Leu Leu Ala Val Lys Glu Val Glu Ala Leu Leu Ser Ser Ile Asp
            260                 265                 270

Glu Leu Ser Lys Ala Ile Gly Lys Lys Ile Lys Asn Asp Gly Thr Leu
        275                 280                 285

Asp Asn Glu Ala Asn Arg Asn Glu Ser Leu Ile Ala Gly Ala Tyr Glu
    290                 295                 300

Ile Ser Lys Leu Ile Thr Gln Lys Leu Ser Val Leu Asn Ser Glu Glu
305                 310                 315                 320

Leu Lys Lys Lys Ile Lys Glu Ala Lys Asp Cys Ser Gln Lys Phe Thr
                325                 330                 335

Thr Lys Leu Lys Asp Ser His Ala Glu Leu Gly Ile Gln Ser Val Gln
            340                 345                 350

Asp Asp Asn Ala Lys Lys Ala Ile Leu Lys Thr His Gly Thr Lys Asp
        355                 360                 365

Lys Gly Ala Lys Glu Leu Glu Glu Leu Phe Lys Ser Leu Glu Ser Leu
    370                 375                 380

Ser Lys Ala Ala Gln Ala Ala Leu Thr Asn Ser Val Lys Glu Leu Thr
385                 390                 395                 400

Asn Pro Val Val Ala Glu Ser Pro Lys Lys Pro
                405                 410

<210> SEQ ID NO 85
<211> LENGTH: 192
<212> TYPE: PRT
<213> ORGANISM: borrelia burgdorferi

<400> SEQUENCE: 85

Cys Asn Asn Ser Gly Lys Asp Gly Asn Thr Ser Ala Asn Ser Ala Asp
1               5                   10                  15

Glu Ser Val Lys Gly Pro Asn Leu Thr Glu Ile Ser Lys Lys Ile Thr
            20                  25                  30

Glu Ser Asn Ala Val Val Leu Ala Val Lys Glu Val Glu Thr Leu Leu
        35                  40                  45

Thr Ser Ile Asp Glu Leu Ala Lys Ala Ile Gly Lys Lys Ile Lys Asn
    50                  55                  60

Asp Val Ser Leu Asp Asn Glu Ala Asp His Asn Gly Ser Leu Ile Ser
65                  70                  75                  80

Gly Ala Tyr Leu Ile Ser Thr Leu Ile Thr Lys Lys Ile Ser Ala Ile
                85                  90                  95

Lys Asp Ser Gly Glu Leu Lys Ala Glu Ile Glu Lys Ala Lys Lys Cys
            100                 105                 110

Ser Glu Glu Phe Thr Ala Lys Leu Lys Gly Glu His Thr Asp Leu Gly
        115                 120                 125
```

```
                                -continued

Lys Glu Gly Val Thr Asp Asp Asn Ala Lys Lys Ala Ile Leu Lys Thr
        130                 135                 140

Asn Asn Asp Lys Thr Lys Gly Ala Asp Glu Leu Glu Lys Leu Phe Glu
145                 150                 155                 160

Ser Val Lys Asn Leu Ser Lys Ala Ala Lys Glu Met Leu Thr Asn Ser
                165                 170                 175

Val Lys Glu Leu Thr Ser Pro Val Val Ala Glu Ser Pro Lys Lys Pro
            180                 185                 190

<210> SEQ ID NO 86
<211> LENGTH: 191
<212> TYPE: PRT
<213> ORGANISM: borrelia burgdorferi

<400> SEQUENCE: 86

Asn Ser Gly Lys Gly Gly Asn Thr Ser Ala Asn Ser Ala Asp Glu Ser
  1               5                  10                  15

Val Lys Gly Pro Asn Leu Thr Glu Ile Ser Lys Lys Ile Thr Glu Ser
                 20                  25                  30

Asn Ala Val Val Leu Ala Val Lys Glu Ile Glu Thr Leu Leu Ala Ser
             35                  40                  45

Ile Asp Glu Leu Ala Thr Lys Ala Ile Gly Lys Lys Ile Gln Gln Asn
 50                  55                  60

Gly Gly Leu Ala Val Glu Ala Gly His Asn Gly Thr Leu Leu Ala Gly
 65                  70                  75                  80

Ala Tyr Thr Ile Ser Lys Leu Ile Thr Gln Lys Leu Asp Gly Leu Lys
                 85                  90                  95

Asn Ser Glu Lys Leu Lys Glu Lys Ile Glu Asn Ala Lys Lys Cys Ser
                100                 105                 110

Glu Asp Phe Thr Lys Lys Leu Glu Gly Glu His Ala Gln Leu Gly Ile
            115                 120                 125

Glu Asn Val Thr Asp Glu Asn Ala Lys Lys Ala Ile Leu Ile Thr Asp
        130                 135                 140

Ala Ala Lys Asp Lys Gly Ala Ala Glu Leu Glu Lys Leu Phe Lys Ala
145                 150                 155                 160

Val Glu Asn Leu Ala Lys Ala Lys Glu Met Leu Ala Asn Ser Val
                165                 170                 175

Lys Glu Leu Thr Ser Pro Ile Val Ala Glu Ser Pro Lys Lys Pro
            180                 185                 190
```